(12) United States Patent
Bendahmane et al.

(10) Patent No.: US 11,236,357 B2
(45) Date of Patent: Feb. 1, 2022

(54) METHODS OF OBTAINING ANDROECIOUS CUCURBIT PLANTS

(71) Applicants: INSTITUT NATIONAL DE LA RECHERCHE AGRONOMIQUE (INRA), Paris (FR); VILMORIN ET CIE, Paris (FR)

(72) Inventors: Abdelhafid Bendahmane, Le Coudray Montceaux (FR); Christelle Troadec, Ivry-sur-Seine (FR); Adnane Boualem, Evry (FR); Daniele Hosemans, Angers (FR); Julie Fauve, Nimes (FR)

(73) Assignees: INSTITUT NATIONAL DE RECHERCHE POUR L'AGRICULTURE, L'ALIMENTATION ET L'ENVIRONNEMENT, Paris (FR); VILMORIN ET CIE, Paris (FR)

( * ) Notice: Subject to any disclaimer, the term of this patent is extended or adjusted under 35 U.S.C. 154(b) by 52 days.

(21) Appl. No.: 16/676,927

(22) Filed: Nov. 7, 2019

(65) Prior Publication Data
US 2020/0063156 A1    Feb. 27, 2020

Related U.S. Application Data

(62) Division of application No. 14/372,239, filed as application No. PCT/EP2013/000106 on Jan. 16, 2013, now Pat. No. 10,519,463.

(30) Foreign Application Priority Data

Jan. 16, 2012   (FR) .................................... 12/00149

(51) Int. Cl.
| | |
|---|---|
| A01H 5/08 | (2018.01) |
| A01H 6/34 | (2018.01) |
| A01H 1/06 | (2006.01) |
| C12N 15/82 | (2006.01) |
| A01H 1/04 | (2006.01) |

(52) U.S. Cl.
CPC ............ *C12N 15/8287* (2013.01); *A01H 1/04* (2013.01); *A01H 5/08* (2013.01); *A01H 6/34* (2018.05); *C12N 15/827* (2013.01); *C12N 15/829* (2013.01); *C12N 15/8218* (2013.01); *C12N 15/8249* (2013.01); *C12Y 404/01014* (2013.01)

(58) Field of Classification Search
None
See application file for complete search history.

(56) References Cited

U.S. PATENT DOCUMENTS

| | | |
|---|---|---|
| 8,319,018 B2 | 11/2012 | Bendahmane et al. |
| 2009/0288214 A1 | 11/2009 | Bendahmane et al. |
| 2010/0287669 A1 | 11/2010 | Bate et al. |
| 2011/0314569 A1 | 12/2011 | Bendahmane et al. |

FOREIGN PATENT DOCUMENTS

| | | |
|---|---|---|
| FR | 2 900 415 A1 | 11/2007 |
| FR | 2 934 277 A1 | 1/2010 |
| WO | 95/04064 A1 | 2/1995 |
| WO | 2007/125264 A2 | 11/2007 |
| WO | 2010/012948 A2 | 2/2010 |

OTHER PUBLICATIONS

International Search Report, dated Mar. 20, 2013, from corresponding PCT application No. PCT/EP2013/000106.
Okushima et al., "Auxin Response Factor 2 (ARF2): a pleiotropic developmental regulator", The Plant Journal, 2005, vol. 43, pp. 29-46.
Huang et al., UniPro Database, Acc. No. A0A0A0LKW1, Nat. Genet. 41:1275-1281, 2009.

*Primary Examiner* — Phuong T Bui
(74) *Attorney, Agent, or Firm* — Nixon & Vanderhye

(57) ABSTRACT

Disclosed is a method for the production of a plant of the Cucurbitaceae family by mutating seeds to induce a mutation of 1-aminocyclopropane-1-carboxylate synthase 8 (ACS8) and growing a plant from the mutated seed, with the plant having a androecy or androecious tendency.

6 Claims, 3 Drawing Sheets

Specification includes a Sequence Listing.

US 11,236,357 B2

METHODS OF OBTAINING ANDROECIOUS CUCURBIT PLANTS

This application is a divisional of U.S. Ser. No. 14/372,239 filed 2014 Jul. 15, now U.S. Pat. No. 10,519,463 issued Dec. 31, 2019, which was a national stage application, filed under 35 U.S.C. § 371, of International Patent Application No. PCT/EP2013/000106 filed 2013 Jan. 16, which claims priority French patent application no 12 00149 filed on 16 Jan. 2012. Each of the previously noted applications is hereby incorporated by reference in their entirety.

FIELD OF THE INVENTION

The present invention relates to the field of plant identification and in particular sex identification of plants. It concerns plants whose sex type has been modified, the use of such plants as well as methods of obtaining and detecting said plants.

PRIOR ART

The creation of hybrid plants is of major interest in agronomy and in agriculture. Indeed, hybrid plants thanks to the heterosis phenomenon, also called hybrid vigour, generally prove superior for many characters, with respect to the average of both their parents. This superiority can be illustrated for instance by better vigour, better yield, greater adaptation to the environment in which the hybrid is cultivated and high uniformity of hybrids with respect to their parents. This hybrid vigour is all the more important since the parents are genetically remote.

The creation of stable bloodlines, future parents of the hybrid, is an obligatory step for the creation of homogeneous and reproducible hybrid varieties expressing the largest heterosis. It is hence necessary to create bloodlines with the best possible homozygous genetic material, so-called "pure bloodlines", produced by self-fecundation for instance, and combining in the best possible way, then to cross two individuals of these bloodlines to obtain a hybrid.

When crossing these bloodlines together, it is indispensable to be able to choose the direction of the crossing and to avoid the self-pollination of the plants which would lead to plants without the sought-after hybrid vigour. The creation of hybrids therefore requires to obtain plants unable of self-pollination, i.e. having either solely female flowers, or solely male flowers.

The plants having only female flowers are called gynoecious. The plants having only male flowers are called androecious. Androecy is quite a sought-after agronomic character, in particular in that exclusively male flowers produce more pollen.

Besides, the plants having male flowers and separate female flowers but on the same plant are called monoecious, the plants having bisexual flowers are called hermaphrodite and the plants having bisexual and male flowers on the same plant are called andromonoecious.

In case when plants have the same floral sex type, i.e. monoecious, andromonoecious or hermaphrodite, it is necessary, for example, in the context of a programme for improving plants, possibly in the case of a production, especially of hybrid plants, to separate the male flowers from the female flowers of the same plant and to emasculate manually or chemically the hermaphrodite plants to avoid self-pollination.

A first technique, implemented especially for corn, consists in using mechanical means for emasculating the plants. However, this technique proves extremely costly since it requires emasculating each plant for which we wish to avoid self-pollination, for each crossing made.

Another technique consists in chemical emasculation of the plants, blocking the formation of viable pollen. Thus, in melon (*Cucumis meso*), the treatment of monoecious plants by ethrel (precursor of ethylene) causes the temporary disappearance of male flowers. Such chemicals, used to provoke transitory male sterility, with several shortcomings, like a high cost or a great toxicity.

The mechanical or chemical techniques for controlling the floral type described above hence prove quite costly and imperfect, all the more so since a very large number of crossings is necessary to obtain hybrid plants with sought-after characters, which then ought to be produced and marketed.

To facilitate the creation of hybrids, there is therefore a need for a system which would enable to control the development of the floral type of a plant of the Cucurbitaceae family and to obtain a plant of a determined floral type.

The family of the Cucurbitaceae includes more than 800 vegetable species distributed in 120 genera in the tropical and subtropical regions. This plant family includes several species of a major agronomic interest and which are cultivated in temperate regions such as the cucumber (*Cucumis sativus*), the melon (*Cucumis melo*), the water melon (*Citrullus lanatus*), the zucchini and the squash (*Cucurbita* spp, *cucurbita pepo*) or still the pumpkin (*Cucurbita maxima*) and the Hokkaido squash (*Cucurbita moschata*). Among the other species of agronomic interest especially present in the tropical and sub-tropical regions, there are the luffa (*Luffa acutangula*), the margosa (*Momordica charentia*) or still the gourd (*Lagenaria siceraria*).

Another avenue to obtain plants unable of self-pollination for the creation of hybrid could consist in a selection of exclusively female or exclusively male individuals, if they exist in the specie(s) of interest. However, such a technique would prove extremely costly since it would require the cultivation of a very large number of plants, until it is possible to determine the sex type.

The selection of exclusively male individuals in particular inasmuch as it enables to produce pollen only and in large amount. The pollen thus produced can be used for the pollination of plants with female flowers. Moreover, in some members of the Cucurbitaceae, such plants do not exists, such as for example for some of the plants of the *Cucumis, Cucurbita, Citrullus, Luffa, Lagenaria* and *Momordica* genera. In particular, plants of androecious melon (*Cucumis melo*, especially *spmelo, sspmelo*), of zucchini and of pumpkin (*Cucurbita pepo*), of water melon (*Citrullus lanatus*) or still of luffa (*Luffa acutangula*), of margosa (*Momordica charentia*), of gourd (*Lagenaria siceraria*), of cooking pumpkin (*Cucurbita maxima*) or of Hokkaido squash (*Cucurbita moschata*) have never been identified.

There is hence a need for a method which would enable to create androecious plants of the Cucurbitaceae family which do not exist in a natural state. This method would enable to identify the androecious plants without having to wait for said plants to flower. Moreover, this method should enable to identify particularly useful plants, for the realisation of hybrid in particular, as was specified above.

SUMMARY OF THE INVENTION

In the context of the present invention, the inventors have identified and characterised for the first time the gene responsible for the androecious sex phenotype in the cucumber (*Cucumis sativus*), a species for which androecy can be found in the natural state. The identified gene encodes the 1-aminocyclopropane-1-carboxylate synthase 8 (ACS8), noted below *Cucumis sativus* ACS8, CsACS8.

Furthermore, the inventors have identified the mutation in the CsACS8 gene responsible for the androecy in the cucumber.

In the melon, androecy does not exist in a natural state. The inventors have induced mutations in the orthologous gene of CsACS8 in the melon and have thus created androecious melon plants.

The Cucurbitaceae have served as a model for the study of sex dimorphism for decades. In the cucumber (*Cucumis sativus* L.), a monoecious plant, sex determinism is genetically controlled by three loci, F (Female), A (Androecious) and M (Monoecious). The semi-dominant locus F (Female) controls the degree of feminity. The allele F drives the early appearance of the female phase and consequently the plants FF are gynoecious (totally female). The Androecious locus (a) increases the masculinity and the plants of aaff genotype are androecious (totally male). The locus M (Monoecious) is required for the selection abortion of the male reproductive organs in the floral buds determined to develop a carpelle. The combination of the M-ff alleles enables the development of monoecious plants; the most widespread sex type in Cucurbitaceae, starting from male and female flowers. The gynoecious, hermaphrodite and andromonoecious plants (male and hermaphrodite flowers) include, respectively, the M-F, mmF and MMff genotypes. Using a candidate gene approach, it has been shown that an ACC synthase co-segregated with the locus F (Trebitsh et al., 1997) and that the monoecious plants have a single copy of this gene while gynoecious plants have an additional copy, the CsACS1G gene. Thanks to candidate gene, positional cloning and association genetic approach combination, Boualem et al., (2009) and Li et al., (2009) have demonstrated that the locus M corresponded to the ACC synthase CsACS2 and that the loss of activity of that enzyme caused the transition from monoecia to andromonoecia.

In the melon, another model Cucurbitaceae, sex determinism is controlled by two loci, the locus A (andromonoecious) and the locus G (gynoecious). The melons of A-G-genotype are of monoecious type (male and female flowers) while the andromonoecious plants (male and hermaphrodite flowers) carry the aaG-alleles. The gynoecious plants (exclusively female flowers) are AAgg and the hermaphrodites (exclusively hermaphrodite flowers) have an aagg genotype. Contrary to the cucumber, in the melon, never an androecious plant only bearing male flowers has been described. The nature of the locus A, responsible for the transition from the monoecious towards the andromonoecious sex type, has been revealed recently by the works of Boualem et al, 2008. These works have demonstrated that the A gene encoded for an ACC synthase, CmACS-7, and that the loss of function of that enzyme was the cause for the appearance of andromonoecia. These results have been disclosed in the patent WO/2007/125264. The recessive allele g, in combination with the allele A, causes the development of unisex female flowers or of hermaphrodite flowers, when combined with the allele a. Recently, the works of Martin et al, 2009 have put in evidence that the allele g was due to the insertion of a hAT-type transposon in the proximity of the C2H2 zinc finger transcription factor, named CmWIP1. The insertion of this transposable element inhibits, via epigenetic mechanisms, the expression of the transcription factor, CmWIP1. The identification of EMS-induced mutations in this transcription factor, mutations converting monoecious plants into gynoecious plants, confirms that the gene G is CmWIP1. These works were disclosed in the patent WO/2010/012948.

Based on the results described above, the sex determination mechanisms in the cucumber and the melon present several differences.

Firstly, in the cucumber the different sex types are determined by the allelic combinations of the 3 genes F, M and A, while in the melon the different sex types are controlled by only 2 genes, A and G. For information, the gene A, CmACS-7, of the melon is the ortholog of the gene M, CsACS2, of the cucumber.

Secondly, the gynoecious character is controlled in the cucumber by the gene F, an ACC synthase, whereas in the melon, this character is controlled by CmWIP1, a C2H2 type zinc finger transcription factor.

Thirdly, the androecy described in the cucumber is controlled by the gene A of the cucumber (different from the gene A of the melon) while in the melon, this sex type has never been described or reported as existing in melon populations.

The inventors have thus identified, for the first time, in the plants belonging to the Cucurbitaceae family, a gene responsible for the androecy.

Said gene is characterised by a non-mutated dominant allele inducing the synthesis of the 1-aminocyclopropane-1-carboxylic synthase protein (ACS8 active, enzyme limiting the path of ethylene biosynthesis), and by a mutated recessive allele inducing the synthesis of an inactive ACS8 protein or with reduced enzymatic activity.

The Cucurbitaceae according to the present invention having two recessive alleles for the gene of the ACS8 androecy are androecious.

The inventors have also demonstrated that two recessive alleles, both of them with reduced enzymatic activity of at least 50% with respect to a wild ACS8 was sufficient to drive this androecious phenotype.

Such androecious plants, only having male flowers, can be used for the creation of hybrids as well as for improving Cucurbitaceae species.

The Cucurbitaceae according to the present invention with a mutated recessive ACS8 allele of interest inasmuch as they have an androecious tendency, i.e. with more male flowers than the wild plant.

The plants according to the present invention, whether they are androecious or with an androecious tendency, can be used as a pollinator.

A first object of the invention concerns a plant, of the family of Cucurbitaceae, which plant is:
  selected among the group comprising the *Cucumis, Citrullus, Cucurbita, Luffa, Momordica* and *Lagenaria* genera, with the exclusion of the *Cucumis sativus* species; and
  characterised in that it comprises at least one allele of the non-encoding or encoding 1-aminocyclopropane-1-carboxylate synthase 8 (ACS8) for a polypeptide corresponding to a variant of the reference ACS8 for said plant, which reference 1-aminocyclopropane-1-carboxylate synthase 8 has a transforming activity of methionine S-adenosyl into aminocyclopropane carboxylate and which said variant has a lower activity of at least 50%, preferably at least 75% or 90%, still more preferably 95% or 99% with respect to said reference 1-aminocyclopropane-1-carboxylate synthase 8 and particularly preferably, said variant has a nil activity.

Another object of the invention concerns a plant, according to the invention characterised in that it is homozygous for the allele of the non-encoding or encoding 1-aminocyclopropane-1-carboxylate synthase 8 (ACS8) for a variant of the reference ACS8 and in that is androecious.

Another object of the invention concerns a seed whose germination leads to a plant as defined according to the invention.

Another object of the invention concerns a use of a plant according to the invention as a pollinator.

Another object of the invention concerns an isolated polypeptide corresponding to a variant of a reference 1-aminocyclopropane-1-carboxylate (ACS8), of a plant of the Cucurbitaceae family, which 1-aminocyclopropane-1-carboxylate synthase 8 has a transforming activity of methionine S-adenosyl into aminocyclopropane carboxylate and which said variant has a lower activity of at least 50%, preferably at least 75% or 90%, still more preferably 95% or 99% with respect to said reference 1-aminocyclopropane-1-carboxylate synthase 8 and particularly preferably, said variant has a nil activity.

Another object of the invention concerns an encoding polynucleotide for the polypeptide according to the invention.

Another object of the invention concerns a cell derived from a plant as defined in the present invention.

Another object of the invention concerns a method of producing an androecious plant of the Cucurbitaceae family, said method comprising the steps of:
  a) obtaining a plant of the Cucurbitaceae family, preferably selected among the group comprising the *Cucumis, Citrullus, Cucurbita, Luffa, Momordica* and *Lagenaria* genera,
  b) inhibiting the 1-aminocyclopropane-1-carboxylate synthase 8 (ACS8) of said plant.

Another object of the invention concerns a method of producing an androecious plant or with an androecious tendency, of the Cucurbitaceae family, said method comprising the steps of:
  a) obtaining a plant of the Cucurbitaceae family, which plant is selected among the group comprising the *Cucumis, Citrullus, Cucurbita, Luffa, Momordica* and *Lagenaria* genera,
  b) highlighting the presence of at least one allele of the non-encoding or encoding 1-aminocyclopropane-1-carboxylate synthase 8 (ACS8) for a polypeptide corresponding to a variant of the reference ACS8 for said plant,
  c) studying the transforming activity of the methionine S-adenosyl into aminocyclopropane carboxylate of the 1-aminocyclopropane-1-carboxylate synthase 8 encoded by said allele,
  d) selecting a plant having a transforming activity of the methionine S-adenosyl into aminocyclopropane carboxylate and which said variant has a lower activity of at least 50%, preferably at least 75% or 90%, still more preferably 95% or 99% with respect to said reference 1-aminocyclopropane-1-carboxylate synthase 8 and particularly preferably, said variant has a nil activity.

Another object of the invention concerns besides a propagation method of an androecious homozygous plant of the invention, comprising the steps of:
  a) treating homozygous androecious plants for the ACS8 mutated allele of the invention, with a compound enabling to induce an increased intracellular concentration in ethylene, for generating female flowers,
  b) self-pollination of the plants obtained at step a), and
  c) harvesting the seeds.

Another object of the invention concerns a method of identifying a plant having an encoding nucleic acid sequence for the polypeptide according to the invention and comprising the steps of:
  a) analysing a sample comprising cells of a plant of the Cucurbitaceae family or extracts thereof so as to identify whether said plant comprises an encoding nucleic acid sequence for the polypeptide according to the invention; and
  b) identifying a plant comprising such a nucleic acid sequence.

Now, another object of the invention concerns a method of selecting an androecious plant, said method comprising the steps of:
  a) analysing a sample comprising cells of a plant of the Cucurbitaceae family or extracts thereof so as to identify whether said plant comprises an encoding nucleic acid sequence for the polypeptide according to the invention,
  b) identifying a plant comprising such a nucleic acid sequence,
  c) crossing plants comprising an encoding nucleic acid sequence for a polypeptide according to the invention and as identified at step b), and
  d) selecting a homozygous plant for said nucleic acid sequence.

The invention also concerns a method of selecting a plant having at least two characters of interest, said method comprising the following steps:
  a) analysing a sample comprising cells of a plant of the Cucurbitaceae family having a first character of interest or extracts thereof so as to identify whether said plant comprises an encoding nucleic acid sequence for the polypeptide according to the invention, and
  b) identifying a plant including such a nucleic acid sequence and still having said first character of interest,
  c) crossing plants comprising an encoding nucleic acid sequence for a polypeptide according to the invention and still having said first character of interest, plants as identified at step b),
  d) selecting a plant and still having said first character of interest and homozygous for said nucleic acid sequence,
  e) crossing a plant having at least one first character of interest obtained at step d) with a plant of the Cucurbitaceae family having at least one second character of interest; and
  f) selecting a plant having at least first and second characters of interest.

Another object of the invention also concerns a method of producing a plant seed, preferably hybrid, diploid or triploid plant seed, comprising the steps of:
  a. seeding a field alternately with the androecious plants and/or with an androecious tendency of the invention comprising a first character of interest and gynoecious and/or sterile male plants as defined in the present invention comprising a second character of interest,
  b. harvesting the fruit of the plants obtained after pollination, and
  c. extracting said seeds from said fruit.

Another object of the invention concerns a seed, preferably hybrid, of a plant obtained by any of the methods of the invention. Preferably, the germination of said seed leads to a plant having said at least one and second characters of interest described previously.

Another object of the invention concerns a plant, of the Cucurbitaceae family, selected among the group comprising the *Cucumis, Citrullus, Cucurbita, Luffa, Momordica* and *Lagenaria* genera, with the exclusion of the *Cucumis sativus* species, and characterised in that it is androecious.

Another object of the invention concerns a use, for the identification of androecious plants of the Cucurbitaceae family, of probes or primers enabling to detect the polynucleotide according to the invention in a sample comprising cells of such a plant or extracts thereof.

A last object of the invention concerns a use, for the identification of androecious plants of the Cucurbitaceae family, of antibodies enabling to detect the polypeptide according to the invention in a sample comprising cells of such a plant or extracts thereof.

DETAILED DISCLOSURE OF THE INVENTION

Figure 1:
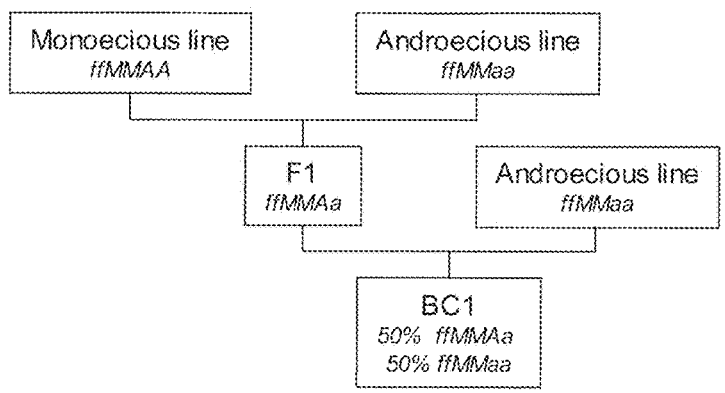
FIG. 1 represents the diagram of the crossings made to obtain the population of androecious cucumbers (*Cucumis sativus*) used for determining the gene responsible for androecy.

A first object of the invention concerns a plant, of the family of Cucurbitaceae, which plant is:
  selected among the group comprising the *Cucumis, Citrullus, Cucurbita, Luffa, Momordica* and *Lagenaria* genera, with the exclusion of the *Cucumis sativus* species; and
  characterised in that it comprises at least one allele of the non-encoding or encoding 1-aminocyclopropane-1-carboxylate synthase 8 (ACS8) for a polypeptide corresponding to a variant of the reference ACS8 for said plant, which reference 1-aminocyclopropane-1-carboxylate synthase 8 has a transforming activity of methionine S-adenosyl into aminocyclopropane carboxylate and which said variant has a lower activity of at least 50%, preferably at least 75% or 90%, still more preferably 95% or 99% with respect to said reference 1-aminocyclopropane-1-carboxylate synthase 8 and particularly preferably, said variant has a nil activity.

Advantageously, said transforming activity of methionine S-adenosyl into aminocyclopropane carboxylate corresponds to a Vmax smaller than or equal to 400 nmol·min$^{-1}$·mg$^{-1}$, preferably smaller than or equal to 300 and in a particularly preferable way smaller than or equal to 275 nmol·min$^{-1}$·mg$^{-1}$ in the presence of a concentration of 5 µM pyridoxal5'-phosphate (PLP).

Another object of the invention concerns a plant, according to the invention, characterised in that it is homozygous for the allele of the non-encoding or encoding 1-aminocyclopropane-1-carboxylate synthase 8 (ACS8) for a variant of the reference ACS8 and in that is androecious.

By "plant" is meant a plant as a whole but also a fragment or an isolated part of a plant like a root derived from said plant, a leave, a stem, a flower, a piece of fruit, etc.

By "plants of the Cucurbitaceae family" are meant, in the sense of the present invention, the dicotyledon plants of the Cucurbitaceae family and comprising in particular the *Cucumis, Cucurbita, Citrullus, Lagenaria, Luffa, Momordica, Cyclanthera, Echinocystis, Thladiantha, Bryona, Trichosanthes, Melothria, Ibervillea, Ecballium, Sechium, Benincasa, Sicyos, Coccinia* genera.

Preferably, said plant is selected from the group consisting of the *Cucumis, Citrullus, Cucurbita, Luffa, Lagenaria* and *Momordica* genera.

Still preferably, said plant is selected from the group consisting of the *Cucumis melo, Citrullus lanatus, Cucurbita pepo, Luffa acutangula, Lagenaria siceraria, Momordica charentia, Cucurbita maxima* and *Cucurbita moschate* species.

The *Cucumis melo, Citrullus lanatus, Cucurbita pepo, Luffa acutangula, Lagenaria siceraria, Momordica charentia, Cucurbita maxima* and *Cucurbita moschata* Cucurbitaceae with the androecious phenotype have never been identified in the wild. The only phenotypes identified are, for *Cucumis melo*, the andromonoecious, gynoecious, monoecious and hermaphrodite phenotypes; for *Citrullus lanatus*, the andromonoecious and monoecious phenotypes for *Cucurbita pepo*, the monoecious phenotype, for *Luffa acutangula*, the andromonoecious, gynoecious, monoecious and hermaphrodite phenotypes; for *Lagenaria siceraria*, the monoecious and andromonoecious phenotypes and for *Momordica charentia*, the monoecious and gynoecious phenotypes. In the *Cucumis sativus*, the phenotypes present are the monoecious, andromonoecious, androecious, gynoecious and hermaphrodite phenotypes. In *Cucurbita maxima* and *Cucurbita moschata*, the phenotype present is the monoecious phenotype.

Such a plant can be obtained by the selection method of an androecious plant described below.

The terms "polypeptide" or "protein", in the sense of the present invention, refer to any amino acid chain, regardless of their length or their possible post-translational modifications (such as glycosylation, phosphorylation, alkylation, etc.).

The aminocyclopropane carboxylate synthase (ACS8) polypeptide sequence in the sense of the present invention refers to the aminocyclopropane carboxylate synthase 8 enzyme transforming the methionine S-adenosyl into aminocyclopropane carboxylate.

This ACS8 enzyme is also known under other denominations, i.e. 1-aminocyclopropane-1-carboxylate synthase 8, 1-amino-cyclopropane-1-carboxylate synthase 8, ACC synthase 8, S-adenosyl-L-methionine methylthioadenosinelyase 8 or still ACS8.

By "wild" allele is meant in the sense of the present invention any encoding natural allele for a protein with an enzymatic activity similar or identical to that of the reference ACS8. The wild alleles in the sense of the present invention correspond to the genomic sequences SEQ ID No 1, SEQ ID No 10, SEQ ID No 19, SEQ ID No 22, SEQ ID No 25, SEQ ID No 28, SEQ ID No 31, SEQ ID No 34 and to the encoding sequences SEQ ID No 2, SEQ ID No 11, SEQ ID No 20, SEQ ID No 23, SEQ ID No 26, SEQ ID No 29, SEQ ID No 32 and SEQ ID No 35. By "reference sequence" in the sense of the present invention, is meant for a determined species of plant of the Cucurbitaceae family, the 1-aminocyclopropane-1-carboxylique synthase 8 protein encoded by a wild allele with 100% ACS8 activity. This reference sequence is characterised in that it is encoded by a nucleic acid sequence corresponding to a dominant allele present in monoecious, andromonoecious, gynoecious and hermaphrodite plants.

By way of example, reference ACS8 sequences for the *Cucumis sativus, Cucumis melo, Citrullus lanatus, Luffa acutangula, Lagenaria siceraria, Momordica charentia* and *Cucurbita pepo* species correspond to the sequences SEQ ID No 3, SEQ ID No 12, SEQ ID No 21, SEQ ID No 24, SEQ ID No 27, SEQ ID No 30, SEQ ID No 33 et SEQ ID No 36 respectively. By "variant" of a polypeptide sequence according to the invention, is meant a polypeptide sequence which differs from the reference polypeptide sequence by at least one punctual mutation or which corresponds to a fragment thereof.

By "fragment" of a reference polypeptide sequence, is meant a polypeptide sequence of reduced length with respect to the preferred polypeptide sequence, preferably with a shorter length of at least 10%, by way of example of at least 25 or 33%, and in a particularly preferable way of at least 50%.

A variant of a polypeptide sequence according to the invention may be of natural origin, such as a variant derived from an allelic variation pre-existing in the wild. Such a variant may also be a non-pre-existing polypeptide sequence in nature and obtained, for instance, by mutagenesis techniques. Preferably, such a variant is obtained upon completion of a mutagenesis step.

The activity of the ACS8 enzyme can be determined simply by the man of the art in the light of his general knowledge. By way of example, this activity can be determined by the method as described in example 8 of the application.

By way of example of such variants, the variants presenting the sequences SEQ ID no 6 and SEQ ID No 9 of *Cucumis sativus*, the variants presenting the sequences SEQ ID no 15 and SEQ ID No 18 of *Cucumis melo* may be quoted.

By "androecious plant" is meant in the sense of the present invention a plant carrying only male flowers. Said (staminate) male flowers only present the male reproductive organs and hence produce only pollen contrary to (pistillate) female flowers solely producing ovocytes which will become seeds when fecundated. The fact of being androecious for a plant is called androecy.

By "plant with an androecious tendency" is meant in the sense of the present invention a heterozygous plant for the allele mutated according to the invention, carrying more male flowers than the same monoecious or andromonoecious wild plant, without the mutated allele according to the invention.

According to a preferred embodiment, the plant of the invention presents moreover at least one first character of interest like higher yield, lower water consumption or still earlier flowering.

By "character of interest" is meant in the sense of the present invention a character expressed by a plant and which confers it specific properties with respect to the other plants which do not express this character. Preferably, to suit the needs of the present invention, a character of interest is a character of agronomic interest which may be qualitative or quantitative.

The characters of interest in the sense of the present invention may be for example larger and/or more pieces of fruit, higher yield, lesser water consumption, earlier flowering, resistance to certain pathogens, whether of viral, bacterial or fungal nature or still resistance to hydric stress.

By way of example of characters of interest, as alleles involved in the resistance to certain pathogens, whether of viral, bacterial or fungal nature, the following may be quoted: the allele Vat, which confers resistance to the aphid *Aphis gossypii*, the allele Pm-W, which confers resistance to the oidium *Podosphaera xanthi*, the recessive allele nsv, which corresponds to a single mutation in the initiation factor of translation eIF4E, the allele Cys which confers resistance to the cucurbit yellow stuning virus, the alleles Fom1, Fom 2 and Fom 1.2 which confer resistance to *Fusarium oxysporum*, or still the alleles gf, Or and wf which respectively contribute to the colour of the flesh of the green, orange and white melon, as quoted in the publication *Cucurbit Genetics Cooperative Report* 28-29: 142-163 (2005-2006).

The notions of "resistance", "immunity" and "sensitivity" are defined by the ISF (International Seed Federation).

Thus by "Resistance" is meant the capacity of a plant or of a variety to restrict the growth and the development of a pathogen or of a determined pest and/or the damages caused, in comparison with sensitive varieties and under similar environmental and pressure conditions of this pathogen or of this pest. The resistant plants or varieties can express a few symptoms of the disease or a few damages in case of high pressure of the pathogen or of the pest.

The ISF distinguishes two levels of resistance i.e. standard or high resistance (HR*) and intermediate or moderate resistance (IR*).

By "standard or high resistance (HR*)" is meant the capacity of a plant or of a variety to strongly restrict the growth and the development of a determined pathogen or of a determined pest under normal pressure conditions thereof, in comparison with sensitive varieties. These plants or varieties may, however, express symptoms or damages in case of high pressure of this pathogen or of this pest.

By "intermediate or moderate resistance (IR*)" or still by "partial resistance" is meant the capacity of a plant or of a variety to strongly restrict the growth and the development of a determined pathogen or of a determined pest, but which can express more symptoms or damages in comparison with high/standard resistance varieties. The intermediate resistant plants or varieties will show less severe symptoms or damages than those observed on sensitive varieties, under similar, environmental and/or pressure conditions of the pathogen or of the pest.

By "immunity" is meant the fact of not being subjected to the attack or to the infection by a given pest or a given pathogen.

By "sensitivity" is meant the incapacity of a plant or of a variety to restrict the growth and the development of a determined pathogen or of a determined pest.

According to a preferred embodiment, the plant of the invention is characterised in that it is obtained by genetic engineering techniques.

By "genetic engineering" is meant in the sense of the present invention all the techniques for manipulating the genome of a living being so as to modify its genotype and consequently its phenotype.

In a preferred manner, the androecious plant according to the invention is characterised in that the method of obtaining said plant is a mutagenesis inducing one or several mutations in the nucleotide sequence of the wild allele, causing reduced transforming activity of the methionine S-adenosyl into aminocyclopropane carboxylate, whereas said reduced activity is smaller by at least 50%, preferably at least 75% or 90%, still even more preferably by at least 95% or 99% with respect to the wild 1-aminocyclopropane-1-carboxylate synthase 8 and in a particularly preferred manner, the activity becoming nil.

Another object of the invention concerns a seed whose germination leads to a plant according to the invention.

By "seed" is meant in the sense of the present invention an organ, obtained by the development and the mutation of the ovum after fecundation, whereas said organ contains the embryo and necessary nutritive reserves for its development during its germination.

By "germination" is meant in the sense of the present invention the phenomenon of passing from the embryo to the mature seed, from a slowed down life condition to an active growth condition, by using the reserves contained in the seed, until the plantlet obtained is autotrophic.

The man of the art will be able, in the light of his general knowledge, to determine the optimum conditions for the germination of said seeds and the cultivation of the plantlets obtained.

Another object of the invention concerns a use of a plant according to the invention as a pollinator.

The term "pollinator(s)", in the sense of the present invention, refers to a plant used as a pollen giver, which pollen is used for pollinating female flowers. The term "pollinator" in the sense of the present invention is synonym of the term "pollinating plant". The use as a pollinator of the homozygous plant for the mutated allele as defined in the present invention and hence androecious enables the production of hybrid or still triploid seeds and plants. Besides, the absence of female reproductive organs facilitates the experimentations for the selection and the improvement of plants.

The use of heterozygous plants for the mutated allele as defined in the present invention, which plant has an androecious tendency and enables to produce hybrid or still triploid seeds and plants.

Moreover, the androecious plants producing more male flowers for a longer period, and these male flowers producing more pollen, the use of androecious plants enables to mitigate the effects of desynchronisation of male and female flowerings.

Besides, the mutated allele according to the invention may be used in combination with genes governing the architecture of the plant and especially the positioning of the flowers to optimise their arrangement on the plant and hence the dispersion of pollen and the quality of pollination.

Finally, the use of plants according to the invention enables to increase the yield of the fruit produced on a production plot. Indeed, the plants according producing more pollen than usual pollinating plants, the producer may reduce the number of male pollinating plants, increase the number of female plants and hence to increase the number of pieces of fruit harvested on the production plot.

Preferably, the use of a plant, as defined in the present invention, as a pollinator aims at obtaining hybrid plants and seeds of hybrid plants, of seeds of triploid plant and of plants producing seedless fruit derived therefrom, for example in the production of triploid water melons.

In the latter case, the pollinating plants according to the invention may be used for instance to pollinate plants of tetraploid water melons, thereby producing triploid seeds. These triploid seeds will be planted to give triploid plants, whose flowers will have to be pollinated, for example by pollinating plants according to the invention, so as to produce seedless fruit, appreciated by consumers.

By "hybrids" is meant in the sense of the present invention any plant belonging to the Cucurbitaceae family derived from the crossing of two genetically different plants, preferably, both plants are two plants of genetically different bloodlines.

Another object of the invention concerns an isolated polypeptide corresponding to a variant of a reference 1-aminocyclopropane-1-carboxylate (ACS8), of a plant of the Cucurbitaceae family, which 1-aminocyclopropane-1-carboxylate synthase 8 has a transforming activity of methionine S-adenosyl into aminocyclopropane carboxylate and which said variant has a lower activity of at least 50%, preferably at least 75% or 90%, still more preferably 95% or 99% with respect to said reference 1-aminocyclopropane-1-carboxylate synthase 8 and particularly preferably, said variant has a nil activity.

The term "isolated" in the sense of the present invention designates a biological material which has been removed from its original environment (the environment in which it is located naturally). For instance, a polypeptide present in a natural state in a plant is not isolated. The same polypeptide, separate from the other adjacent polypeptides within the cell in which it is naturally present, is isolated.

Preferably, the polypeptide of the invention presents at least 80% identity with the reference polypeptide sequence or a fragment thereof, more preferably at least 85% or 90% identity, and in a particularly preferable way at least 95% identity with that sequence.

Otherwise, the polypeptide of the invention may be a fragment of the reference polypeptide. Said fragment can be obtained by a nonsense mutation on the nucleotide sequence causing the apparition of a codon STOP in this nucleotide sequence or by an offsetting mutation, which may in particular offset the reading frame and reveal a codon STOP in the nucleic acid sequence.

By "identity percentage between two polypeptide sequences" is meant the percentage of identical amino acids, between two sequences to be compared, obtained with the best possible alignment of said sequences. This percentage is purely statistical and the differences between both sequences are distributed randomly over the whole length of the amino acid sequences.

By "best possible alignment and optimum alignment" is meant the alignment enabling to obtain the highest identity percentage. The sequence comparison between two amino acid sequences are usually realised by comparing said sequences once they have been aligned in the best possible manner. The comparison is then conducted on comparison segments so as to identify and compare similarity regions.

The best possible alignment to make a comparison can be carried out by using the global homology algorithm developed by Smith and Waterman (Ad. App. Math., vol. 2, p. 482, 1981), by using the local homology algorithm developed by Neddleman and Wunsch (J. Mol. Biol., vol. 48, p. 443, 1970), by using the similarity method developed by Pearson and Lipman (Proc. Natl. Acd. Sci. USA, vol. 85, p: 2444, 1988), by using computer programmes based on such algorithms (GAP, BESTFIT, BLAST P, BLAST N, FASTA, TFASTA, Genetics Computer Group, 575 Science Dr., Madison, Wis. USA), by using the multiple alignment algorithms MUSCLE (Edgar, Robert C., Nucleic Acids Research, vol. 32, p: 1792, 2004). To obtain the best possible alignment, we shall use preferably the programme BLAST with the matrix BLOSUM 62 or the matrix PAM 30. The identity percentage is determined by comparing both optimally aligned sequences, said sequences may include additions or deletions with respect to the reference sequence so as to obtain the best possible alignment between both sequences. The identity percentage is calculated by determining the number of identical positions between both sequences, by dividing the number obtained by the total number of compared positions and by multiplying the result obtained by 100 to obtain the identity percentage between both these sequences.

The terms "amino acid" and "amino acids" in the sense of the present invention correspond to any amino acid present naturally or to their residues. The amino acids can be identified either by their single-letter abbreviation or their three-letter abbreviation. (Asp D aspartic acid; Ile I isoleucine; Thr T threonine; Leu L leucine; Ser S serine; Tyr Y tyrosine; Glu E glutamic acid; Phe F phenylalanine; Pro P proline; His H histidine; Gly G glycine; Lys K lysine; Ala A alanine; Arg R arginine; Cys C cysteine; Trp W tryptophane; Val V valine; Gln Q glutamine; Met M methionine; Asn N asparagine). According to the present invention, the natural amino acids can be replaced with chemically modified amino acids.

The term "mutation", in the sense of the present invention, refers to a permanent change in the sequence of the genetic material of a plant cell belonging to the Cucurbitaceae family. Such a mutation may correspond in particular to a substitution, a deletion or still an insertion. By "nonsense mutation" is meant in the sense of the present invention the substitution in a gene sequence, of a nucleotide with another nucleotide causing the apparition of a codon STOP.

By "offsetting mutation" is meant in the sense of the present invention the insertion or the deletion in the genomic sequence of a gene, of one or several nucleotides offsetting the reading frame, which could lead to the apparition of a codon STOP.

Preferably, for the *Cucumis sativus* species, the isolated polypeptide corresponding to a variant of a reference 1-aminocyclopropane-1-carboxylate synthase 8(ACS8), having a lower activity by at least 50% with respect to said reference 1-aminocyclopropane-1-carboxylate synthase 8, comprises a sequence with at least 90%, preferably 95% and still more preferably 98% identity with:
the sequence SEQ ID No 6 or variants or fragments thereof, wherein the amino acid at the position 152 and the following ones are deleted, with respect to the sequence SEQ ID No 3, or
the sequence SEQ ID No 9 or variants or fragments thereof, wherein the amino acid at the position 58 and the following ones are deleted, with respect to the sequence SEQ ID No 3.

Preferably, for the *Cucumis melo* species, the isolated polypeptide corresponding to a variant of a reference 1-aminocyclopropane-1-carboxylate synthase 8 (ACS8), having a lower activity by at least 50% with respect to said reference 1-aminocyclopropane-1-carboxylate synthase 8, comprises a sequence with at least 90%, preferably 95% and still more preferably 98% identity with:
the sequence SEQ ID No 15 or variants or fragments thereof, wherein the amino acid at the position 45 is a phenylalanine with respect to the sequence SEQ ID No 12, or
the sequence SEQ ID No 18 or variants or fragments thereof, wherein the amino acid at the position 295 is a phenylalanine with respect to the sequence SEQ ID No 12.

Another object of the invention concerns an encoding polynucleotide for the polypeptide according to the invention.

The polynucleotide according to the invention may be non-encoding if it comprises a mutation causing the disappearance of the initiation codon of the reference polynucleotide.

A homozygous plant of the Cucurbitaceae family for an allele of ACS8 corresponding to said polynucleotide is androecious, i.e. it contains only male flowers.

By "homozygous plant" is meant in the sense of the present invention a plant possessing two encoding polynucleotides for the non-encoding or encoding 1-aminocyclopropane-1-carboxylate synthase 8 (ACS8) for a polypeptide corresponding to a variant of the reference ACS8, at a rate of one copy of said polynucleotide per chromosome of the pair of chromosomes.

A heterozygous plant of the Cucurbitaceae for the mutated allele according to the invention presents a delayed apparition of the female flowers with respect to the male flowers compared to the wild plants having male flowers. Consequently, the heterozygous plants for the mutated allele according to the invention include more male flowers than the wild plants.

By "heterozygous plant" is meant in the sense of the present invention a plant having a single encoding polynucleotide for the polypeptide of the present invention.

By "polynucleotide" is meant in the sense of the present invention a single-stranded nucleotide chain or its complementary or a double-stranded nucleotide chain which may be of DNA or RNA type. Preferably, the polynucleotides of the invention are of DNA, in particular double-stranded DNA.

For the purpose of the present description, the expression "nucleic acid sequence" can be employed to designate indifferently a polynucleotide or a nucleic acid. The expression "nucleic acid sequence" includes the genetic material properly speaking and is hence not restricted to the information concerning its sequence.

The term "nucleic acid sequence" refers to a DNA sequence (for example cDNA (complementary DNA) or genomic or synthetic DNA) or to an RNA sequence (for example a messenger RNA or still synthetic RNA), as well as to DNA or RNA analogs containing analogs of non-natural nucleotides, non-natural internucleotide links or still both of them. Preferably, said nucleotide sequence is a DNA sequence. The nucleotide sequences may exhibit any topological conformation, such as linear or circular.

The term "nucleotide" both designates the natural nucleotides (Adenine: A, Thymine: T, Guanine: G, Cytosine: C) as well as modified nucleotides comprising at least one modification such as (i) an analog of purine, (ii) an analog of pyrimidine, or (iii) an analog sugar, whereas such modified nucleotides are described for example in the application PCT No WO 95/04064.

Preferably, for the *Cucumis sativus* species, the encoding polynucleotide for the polypeptide of the invention comprises a sequence having at least 90%, preferably 95% and still more preferably 98% identity with
the sequence SEQ ID No 5 or variants or fragments thereof, wherein the nucleotide at the position 394 is deleted with respect to the sequence SEQ ID No 2, or
the sequence SEQ ID No 8 or variants or fragments thereof, wherein the nucleotide at the position 173 is an adenine, with respect to the sequence SEQ ID No 2.

Preferably, for the *Cucumis meso* species, the encoding polynucleotide for the polypeptide of the invention comprises a sequence having at least 90%, preferably 95% and still more preferably 98% identity with the sequence SEQ ID No 14 or variants or fragments thereof, wherein the nucleotide at the position 133 is deleted with respect to the sequence SEQ ID No 11, or the sequence SEQ ID No 17 or variants or fragments thereof, wherein the nucleotide at the position 884 is a thymine, with respect to the sequence SEQ ID No 11.

Another object of the invention concerns a cell derived from a plant as defined in the present invention.

Said plant cell comprises the polypeptide of the invention or the encoding polynucleotide for said polypeptide.

By "plant cell" is meant in the sense of the present invention, the protoplasts, the gametes producing cells and the cells regenerating complete plants. The term "plant cell" also refers, without restrictions, to the cells obtained or isolated from: seeds, suspended cultures, embryos, meristems, leaves, roots, shoots, gametophytes, sporophytes, pollen and microspores. A "plant cell" may refer to a single cell or a population of cells. A population of plant cells can be pure, i.e. composed of a single cell type, or composed of different cell types. A plant cell in the sense of the present invention can be isolated or comprised in a plant tissue, a plant organ or a plant regardless of its development stage.

Another object of the invention concerns a method of identifying a plant having an encoding nucleic acid sequence for the polypeptide according to the invention and comprising the steps of:
  a) analysing a sample comprising cells of a plant of the Cucurbitaceae family or extracts thereof so as to identify whether said plant comprises an encoding nucleic acid sequence for the polypeptide according to the invention; and
  b) identifying a plant comprising such a nucleic acid sequence.

The analysis step a) can be carried out by methods well known to the man of the art.

These methods can be direct methods for detecting the nucleic acid sequence selected in the group comprising, but without limitation thereto, polymerisation chain reaction (PCR), in situ hybridisation, Northern blot, Southern blot, sequencing, the KEYPOINT™ technique or still the TILLING.

The TILLING process is well known to the man of the art; it is described in particular by Mc CALLUM et al. (2000, *Plant Physiology, Vol.* 123: 439-442).

These methods can also be indirect methods based on the detection of the polypeptide encoded by said nucleic acid sequence and selected among the group comprising, but without limitation thereto, activity assessment of said polypeptide, Western blot, proteomic mass spectrometry or the iTRAQ method.

The identification step b) can be carried out simply by the man of the art in the light of his general knowledge.

This step may include in particular a step of cultivating the plants identified at step a) as including the nucleic acid sequence of the invention.

In a preferred embodiment, the identification process according to the invention is characterised in that said plant of the Cucurbitaceae family presents moreover at least one first character of interest and in that it comprises moreover, possibly, a step b') of selecting a plant still containing said at least first character of interest. In a preferred embodiment, the method according to the invention is characterised in that it comprises a prior step of mutagenesis of a plant or of a seed of a plant of the Cucurbitaceae family. This step may in particular enable to obtain a collection of mutant plants.

The mutagenesis techniques used for the needs of the present invention should enable to induce mutations in the genome of the plant cells. Such mutagenesis techniques are well known to the man of the art and include in particular UV, X-ray or gamma mutagenesis, Mutagenesis targeted by the KEYBASE™ technique or still chemical mutagenesis, for example ethylmethanesulfonate (EMS; see in particular the method described by KOORNBEEF et al., *Mutat. Res.*, Vol. 93: 109-123, 1982), meganucleases (endodesoxyribonucleases), zinc finger nucleases, ribozymes.

By way of example, the identification of androecious plants can take place as follows: seeds of the Cucurbitaceae family are exposed to a mutagenic agent. The plants derived from these mutated seeds are then self-fecundated so as to obtain a collection of mutant plants.

Then, the DNA of each plant of the previously generated collection is extracted and the nucleic acid sequence of the encoding allele for the ACS8 is amplified to look for the presence of mutation(s) with respect to the sequence of the encoding allele for the non-mutated ACS8. The mutated plants in the sequence of the encoding allele for the ACS8 are selected.

DNA "pools" are then carried out by mixing the DNA extracted from several plants of the collection generated previously, which enables to reduce the number of mutation detection steps. The targeted sequences are amplified by PCR by using the appropriate nucleic primers. The amplicons thus obtained are heated, then cooled down so as to generate DNA heteroduplexes between the DNA of a non-mutated plant on the nucleic acid sequence of the encoding allele for the ACS8 and the DNA of a mutated plant on the nucleic acid sequence of the encoding allele for the ACS8. The heteroduplexes are incubated in the presence of a cutting endonuclease at the mismatches, before denaturation and separation. The separate DNA strands thus obtained are subjected to the mutation detection step, by electrophoresis or still by HPLC under denaturing conditions (DHPLC) described for example by M C CALLUM et al. (2000, *Plant Physiol.*, Vol. 123: 439-442).

Finally, the mutated plants in the sequence of the encoding allele for the ACS8 and which are androecious are selected.

In a preferred embodiment, the method of the invention is characterised in that it aims moreover at selecting an androecious plant and in that it also comprises the steps of:
  c) crossing plants comprising an encoding nucleic acid sequence for a polypeptide according to the invention and as identified at step b); and
  d) selecting a homozygous plant for said nucleic acid sequence.

Advantageously, the method according to the invention moreover includes the steps of:
  e) crossing a plant having at least one first character of interest obtained at step d) with a plant of the Cucurbitaceae family having at least one second character of interest; and
  f) selecting a plant having at least first and second characters of interest.

More in detail, the crossing step e) includes a step of harvesting the pollen from the plant having at least one first character of interest, a step of contacting said pollen with the female organs of the female flowers or hermaphrodite flowers, which have been previously manually, chemically or genetically emasculated, male sterile flowers or any plant presenting functional female organs and non-functional male organs, of plants having at least one second character of interest, for obtaining seeds and, finally a step of cultivating the plant seeds previously obtained.

In a preferred embodiment, the method according to the invention is characterised in that said plant of the Cucurbitaceae family having at least one second character of interest is gynoecious or male sterile.

A method of obtaining gynoecious plants may be as described for instance in the application PCT No WO 2010/012948. A method of obtaining hermaphrodite plants may be as described for instance in the application PCT No WO 2007/125264.

By "gynoecious plant" is meant in the sense of the present invention a plant carrying only female flowers. Said (pistillate) female flowers have only female reproductive organs and hence only produce ovocytes which will become seeds after fecundation, contrary to (staminate) male flowers which only produce pollen. The fact for a plant of being gynoecious is called gynoecy.

By "hermaphrodite plant" is meant in the sense of the present invention plants whose flowers carry both male reproductive organs and female reproductive organs.

By "sterile male plant" is meant in the sense of the present invention a hermaphrodite plant deprived of male reproductive organs or deprived of male reproductive organs capable of producing pollen and/or viable pollen by manual, chemical or genetic emasculation.

In a preferred embodiment, the method according to the invention is characterised in that it aims moreover at producing a plant seed, preferably hybrid, diploid or triploid, and in that it also comprises the steps of:
  g) planting a field alternately with the androecious plants and/or the plants with an androecious tendency and gynoecious and/or sterile male plants as defined previously;
  h) harvesting the fruit of the gynoecious and/or sterile male plants obtained after pollination; and
  i) extracting said seeds from said fruit.

Another object of the invention concerns a seed, preferably hybrid, diploid or triploid, of a plant obtained according to the method of producing a plant seed, preferably hybrid, diploid or triploid, according to the invention.

Another object of the invention concerns a method of producing an androecious plant of the Cucurbitaceae family, said method comprising the steps of:
  a) obtaining a plant of the Cucurbitaceae family, preferably selected among the group comprising the *Cucumis*, *Citrullus*, *Cucurbita*, *Luffa*, *Momordica* and *Lagenaria* genera,
  b) inhibiting the 1-aminocyclopropane-1-carboxylate synthase 8 (ACS8) of said plant.

According to the invention, the 1-aminocyclopropane-1-carboxylate synthase 8 (ACS8) of said plant is characterised by a nucleic acid sequence having at least 75%, particularly at least 80%, more particularly at least 90%, preferably at least 95%, more preferably at least 98%, even more preferably at least 99% identity with any of the sequences SEQ ID 10, 19, 22, 25, 28 and 31.

In an embodiment of the invention, the step b) of inhibiting the 1-aminocyclopropane-1-carboxylate synthase 8 (ACS8) enables to obtain an activity smaller by at least 50% preferably at least 75% or 90%, still more preferably at least 95% or 99% with respect to said 1-aminocyclopropane-1-carboxylate synthase 8 of said plant before inhibition.

The inhibition of 1-aminocyclopropane-1-carboxylate synthase 8 (ACS8) should be understood in the broadest sense and comprises the inhibition of the expression, by using inhibitors of the expression, of 1-aminocyclopropane-1-carboxylate synthase 8 (ACS8) or the inhibition of the activity, by using inhibitors of the activity, of 1-aminocyclopropane-1-carboxylate synthase 8 (ACS8). The use of inhibitors of the expression or the activity of 1-aminocyclopropane-1-carboxylate synthase 8 (ACS8).

By inhibitor of the expression is meant a natural or synthetic compound with the capacity of inhibiting, or of diminishing significantly, the expression of a gene, at the different expression levels thereof, especially transcription and translation.

Examples of inhibitors of the expression comprise in particular interfering RNAs (siRNA, miRNA, shRNA) and anti-sense oligonucleotides (comprising antisense DNAs and RNAs), acting by linking to the gene of interest, and thereby preventing the expression of the gene by blocking the translation or by increasing the degradation of the messenger RNAs. The antisense oligonucleotides are generally 15 bases in length and are complementary to the RNA or the DNA of the gene of interest. They may be synthesised and used by methods well known to the man of the art. The interfering RNAs are also selected and used by methods well known to the man of the art.

The ribozymes can also be used for inhibiting the expression of a gene of interest. The ribozymes are indeed molecules of enzymatic RNA capable of catalysing the cleavage of RNA. The action mechanism of ribozyme involves a specific sequence hybridisation of the ribozyme molecule at the RNA target sequence which is complementary thereto, followed by an endonucleolytic cleavage. The techniques for obtaining and using such ribozymes are well known to the man of the art. The sites of ribozyme-specific cleavages in any potential RNA target are initially identified by studying the target RNA, the sites comprising typically the sequences GUA, GUU and GUC. Once identified, the small RNA sequences, generally 15 to 20 ribonucleotides in length and corresponding to the region of the target RNA comprising the site of cleavage, can be assessed in terms of prediction of their structural characteristics (equivalent to a secondary structure) which may render the oligonucleotide unsuitable.

The antisense oligonucleotides, interfering RNAs and ribozymes usable in the context of the invention can be prepared by methods well known to the man of the art. They include chemical synthesis techniques. Alternately, antisense RNA molecules and interfering RNAs can be generated by in vitro or in vivo transcription of encoding DNA sequences for such RNA molecules. These DNA sequences can be incorporated for a large number of vectors which comprise or may comprise suitable RNA polymerase promoters such as T7 or SP6 polymerase promoters. Numerous modifications well known to the man of the art can be made to the oligonucleotides of the invention, to increase their cellular stability and their half-life.

The antisense oligonucleotides, the interfering RNAs and the ribozymes of the invention can be delivered in vivo on their own or in combination with a vector.

By inhibitor of the activity is meant a compound, natural or not, having the capacity of reducing or suppressing the activity of a protein.

The activity inhibitors of the invention can be chemical, natural or synthesis compounds, but also biological compounds, inhibiting or reducing significantly the activity of a protein of interest. Such compounds can be molecules binding to said protein (for example, but not necessarily, on its active site), and thereby blocking its activity. The compounds can also inhibit the activity of the protein by acting upon an actor of the signalling pathway of said protein of interest.

The activity inhibitor of the invention can also be an aptamer. Aptamers are molecules offering an alternative to antibodies in terms of molecular recognition. These are oligonucleotide or oligopeptide sequences with the capacity to recognise virtually any class of target molecules with high affinity and specificity. Such ligands can be isolated and modified by techniques well known to the man of the art.

Naturally, another object of the invention also relates to a plant or a seed obtained by this method according to the invention.

Preferably, said androecious plant of the Cucurbitaceae family is not derived from the *Cucumis sativus* species.

Another object of the invention concerns a method of producing an androecious plant or with an androecious tendency, of the Cucurbitaceae family, said method comprising the steps of:
  a) obtaining a plant of the Cucurbitaceae family, which plant is selected among the group comprising the *Cucumis, Citrullus, Cucurbita, Luffa, Momordica* and *Lagenaria* genera,
  b) highlighting the presence of at least one allele of the non-encoding or encoding 1-aminocyclopropane-1-carboxylate synthase 8 (ACS8) for a polypeptide corresponding to a variant of the reference ACS8 for said plant,
  c) studying the transforming activity of the methionine S-adenosyl into aminocyclopropane carboxylate of the 1-aminocyclopropane-1-carboxylate synthase 8 encoded by said allele,
  d) selecting a plant having a transforming activity of the methionine S-adenosyl into aminocyclopropane carboxylate and which said variant has a lower activity by at least 50%, preferably at least 75% or 90%, still more preferably 95% or 99% with respect to said reference 1-aminocyclopropane-1-carboxylate synthase 8 and particularly preferably, said variant has a nil activity.

According to the invention, said variant of the reference 1-aminocyclopropane-1-carboxylate synthase 8 (ACS8) put in evidence at step b) is characterised by a nucleic acid sequence having at least 75%, particularly at least 80%, more particularly at least 90%, preferably at least 95%, more preferably at least 98%, even more preferably at least 99% identity with any of the sequences SEQ ID 10, 19, 22, 25, 28, 31 and 33, but not perfectly identical therewith.

Naturally, another object of the invention also relates to a plant or a seed obtained by this method according to the invention.

Preferably, said androecious plant of the Cucurbitaceae family is not derived from the *Cucumis sativus* species.

Another object of the invention concerns a method of selecting a plant having at least two characters of interest, said method comprising the following steps:
  a) analysing a sample comprising cells of a plant of the Cucurbitaceae family having a first character of interest or extracts thereof so as to identify whether said plant comprises an encoding nucleic acid sequence for the polypeptide according to the invention; and
  b) identifying a plant including such a nucleic acid sequence and still having said first character of interest,
  c) crossing plants comprising an encoding nucleic acid sequence for a polypeptide according to the invention and still having said first character of interest as identified at step b),
  d) selecting a plant still having said first character of interest and homozygous for said nucleic acid sequence,
  e) crossing a plant having at least one first character of interest obtained at step d) with a plant of the Cucurbitaceae family having at least one second character of interest; and
  f) selecting a plant having at least first and second characters of interest.

Naturally, another object of the invention also relates to a plant or a seed obtained by this method according to the invention.

Preferably, said plant of the Cucurbitaceae family of step d) is not derived from the *Cucumis sativus* species.

Another object of the invention concerns besides a propagation method of an androecious homozygous plant of the invention, comprising the steps of:
  a) treating homozygous androecious plants for the ACS8 mutated allele of the invention, with a compound enabling to induce an increased intracellular concentration in ethylene, for generating female flowers,
  b) self-pollination of the plants obtained at step a), and
  c) harvesting the seeds.

The man of the art is capable of identifying simply, and in the light of his general knowledge, compounds enabling to induce an increased intracellular ethylene concentration. Ethephon and ACC can be quoted as examples of such compounds.

Ethephon or ethrel is a vegetable growth factor well known to the man of the art.

The ACC or 1-aminocyclopropane-1-carboxylic acid plays an important role in ethylene biosynthesis and is synthesised by the ACC synthetase enzyme from methionine, than converted into ethylene by the ACC oxydase.

The homozygous androecious plants for the ACS8 mutated allele of the invention comprise a polypeptide or polynucleotide of the invention.

The seeds obtained by such a method are de facto androecious, and comprise a polypeptide or polynucleotide of the invention.

Naturally, another object of the invention also relates to a plant or a seed obtained by this method according to the invention.

Preferably, said androecious plant of the Cucurbitaceae family is not derived from the *Cucumis sativus* species.

Another object of the invention also concerns a method of producing a plant seed, preferably hybrid, diploid or triploid plant seed, comprising the steps of:
  a. seeding a field alternately with the androecious plants and/or with an androecious tendency of the invention comprising a first character of interest and gynoecious and/or sterile male plants as defined in the present invention comprising a second character of interest;
  b. harvesting the fruit of the plants obtained after pollination, and
  c. extracting said seeds from said fruit.

According to the invention, an androecious plant or with an androecious tendency of the invention carries an ACS8 mutated allele of the invention or is heterozygous for the mutated allele of the non-encoding or encoding 1-aminocyclopropane-1-carboxylate synthase 8 (AQCS8) for a variant of the reference ACS8. Said plant with an androecious tendency carries more male flowers than the same monoecious or andromonoecious wild plant which does not have said mutated allele.

Preferably, said seed is homozygous for the ACS8 mutated allele of the invention, and thus comprises a polypeptide and/or a polynucleotide of the invention.

Preferably, said seed of the Cucurbitaceae family is not derived from the *Cucumis sativus* species.

Another object of the invention concerns a plant, of the Cucurbitaceae family, selected among the group comprising the *Cucumis, Citrullus, Cucurbita, Luffa, Momordica* and *Lagenaria* genera, with the exclusion of the *Cucumis sativus* species, and characterised in that it is androecious.

Another object of the invention concerns a use, for the identification of androecious plants of the Cucurbitaceae family, of probes or primers enabling to detect the polynucleotide according to the invention in a sample comprising cells of such a plant or extracts thereof.

By "probe" is meant in the sense of the present invention a nucleic acid sequence having hybridisation specificity under set conditions to form a hybridisation complex with a target nucleic acid sequence and emitting a signal when hybridising the probe on the target nucleic acid sequence.

By "primer" is meant in the sense of the present invention a nucleic acid sequence which can be an initial point for the synthesis of a nucleic acid sequence, along the strand of a complementary nucleic acid, under conditions catalysing said synthesis. Such conditions include the presence of the four nucleotide bases and of a polymerisation agent such as a DNA polymerase, in a buffer solution and with a suitable temperature.

The man of the art will be capable to simply identify such probes or primers in the light of his general knowledge. Such probes or primers advantageously correspond to polynucleotides of at least 15 nucleic acids, preferably of at least 20 nucleic acids.

Advantageously still, these probes or primers exhibit a sequence which is identical or complementary to an encoding sequence for an ACS8 of a plant belonging to the Cucurbitaceae family. By way of example of such sequences, the sequences SEQ ID No 4 and SEQ ID No 7 of *Cucumis sativus* and SEQ ID No 13 and SEQ ID No 16 of *Cucumis melo* can be quoted.

Another object of the invention concerns a use, for the selection of androecious plants of the Cucurbitaceae family, of antibodies enabling to detect the polypeptide according to the invention in a sample comprising cells of such a plant or extracts thereof.

By "antibodies" is meant in the sense of the present invention, especially polyclonal or monoclonal antibodies or fragments (for instance the $F(ab)'_2$, $F(ab)$ fragments) recognising the polypeptide or the target polypeptide fragment according to the invention.

Table of sequences

| SEQ ID No | Type | Designation |
|---|---|---|
| 1 | Polynucleotide | Genomic sequence of wild ACS8 of *Cucumis sativus* |
| 2 | Polynucleotide | Encoding sequence of wild ACS8 of *Cucumis sativus* |
| 3 | Polypeptide | Protein sequence of wild ACS8 of *Cucumis sativus* |
| 4 | Polynucleotide | Genomic sequence of the deleted variant of ACS8 of *Cucumis sativus* |
| 5 | Polynucleotide | Encoding sequence of the deleted variant of ACS8 of *Cucumis sativus* |
| 6 | Polypeptide | Protein sequence of the deleted variant of ACS8 of *Cucumis sativus* |
| 7 | Polynucleotide | Genomic sequence of the variant W58→STOP of ACS8 of *Cucumis sativus* |
| 8 | Polynucleotide | Encoding sequence of the variant W58→STOP of ACS8 of *Cucumis sativus* |
| 9 | Polypeptide | Protein sequence of ACS8 of the variant W58->STOP of *Cucumis sativus* |
| 10 | Polynucleotide | Genomic sequence of wild ACS8 of *Cucumis melo* |
| 11 | Polynucleotide | Encoding sequence of wild ACS8 of *Cucumis melo* |
| 12 | Polypeptide | Protein sequence of wild ACS8 of *Cucumis melo* |
| 13 | Polynucleotide | Genomic sequence of the variant L45→F of ACS8 of *Cucumis melo* |
| 14 | Polynucleotide | Encoding sequence of the variant L45→F of ACS8 of *Cucumis melo* |
| 15 | Polypeptide | Protein sequence of ACS8 of the variant L45→F of *Cucumis melo* |
| 16 | Polynucleotide | Genomic sequence of the variant S295→F of ACS8 of *Cucumis melo* |
| 17 | Polynucleotide | Encoding sequence of the variant S295→F of ACS8 of *Cucumis melo* |
| 18 | Polypeptide | Protein sequence of ACS8 of the variant S295→F of *Cucumis melo* |
| 19 | Polynucleotide | Genomic sequence of wild ACS8 of *Citrullus lanatus* |
| 20 | Polynucleotide | Encoding sequence of wild ACS8 of *Citrullus lanatus* |
| 21 | Polypeptide | Protein sequence of wild ACS8 of *Citrullus lanatus* |
| 22 | Polynucleotide | Genomic sequence of wild ACS8 of *Luffa acutangula* |
| 23 | Polynucleotide | Encoding sequence of wild ACS8 of *Luffa acutangula* |
| 24 | Polypeptide | Protein sequence of wild ACS8 of *Luffa acutangula* |
| 25 | Polynucleotide | Genomic sequence of wild ACS8 of *Lagenaria siceraria* |
| 26 | Polynucleotide | Encoding sequence of wild ACS8 of *Lagenaria siceraria* |
| 27 | Polypeptide | Protein sequence of wild ACS8 of *Lagenaria siceraria* |
| 28 | Polynucleotide | Genomic sequence of wild ACS8 of *Momordica charentia* |
| 29 | Polynucleotide | Encoding sequence of wild ACS8 of *Momordica charentia* |
| 30 | Polypeptide | Protein sequence of wild ACS8 of *Momordica charentia* |
| 31 | Polynucleotide | Incomplete genomic sequence of wild ACS8 of *Cucurbita pepo* |
| 32 | Polynucleotide | Incomplete encoding sequence of wild ACS8 of *Cucurbita pepo* |
| 33 | Polypeptide | Incomplete protein sequence of wild ACS8 of *Cucurbita pepo* |
| 34 | Polynucleotide | Genomic sequence of wild ACS8 of *Citrullus lanatus* |
| 35 | Polynucleotide | Encoding sequence of wild ACS8 of *Citrullus lanatus* |
| 36 | Polypeptide | Protein sequence of wild ACS8 of *Citrullus lanatus* |

The following examples are provided by way of illustration and are not intended to limit the scope of the present invention.

EXAMPLES

Example 1

Mapped Population

To map genetically the gene A responsible for androecy in the cucumber (*Cucumis sativus*), a species for which androecy exists in natural state, we have exploited a segregated population for this phenotype. As the gene is a recessive gene, we have exploited a backcross (BC) population. To do so, plants of monoecious cucumber (male flowers and female flowers on the same plant) have been crossed with androecious plants (only male flowers). The descendance F1 has been re-crossed with the androecious parent to produce the backcross descendance 1 (BC1) (FIG. 1). The descendance BC1 will be 50% monoecious and 50% androecious. 260 plants derived from the BC1 have been phenotyped and have served for extracting genomic DNA.

Example 2

Primary Location of the Region Containing the Gene of Androecy

The aim of this step is the identification of molecular markers which specifically segregate with androecy. To identify these markers, the idea is to group the DNA of the monoecious BC1 individuals and the DNA of the androecious BC1 individuals. This technique is called BSA, Bulk Segregant Analysis, (Michelmore, R. W. et al. Identification of markers linked to disease-resistance genes by bulked segregant analysis: A rapid method to detect markers in specific genomic regions by using segregating populations. Proc. Natl. Acad. Sci. USA. 88: 9828-9832, 1991) or mixed segregation analysis. According to this strategy, we have translated 4 bulks of 7 different individuals (2 bulks of DNA of androecious plants and 2 bulks of DNA of monoecious plants). The bulks of DNA derived from plans of the same sex type have given the same results and consequently the search for molecular marker AFLP (Vos, P. et al. AFLP: a new technique for DNA fingerprinting. Nucleic Acids Research. Vo 121, 21: 4407-4414, 1995) was realised with only 2 bulks of DNA (1 androecious bulk, 1 monoecious bulk).

Figure 2:
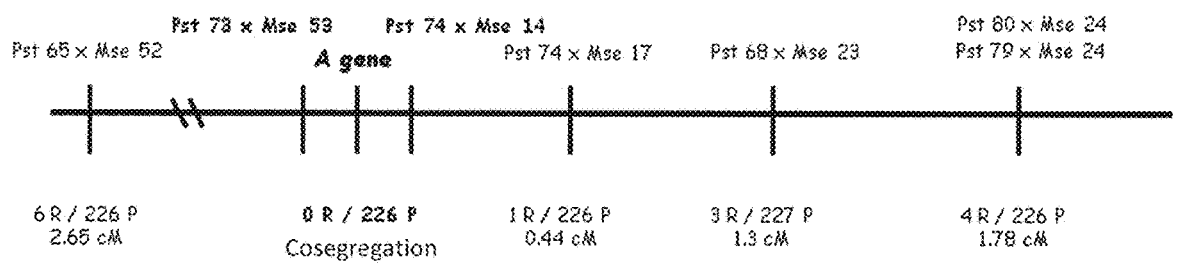
FIG. 2 represents the genetic map of the locus of androecy in the cucumber made from a population of 230 individuals.

After screening all the 1024 possible AFLP combinations, we have obtained 52 polymorphous AFLP combinations between both (monoecious and androecious) bulks. The 52 AFLP have been used to genotype 50 individual plants. Upon completion of this work, we have identified 7 AFLP markers which co-segregate or which are highly bonded to the androecious phenotype. The 7 AFLP markers have been used to build the first intent genetic map of the locus Androecy (FIG. 2).

Example 3

Anchoring the AFLP Markers on the Cucumber Genome Sequence and Development of the Fine Genetic Map of the Region of the Gene of Androecy Anchoring the AFLP markers was made easier by the availability of the sequence of cucumber genome. The positioning of the AFLP markers has enabled to measure the physical distance between both AFLP markers (Pst65× Mse52 and Pst74×Mse17) enclosing the locus Androecy. This distance is 781 kilobases (kb) and contains 62 genes.

So as to reduce the physical interval as far as possible, we have developed new molecular markers every 50 kb in a range of 1 Megabase (Mb) centred on the locus Androecy. All these markers are developed in intergenic regions. Thanks to this approach, we have identified the genetic markers A82×A87 and A48×A50 which have enabled us to screen a BC1 population of 1717 individuals so as to find new genetic recombinants in the region of the locus Androecy.

Further to the identification of the new genetic markers and the search for recombinants, we have developed the fine genetic map of the locus Androecy.

This approach has not enabled us to identify directly the gene responsible for androecy. However, the recombinants delineate the genetic interval responsible for the androecy at 53.5 kb contained 7 predicted genes.

Example 4

Identification of the Candidate Gene of Polymorphism Responsible for Androecy and Association Genetics Among the 7 genes in the genetic confidence interval, the gene CsACS8 encodes for an ACC synthase, the key enzyme of the ethylene biosynthesis route. From a genetic viewpoint, the physical distance between this gene CsACS8 and the other AFLP markers (FIG. 2) is compatible with the relationship between the physical distance and the genetic distance described for the cucumber. Moreover, in Cucurbitaceae like cucumber and melon, ethylene has been described as the vegetable hormone with the major effect on the determination of the floral sex type. In view of these different points, the gene CsACS8 is considered as a very good candidate gene.

Figure 3:
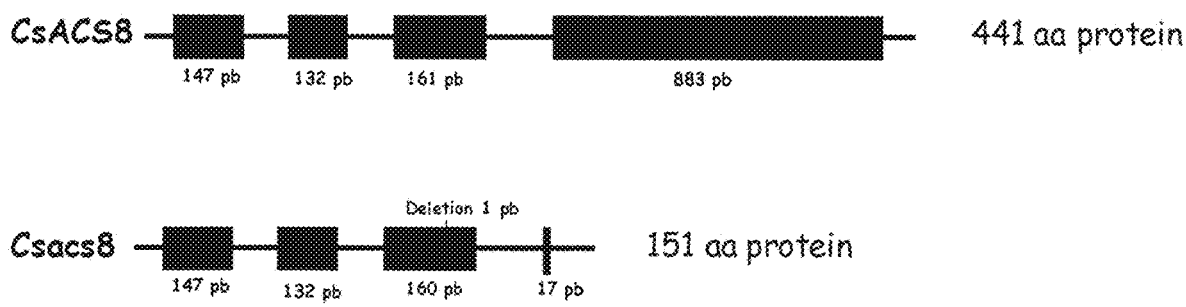
FIG. 3 represents the genetic structure of both alleles of the gene of androecy in the cucumber. i.e. the dominant allele whose nucleic acid sequence encodes for a polypeptide sequence of wild ACS8 and the mutated recessive allele whose nucleic acid sequence encodes for a polypeptide sequence of truncated ACS8.

To check whether the gene CsACS8 can be the gene responsible for Androecy, we have sequenced this gene in the parents of the mapping population, the androecious parent and the monoecious parent. In the monoecious parent carrying the dominant allele A, the gene CsACS8, composed of 4 exons and 3 introns, encodes for a protein of 441 amino acids. In the androecious parent, the gene CsACS8 exhibits a deletion of a base in the $3^{rd}$ exon of the gene. This deletion changes the protein reading frame and causes the apparition of the codon STOP 20 amino acids after the deletion, thereby leading to a protein of 151 amino acids (FIG. 3).

To consolidate the genetic mapping data, we have conducted an association genetic study between the androecious phenotype and the deletion of 1 pair of bases in the gene CsACS8 over 28 cucumber accessions (2 androecious, 2 gynoecious, 6 andromonoecious, 9 monoecious and 9 hermaphrodite). The sequencing of CsACS8 in these 28 accessions has put in evidence a perfect association between the deletion of 1 pair of bases and the androecy, in other words the 2 androecious accessions carry the deletion whereas all the other accessions regardless of the sex type do not exhibit the deletion.

Example 5

Functional Validation of the Gene CsACS8

In the laboratory, we have a TILLING cucumber population (mutant EMS) of 3360 families realised from the variety Beit alpha. This variety of cucumber is monoecious and hence carries male and female flowers. On this TILLING population, we have sought mutations induced by the EMS on the whole encoding sequence of the gene CsACS8.

In the TILLING Beit Alpha population, we have identified 9 mutations: 7 silent ones and 1 change in amino acid P437L and 1 mutant STOP. The mutant homozygous plants for the mutation STOP only develop male flowers and have hence become androecious. Phenotyping of the mutants P437L is underway.

In order to study whether the gene CsACS8 also controls the androecy in other Cucurbitaceae, we have studied its role in sex determinism in melon, a cucurbitacea for which the existence of androecy in natural state has never been reported. To do so, we have identified the homologous sequence of the gene CsACS8 in melon: CmACS8.

When exploiting our melon TILLING population, we identified 12 mutated families in the gene CmACS8. Among these 12 mutations, 5 are intronic, 4 silent and 3 drive a change in amino acid (L45F, G72E and S295F). The mutation G72E affects an amino acid situated in a variable protein region whereas the mutations L45F and S295F affect amino acids in protein regions highly preserved in all the plants.

Since the melon accession used as a parent of the TILLING population is monoecious (male flower and female flower on the same plant), the three families of melon carrying amino acid change mutations in the gene CmACS8 were phenotyped for their sex type. The homozygous plants for the mutation G72E carry male and female flowers (monoecious plant) and consequently have not been affected in their sex determinism. On the contrary, the mutant homozygous plants L45F and S295F only produce male flowers and have hence become androecious. Thanks to these mutants, we have managed to create a sex type, androecy, which has never been described in melon.

These results validate the fact that the gene of androecy identified in cucumber also controls androecy in melon, another cucurbitacea.

Example 6

Functional Validation of the Gene CsACS8 in the Zucchini (*Cucurbita pepo*)

In order to study whether the gene ACS8 also controls the androecy in other Cucurbitaceae than cucumber and melon, we have studied its role in sex determinism in zucchini, a cucurbitacea for which the existence of androecy in natural state has never been reported. To do so, we have sought to identify the homologous sequence of the gene CsACS8 of the cucumber and CmACS8 of the melon in the zucchini: CpACS8.

When exploiting our zucchini TILLING population, we have sought to identify mutated plants in the gene CpACS8 which are androecious. Finer analyses are in progress to determine the nature of the mutation responsible for androecy in zucchinis.

Example 7

Functional Validation of the Gene CsACS8 in the Water Melon (*Citrullus lanatus*)

In order to study whether the gene ACS8 also controls the androecy in other Cucurbitaceae than cucumber and melon, we have studied its role in sex determinism in water melon, a cucurbitacea for which the existence of androecy in natural state has never been reported. To do so, we have sought to identify the homologous sequence of the gene CsACS8 of the cucumber and CmACS8 of the melon in the water melon: ClACS8.

When exploiting our water melon TILLING population, we have sought to identify mutated plants in the gene ClACS8 which are androecious. Finer analyses are in progress to determine the nature of the mutation responsible for androecy in water melons.

Example 8

Dosing the Transforming Activity of Methionine S-adenosyl into Aminocyclopropane Carboxylate by the 1-aminocyclopropane-1-carboxylate Synthase 8 (ACS8)

The enzymatic activity of the ACS8 is measured in vitro by following, by 265-nm spectrophotometry, the formation of 5'-methylthioadenosine (MTA) after involving methionine S-adenosyl, deaminase and different PLP concentrations (pyridoxal 5'-phosphate).

Bacterial Strains, Plasmids and Reaction Products:

The bacterial strain *Escherichia coli* BL21(DE3)pLYSS is used for the expression of the enzyme. The cloning vector used is the plasmid pET15b (NOVAGEN) which carries the promoter T7 and comprises resistance to ampicillin. S-adenosyl Methionine (SAM), Pyridoxal 5'phosphate (PLP) and 5'Adenylic Acid Deaminase of Aspergillus (deaminase) are available from the SIGMA company.

Expression of the 1-aminocyclopropane-1-carboxylate Synthase 8 (ACS8) in *E. coli*

The reference ACS8 derived from SEQ ID No 3 and No 12 or the recombinant ACS8 derived from SEQ ID No 6, No 9, No 15 and No 18 have been cloned in the vector Pet15b, which vector has been used to transform the bacteria *Escherichia coli* BL21(DE3)pLYSS according to the conditions supplied by the manufacturer.

These bacteria *Escherichia coli* BL21(DE3)pLYSS transformed with the construct carrying the 1-aminocyclopropane-1-carboxylate synthase 8 (ACS8) are incubated in 25 ml LURIA-BERTANI medium (tryptone 10 g/L, yeast extract 5 g/L, NaCl 10 g/L) added with ampicillin and chloramphenicol (50 μg/ml each) overnight at 37° C. This pre-culture is used to inoculate 2 litres of the same medium added with ampicillin (50 μg/ml) and the cells are cultivated at 37° C. in a stirred incubator (180 rpm) up to 0.6 Optical Density (DO=600 nm). IPTG is added (0.5 mM) so as to induce the protein expression during a new 5-hour culture phase at 25° C. Cells are centrifuged and kept overnight at −45° C. Cells are then re-suspended in 15 ml TrisNaCl (50 mM, pH7.9, 500 mM, respectively) then subjected to ice sonication in the presence of a protease inhibitor (phenylmethanesulfonyl fluoride), leupeptin, pepstatin and aprotinin, 10 µg/ml each). The cellular debris are removed during a new centrifugation step at 13,000 g during 15 minutes and the supernatant is immediately used for enzymatic purification.

Purification of ACS8

Due to the presence of a Histidine tag associated with each of the ACS8, the latter are purified by using a nickel column (Ni-IDA 15 ml) previously balanced with TRIS at PH8 and NaCl (500 mM). After passing the solution containing recombinant ACS8 to be purified, the column is then washed with TRIS at PH8 (50 mM) and NaCl (500 mM) added with imidazole (10 mM) until no protein can be detected at the output any longer. The ACS8 are then eluted with the same buffer solution added with imidazole at 100 mM, then dialysed (KPhos 50 mM á PH8.5) before concentration (MILLIPORE AMICON ULTRA DEVICE, 5000 MWC0). The concentrated fraction (20 mg/ml) of ACS8 is aliquoted and stored with glycerol at −45° C. The purification of protein is followed by capillary electrophoresis (EXPERION DEVICE—BIO RAD) with a PRO260 chip.

Purification of Adenosine Deaminase:

5 g lyophilised deaminase powder (SIGMA) are resuspended in a beaker with 90 ml cold water to which 47 ml acetone are added. The solution is stirred 5 minutes at 4° C., then centrifuged 1 minute at 2000 g. The cap is mixed with 33 ml water, stirred 5 minutes and again centrifuged, 5 minutes at 2000 g. The cap is thrown away and the supernatant is added with 10 ml ethanol. The solution is stirred 5 minutes at 4° C., then centrifuged. The supernatant is added with 20 ml ethanol. The solution is softly stirred for 3 hours at 4° C. The solution is centrifuged 5 minutes at 7000 g and the cap is re-suspended with 6 ml water. The solution is dialysed (sodium acetate solution, 5 mM, pH5.3) for at least 24 hours, then concentrated (MILLIPORE AMICON ULTRA DEVICE, 5000MWC0) and finally aliquoted in glycerol (5 mg/ml) before storage at −45° C.

Enzymatic Activity:

The enzymatic activity of the different ACS8 is determined by following the formation of 5'-methylthioadenosine (MTA) at 265 nm in differential spectroscopy on a spectrophotometer Uvikon 940 (BIOTEK-KONTRON): the measurements are realised during the incubation of methionine S-adenosyl (60 µg) in 100 mM KPhos buffer (0.2 ml, PH8.5) and deaminase (8 µg) in the presence or the absence of pyridoxal 5'-phosphate (0 to 300 µM). The measurements are made in quartz tubs of the spectrophotometer for 3 minutes at 25° C. after the addition of purified enzyme (1 to 2 µg). The conversion of MTA into inosine derivative is followed at 265 nm. And the specific activity is expressed in MTA nanomoles formed per minute and per protein mg. More particularly, the activity of the sequences SEQ ID No 6, No 9 (*Cucumis sativus*), No 15 and No 18 (*Cucumis melo*) is expressed in activity percentage with respect to the sequences SEQ ID No 3 (*Cucumis sativus*) and SEQ ID No 12 (*Cucumis melo*). An identical protocol is used for determining the Vm and Km.

Example 9

Study of the Apparition Kinetics of Male and Female Flowers for Plants Carrying the Mutation of the Invention The inventors have studied the apparition kinetics of the male flowers for the mutant S295F (10 homozygous plants and 10 heterozygous plants for the mutation) and for the mutant L45F (10 homozygous plants and 10 heterozygous plants for the mutation). A plant is used as a control (10 plants):

The plants are transplanted into a field, then each morning, they are examined so as to count the number of new male flowers:

|  | Mutant S295F Homozygous | Mutant S295F Heterozygous | Mutant L45F Homozygous | Mutant L45F Heterozygous | Control |
|---|---|---|---|---|---|
| Day 1 | 0.2 | 0.4 | 0 | 0.1 | 0 |
| Day 2 | 0 | 0.3 | 0.8 | 0.3 | 0.9 |
| Day 3 | 1.0 | 0.3 | 0.8 | 1.0 | 0.7 |
| Day 4 | 0.7 | 1.2 | 1.3 | 1.6 | 0.9 |
| Day 5 | 1.9 | 1.6 | 0.9 | 0.9 | 1.6 |
| Day 6 | 2.2 | 2.6 | 1.8 | 1.3 | 1.4 |
| Day 7 | 0.7 | 0.7 | 1.4 | 0.9 | 0.7 |
| Day 8 | 0.9 | 0.5 | 0.9 | 0.6 | 0.4 |
| Day 9 | 1.9 | 1.1 | 1.6 | 1.6 | 1.6 |
| Day 10 | 1.6 | 1.6 | 1.6 | 1.7 | 1.0 |
| Day 11 | 1.4 | 1.9 | 1.6 | 1.7 | 0.7 |
| Day 12 | 1.9 | 0.8 | 1.0 | 1.7 | 1.1 |
| Day 13 | 1.6 | 1.4 | 0.7 | 1.3 | 1.9 |
| Day 14 | 0.9 | 0.9 | 0.8 | 1.2 | 0.6 |
| Day 15 | 1.1 | 1.5 | 2.1 | 2.3 | 1.1 |
| Day 16 | 5.3 | 3.3 | 5.2 | 4.8 | 3.3 |
| Day 17 | 3.3 | 4.7 | 3.8 | 4.4 | 2.1 |
| Day 18 | 4.7 | 4.4 | 4.2 | 4.1 | 3.0 |
| Day 19 | 5.0 | 4.5 | 6.1 | 4.6 | 4.0 |
| Day 20 | 7.9 | 6.5 | 7.7 | 7.1 | 3.3 |
| Day 21 | 12.0 | 7.7 | 10.0 | 9.6 | 3.9 |
| Day 22 | 6.4 | 4.4 | 9.5 | 9.4 | 4.0 |
| Day 23 | 11.1 | 8.0 | 9.5 | 10.5 | 3.1 |
| Day 24 | 14.3 | 10.9 | 11.8 | 11.9 | 4.6 |
| Day 25 | 13.8 | 7.5 | 12.4 | 13.8 | 4.6 |
| Day 26 | 14.1 | 8.9 | 22.8 | 13.5 | 6.0 |
| Day 27 | 19.4 | 10.5 | 18.5 | 13.4 | 7.0 |
| Day 28 | 30.0 | 19.3 | 25.6 | 24.0 | 12.7 |
| Day 29 | 41.1 | 22.3 | 34.6 | 28.8 | 11.7 |
| Day 30 | 35.4 | 25.5 | 31.5 | 29.9 | 14.3 |
| Day 31 | 45.6 | 25.8 | 45.0 | 30.3 | 15.9 |
| Day 32 | 43.2 | 25.6 | 41.3 | 35.4 | 17.0 |
| Day 33 | 57.2 | 27.4 | 46.4 | 34.6 | 17.3 |
| Day 34 | 70.4 | 34.2 | 54.7 | 41.8 | 25.1 |
| Day 35 | 64.7 | 33.6 | 52.2 | 37.9 | 19.4 |
| Day 36 | 71.8 | 31.2 | 60.6 | 39.7 | 18.6 |

Figure 4:
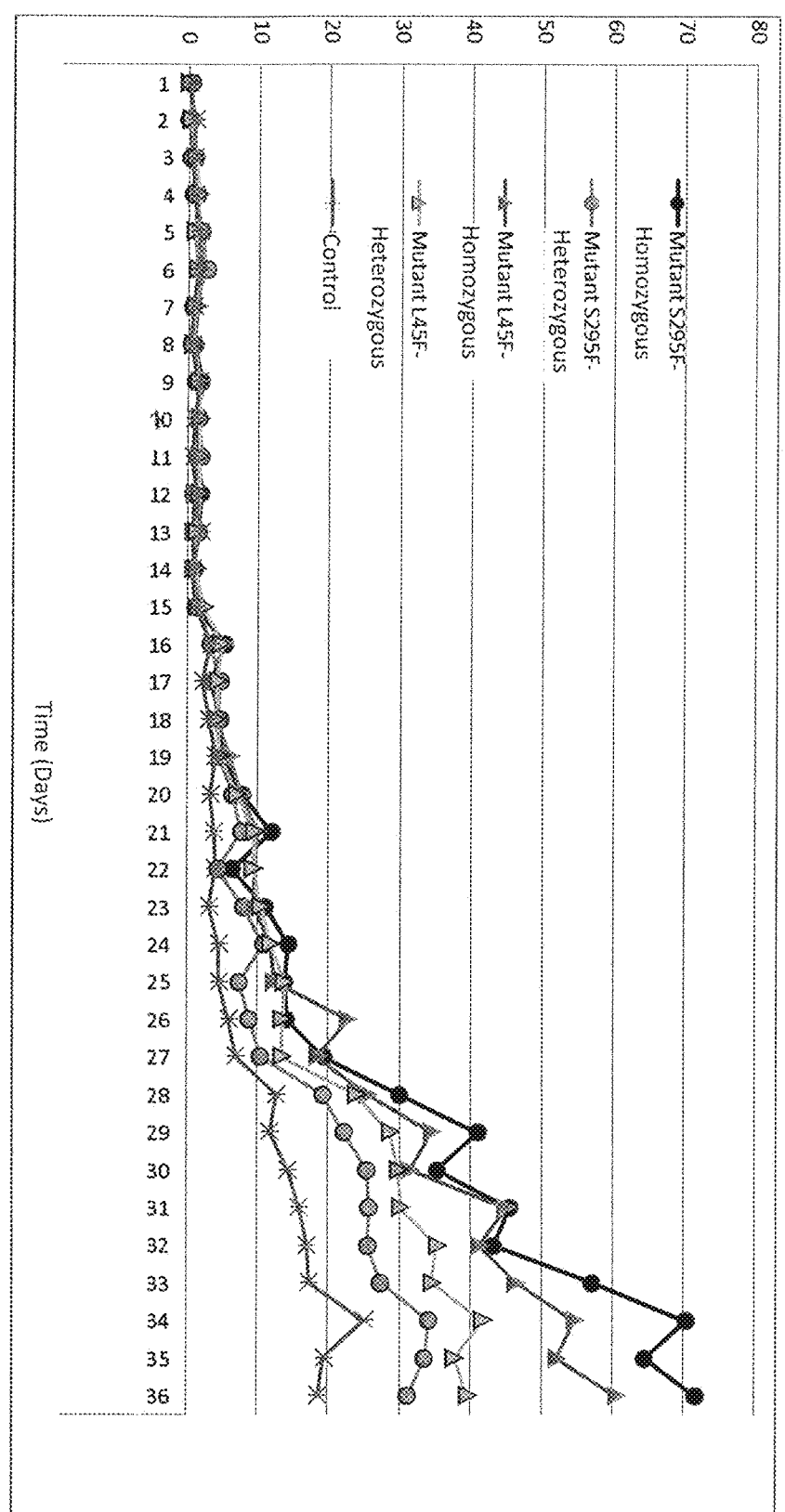
FIG. 4 represents the apparition kinetics of male flowers, in connection with the experimentations conducted at example 9.

The results obtained are presented in FIG. 4.

Both mutations S295F and L45F, when present as homozygous and heterozygous in plants promote the apparition of male flowers.

The inventors have besides studied the apparition kinetics of the female flowers for the mutant S295F (10 homozygous plants for the mutation) and for the mutant L45F (10 homozygous plants for the mutation). A plant is used as a control (10 plants):

|  | Homozygous mutant S295F | Homozygous mutant L45F | Control |
|---|---|---|---|
| Day 1 | 0 | 0 | 0 |
| Day 2 | 0 | 0 | 0 |
| Day 3 | 0 | 0 | 0 |
| Day 4 | 0 | 0 | 0 |
| Day 5 | 0 | 0 | 0 |
| Day 6 | 0 | 0 | 0 |
| Day 7 | 0 | 0 | 0 |
| Day 8 | 0 | 0 | 0 |
| Day 9 | 0 | 0 | 0 |
| Day 10 | 0 | 0 | 0 |
| Day 11 | 0 | 0 | 0 |
| Day 12 | 0 | 0 | 0 |
| Day 13 | 0 | 0 | 0 |
| Day 14 | 0 | 0 | 0 |
| Day 15 | 0 | 0 | 0 |
| Day 16 | 0 | 0 | 0 |
| Day 17 | 0 | 0 | 0.2 |
| Day 18 | 0 | 0 | 0.2 |
| Day 19 | 0 | 0 | 0 |
| Day 20 | 0 | 0 | 0 |
| Day 21 | 0 | 0 | 0 |
| Day 22 | 0 | 0 | 0 |
| Day 23 | 0 | 0 | 0 |
| Day 24 | 0 | 0 | 0.1 |
| Day 25 | 0 | 0 | 0.2 |
| Day 26 | 0 | 0 | 0.1 |
| Day 27 | 0 | 0 | 0 |
| Day 28 | 0 | 0 | 0.7 |
| Day 29 | 0 | 0 | 0.4 |
| Day 30 | 0 | 0 | 0.4 |
| Day 31 | 0 | 0 | 0.4 |
| Day 32 | 0 | 0 | 0 |
| Day 33 | 0 | 0 | 1.4 |
| Day 34 | 0 | 0 | 4 |
| Day 35 | 0 | 0.1 | 2.4 |
| Day 36 | 0 | 0.1 | 1 |

Figure 5:
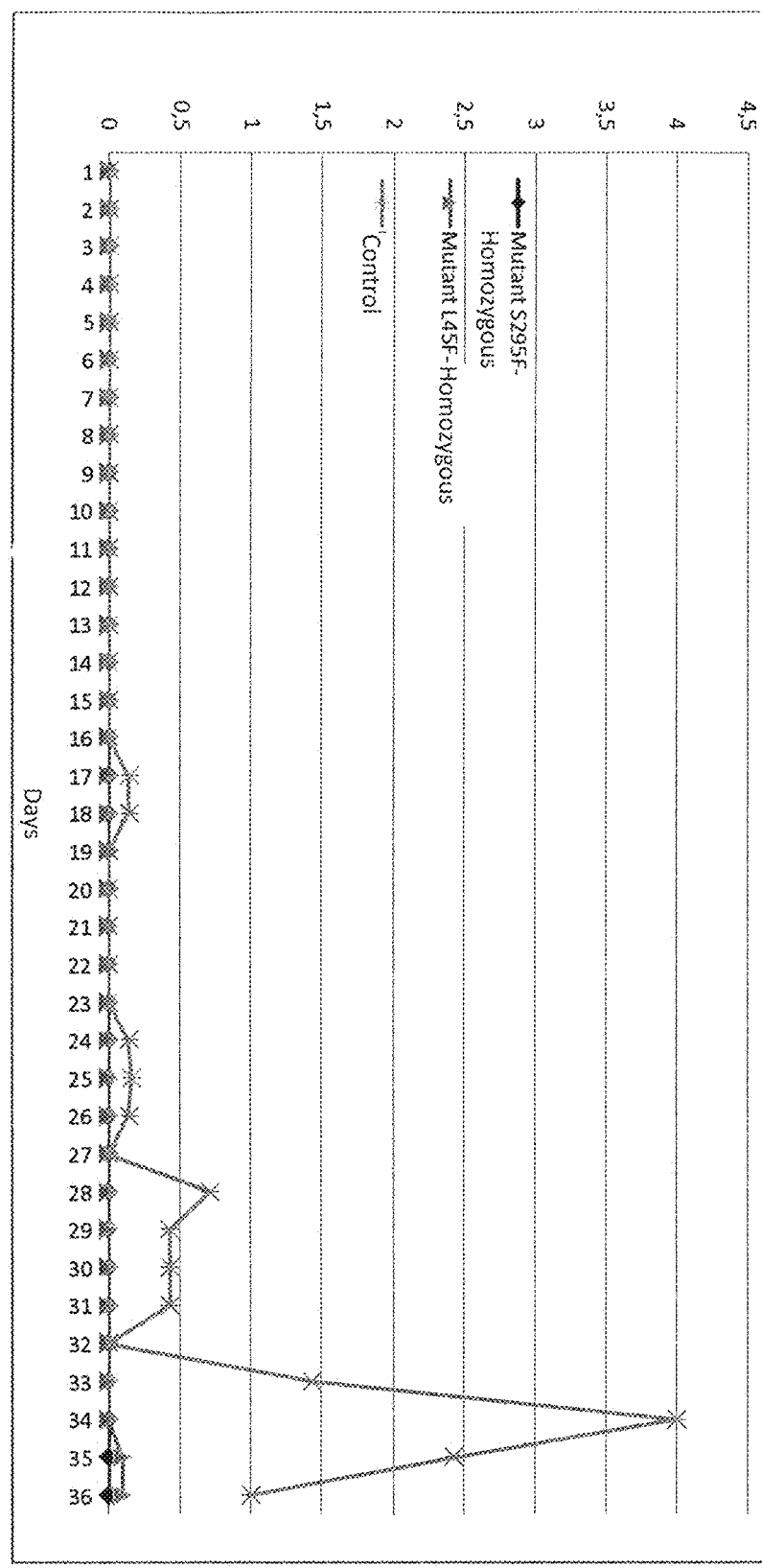
FIG. 5 represents the apparition kinetics of female flowers, in connection with the experimentations conducted at example 9.

The results obtained are presented in FIG. 5.

Both mutations S295F and L45F, when present as homozygous in plants prevent the apparition of female flowers.

Example 10

Heritability of the Trait

The inventors wished to study the transmission of the androecious phenotype from one generation to the other. However, due to the nature of the plants, it is obviously impossible to fecundate an androecious plant with itself or another androecious plant.

The inventors have then treated the plants with ethrel, a growth regulator known for inducing female flowers in cucurbitaceae. The plants thus treated have briefly produced female flowers, sufficiently for them to be fecundated and to produce fruit. The seeds derived from this fruit have been planted to produce plants which phenotype is androecious: the androecious phenotype of the present invention is thus heritable.

Example 11

Determination of the Enzymatic Activity of the Different Isoforms of the Enzyme ACS8

The inventors have determined the biochemical characteristics of the different isoforms of the enzyme ACS8 in the presence of 5 or 100 μm PLP. It should be noted that the concentration of PLP present in the cell would be of the order of 5 μm.

The results obtained are presented in the following table.

|  |  | PLP 100 μm | | PLP 5 μm | |
|---|---|---|---|---|---|
| SEQ ID No | Enzyme | Km (μM) | Vmax (nmol · min$^{-1}$ · mg$^{-1}$) | Km (μM) | Vmax (nmol · min$^{-1}$ · mg$^{-1}$) |
| 3 | CsACS8 | 25 ± 6 | 576 ± 35 | 20 ± 6 | 500 ± 35 |
| 6 | Csacs8 | ND | ND | ND | ND |
| 9 | Csacs8_W58STOP | ND | ND | ND | ND |
| 12 | CmACS8 | 20 ± 5 | 607 ± 55 | 20 ± 5 | 587 ± 51 |
| 15 | Cmacs8_L45F | 25 ± 4 | 60 ± 20 | 23 ± 4 | 75 ± 20 |
| Not listed | Cmacs8_G72E | 15 ± 5 | 600 ± 50 | 17 ± 5 | 575 ± 50 |
| 18 | Cmacs8_S295F | 15 ± 5 | 400 ± 100 | 16 ± 5 | 275 ± 100 |

The results show that the activity of the wild isoform of ACS8 in the cucumber (SEQ ID no 3) and in the melon (SEQ ID no 12) have a comparable enzymatic activity regardless of the substrate concentrations.

The mutant isoforms of the cucumber, both presenting an offset of the reading frame leading to the expression of a protein of 151 (SEQ ID no 6) or of 57 amino acids (SEQ ID no 9) instead of 440, do not show any enzymatic activity.

The mutant isoforms of the melon, apart from the isoform G72E, conversely exhibit reduced activity with respect to the activity of the wild isoform. More specifically, the isoforms L45F and S295F show a reduction of the order of 90 and 50% respectively of the enzymatic activity with respect to the wild isoform.

Finally, these results demonstrate that an isoform with reduced enzymatic activity by at least 50% with respect to the wild isoform exhibit an androecious phenotype.

The invention claimed is:

1. A method for the production of androecious or of androecious tendency plant of the Cucurbitaceae family selected from the group consisting of *Cucumis, Citrullus, Luffa, Momordica* and *Lagenaria* genera, with the exclusion of the *Cucumis sativus* species, comprising the steps of
   i) exposing seed of the Cucurbitaceae family selected from the group consisting of *Cucumis, Citrullus, Luffa, Momordica* and *Lagenaria* genera, with the exclusion of the *Cucumis sativus* species, to a mutagenic agent, wherein the mutagenic agent induces one or more non-natural mutations in at least one 1-aminocyclopropane-1-carboxylate synthase 8 (ACS8) allele in the genome of the seed, and
   ii) growing a plant from the seed obtained in step i), wherein the plant comprises at least one mutated 1-aminocyclopropane-1-carboxylate synthase 8 (ACS8) allele thus conferring androecy or androecious tendency, wherein the presence of the at least one mutated ACS8 allele is determined by an absence or a reduced enzymatic activity of at least 50% of SEQ ID NO:12, SEQ ID NO:21, SEQ ID NO:24, SEQ ID NO:27, SEQ ID NO:30 or SEQ ID NO:36 compared to a plant of the same species grown from a seed that was not exposed to the mutagenic agent, and wherein the at least one mutated ACS8 allele encodes an ACS8 polypeptide having at least 95% sequence identity with SEQ ID NO:12, SEQ ID NO:21, SEQ ID NO:24, SEQ ID NO:27, SEQ ID NO:30 or SEQ ID NO:36.

2. The method of claim 1, further comprising self-fecundating of the plant of the Cucurbitaceae family grown from the mutated seed to obtain a collection of mutant plants.

3. The method of claim 1, further comprising selecting the plant of the Cucurbitaceae family having the at least one mutated ACS8 allele encoding an ACS8 polypeptide having at least 95% sequence identity with SEQ ID NO:12, SEQ ID NO:21, SEQ ID NO:24, SEQ ID NO:27, SEQ ID NO:30 or SEQ ID NO:36 and which are androecious or of androecious tendency.

4. The method of claim 3, further comprising crossing two selected plants of the Cucurbitaceae family selected from the group consisting of *Cucumis, Citrullus, Luffa, Momordica* and *Lagenaria* genera, with the exclusion of the *Cucumis sativus* species, having the at least one mutated ACS8 allele encoding an ACS8 polypeptide having at least 95% sequence identity with SEQ ID NO:12, SEQ ID NO:21, SEQ ID NO:24, SEQ ID NO:27, SEQ ID NO:30 or SEQ ID NO:36, and further selecting a plant homozygous for the mutated ACS8 allele that can be used as a pollinator.

5. The method of claim 1, wherein the mutagenic agent is ethylmethanesulfone (EMS).

6. The method of claim 4, wherein the two crossed plants of the Cucurbitaceae family are from the same species.

\* \* \* \* \*

SEQUENCE LISTING

<160> NUMBER OF SEQ ID NOS: 36

<210> SEQ ID NO 1
<211> LENGTH: 6001
<212> TYPE: DNA
<213> ORGANISM: Cucumis sativus

<400> SEQUENCE: 1

```
tatgttgtcg acgtggatga aactgatatt ctaaaaagaa gtagattaaa atattagaaa      60
atacatctac gaaacgatag tgaaattaca caaggtttgt atatatagaa aaattgaccg     120
catttcattg atgatgatag tttattatta atagatcata ttgtaaatag tattttatga     180
ttttattacc tttgtaattt ttttaaatat ttgtgaacaa aatgtatttg gattagatga     240
atatatatca gtgtttaat gaggcaaatg ctaatattat ggaatgtcca tagtaaatgg      300
atgaggaaat atgatgaatg attatataaa ggaaatataa ttaagaatga attagggttg     360
ttaatttgat ttaggagaaa atggattatt gtaaatgtaa aatgtaaaaa gagaaaatat     420
agttagggaa ggcgacaaga aagaaagaaa gagagaaagg gttgagtgtt aaaaatacac     480
tacgatggac cactctctct tcccttcct ctctcatcat atgacacgtg cctttacctc      540
cttgtttttc aaattttacg gagccattgt cagataccgc gtttcccttc gtggaccacc     600
ccaaacccta attccccaaa ctaacttcac ttcctcgcta atattacttt cattatattt     660
accctcctat tactttaaat aagagaaaag tagaatagta ctaatcataa ctccagaatt     720
atgatctaaa taattctaat cctaattcta gaataataat aactgctaga acaaacatac     780
atgaagtggg ctatttattc ataggatgag atgtaaaggc gtcatttgag tttggatgaa     840
aaggaaatta agagagagag aggagaggag aaagtcaatg ggtaggacgg ttgcgtgtga     900
ttggcatgag ccatcttgtt aaaccatagt gtgtcggtga aatatgtgaa tatgcaaaac     960
catacacgcc ttctcctctc tttacatatt ccatacttct cattaatatc actgcccaac    1020
aaatttatat tctctttcac ttattacttt tacatttttc caactcttcc tattttatt     1080 ttacattttt caaccctttg aatttcaatt tattaactta caaaaccttc acctaactta    1140
aaactccaat tctcaatttt caaaacaaat tgatatgtta tcaactacta cgatgttaaa    1200
agatatattt aaaagagata aaaacaaaaa aattgatttg tttttttttt atatttaaat    1260
ttatagaaaa tgaaaaatta atccaaatta tggctaatac tccacctcac atctatgggc    1320
tttaactttt aagatgaatt ggtgattcac attccacccc acaaattatg taagagaaga    1380
gaagagaaga gaagatagac aaaaggagtt aattggtatg ccaccatgtg gtcttatcaa    1440
tctacaaccc tcatatggca attcagttga ggtttcacga aaaaggaaat tttggaaata    1500
agttttttcc ttggttttct atattattaa tgtcagccat agcaatgctt ttatacgcga    1560
acaatcccta ttttgggata ataaaagtta aagagtgaat ttaaatattg tacccatttc    1620
gtgtgcagtg tacatatggt agacacggga tgaaaacaaa ctattttcat accctcatg     1680
```

```
attcagctac aacttggcat ctgtgttgtt aactagttta ctttctcaca ttgactcttc    1740
tctaacaaat tcaatgggca taaccatcaa aattcattta aatccatgca taatagctat    1800
tacaataaca aatctcaagt ctctataaca gaggttaaca actatgaaaa ttaacttcat    1860
ttattttgtt ccaataatcc aacaattcca accactcaca tcactactaa tttaaaaggt    1920
ttaaacattt tctagttttc caaattcgat tggattgaag ttaattcttt ttactattct    1980
tttattgttt aagttgtgat ttttttgtaa tttcctttta gacttgttaa tgatttgtgt    2040
ttttgttgaa agtttgtatt aaatacccat acatgtttag tattttata tttgaattta     2100 ataagatttt gttgttatta ttatgtttta ttgataagct tcaaaatttt aaactaaaaa    2160
gaaaaatcga aaaataaatc cgacaatgaa tccaactcca actttaagtg tcgggtatag    2220
atttagttta agattttatg tgagtatttt ggttgttcca cgtttgaatt ttcactcgat    2280
tcaaaaatca ctatcaatct agctcaactc aacctagccg acgtacacta ttcgccttta    2340
attttttctt ctcactttc ttactagtca tccttcctgg atttgcattt aaatcttttc     2400
taatttagag tttgaaaagt tgctatcata tatcaacaga atcatttgac ttagagcatc    2460
caaacatata atatgtagtc atgtcttcga ttaaagtata ggaaattatt attataaaaa    2520
aatatcaatt acaggaaaaa gacagagaaa aataaaagag agagaattag ccaataaagt    2580
cactaccagt tgtgttgttt gtgataaaaa ataattaaaa aaaaactctt taatatcatg    2640
caccctaccc ctcttctcct cactatatat atagatatat aaatgtcact ctaaattccc    2700
cacacaaaca cacaaagatt tcaatatcaa tagtcctata ccaaccctaa aatatattcc    2760
tctcctatta tctacctaca tattactgta cactcacata tgatggcatc cttgtcttct    2820
aaagctagcc atgattctca tggacaaaat tcttcctact tctttggatt gcaagagtat    2880
gagaaggacc cttatcaccc tattcaaaac ccctcgggaa ttatacaaat gggtcttgcc    2940
gaaaacaagg taattcttga atgtaattaa gttggactac aaccattatt gttccttttg    3000
tagtttaact acacatggtc gaatcatttg ttatcaaatg acattgtagt cggttgaaat    3060
atattgagta attaagtaag aaaaagatgt aaacgcggat gcatcaaagt aaaaccaaat    3120
aaaaatatgt tacgtagcaa ttaatttatt taatgaattt tgtaaggttt agttaacggt    3180
ttcttttata tatgcttgtt atgatcacga tgattatgga ttatggatta tggttttgga    3240
ggtagaaaat ttgattgtaa catgtgtatt taaatgggt tttgcaggta tgtcctgacc     3300
ttttggatga gtggatggag aacaatccag atgctttggg attgagaaga aatggagtgt    3360
ctgagtttag agaattagct ctatttcaag actatcatgg cttgccagct tttaaaaagg    3420
tacctagcct acaaccctag ttttattcat aaagggctct tcaaattttc tttttctttc    3480
ttttttattt atttgtttac tattgaagta atataaataa taataatag gtgttggttg      3540 aatcaatgga agagatacga ggaaacaaaa tgaaatttga aaagaacaaa ctggtgctca    3600
ctgctggtgc aactgctgcc aatgaaatca taatatcctg tcttgccgat cccggtgaag    3660
ccttccttgt tcccactcct tactatccag ggtatctaaa ttcaatcatc ttcctatgtt    3720
taagttttct ctcttttctta tcacttggtt tgtaagaata tacgtatata tactgcaggt    3780
ttgacaggga cttaaaatgg cgaactggag tgcaaataat tccaattcat tgttcgagtt    3840
caaacggttt tcgaatcacc gaagtgtcga tggaggaagc catggagcaa gcccaatcat    3900
tgaatttacg agtcaagggg attatgatta cgaacccatc taacccattg ggcaccacat    3960
tgagccagaa agagctcaac tcagtggtgg attttgctac aaccaacgca atccacatcg    4020
tgagcgacga gatatattct gccacagttt ttgagcaacc gaatttccga actgtcatgg    4080
```

```
acccgaacct acaaaaactc ccaatttggg atcgaatcca cttggtgtac agcttgtcca    4140
aagatttagg cctacctggg tttcgtgtgg gcatgattta ttcaaacgac ccagcggtag    4200
tggatgcggc tactaaaatg tcgagctttt gcttagtttc ttctcaaaca cagtattttg    4260
tgtcacaaat tgtagggggat gaaaattttc gagggaatta tatgcaggaa atgaagcgga    4320
ggatccggaa gaggagattg atgttggagt cgagtcttcg acagggcggt gttagatgtc    4380
tgaaaggaaa tgcggggttg ttttgttggg tggatatgag gcatcttttg aagtacccga    4440
gtttcgaaga ggaaatggag atttggaaga cgattttgta tgaggttggg attaatatct    4500
cccccggctc atcttttcat tgctctgaac ctggttggtt cagaatgtgc tttgctaata    4560
tggaggagca cactttcaag gaggccatgc atcgtcttaa ggcctttctc aactctacct    4620
catctctcaa cggccatgaa ctctccccca ctaacgtata atatgttatt gatgtagtcc    4680
aattgcaggt agaggattga atcacaactc aatcaaataa ttatattagt tatgttttct    4740
actctatata attttgtact attaagacgt tgtaatataa atatagatcg atccacatag    4800
aatcgatcaa ctttcattcc aattcacctt cttgttgtaa acaaggagtt tgatgtatta    4860
ttggtttggt ttgtaataaa tttaactaaa gcagtaaatt ggaaatttgg ttggattaaa    4920
atttcaaaaa aatcacacaa ataccgatag agaaaataat gttaagatta ctcttgattt    4980
cctactcaat cattagatta atcatacaca ttttggcaa ttctatgaac ataattttag    5040
ctgactacat ctagaaaggc tagagagccg ggatgtccag ttaaccaaat tgatctttat    5100
gtttagagga aaaccatctc aaacatgcaa atcaattaat ctgcatttat tccaatgatt    5160
attgttaagt caaacaatta acttggaatt gcctagttaa gtactcccca aatcaatgct    5220
aatcaatccc aattatgtta atcaaactta ttagattata attgtcaaat caatatacaa    5280
atctaactta acttgcgtta ctcggcgatc taagatttta gcgactatgg actatatccg    5340
gatctatagc aataaattac atatgcttga ttacttatca atgtttctaa atacgctcaa    5400
tcgaattcga taaataagat gacgacaaga atttgatata tcataaaatt aaaatgaaaa    5460
gatttctaat ctcatgagtt tgccaatcaa aatataaacc ttaaattttg aatcatataa    5520
acatcgcacg aaaaacacat gcttttctat cttacggtgt cgtggtgcta gctagtcctc    5580
ctttaaaagt gattctatcc aatgttattt gtattaaatc taattaatta tacataaggg    5640 catttatca agattaaaaa gaatatataa tcgttacatg aaaatatata cattatacag    5700
aataaaacta tgacataaaa ttaaactcct ccgaatgcat tttgaaatct tgttaatatc    5760
tgtaatagaa ttaacatagg cttgggcttg gagtcttaaa tgggctggta ctatccacct    5820
taatgggctg ctttggtttg atcactttaa ttatgggccg tagcttcagt tctttcagga    5880
tcctctcctt ctgaaagtgc tctttagcct tcgacttttg aaagaaagta tattaaaaag    5940
gttttgacat aactttctt attttcattt gctacgtgga gtttgtgttg tatattatgt    6000
t                                                                    6001
```

<210> SEQ ID NO 2
<211> LENGTH: 1323
<212> TYPE: DNA
<213> ORGANISM: Cucumis sativus

<400> SEQUENCE: 2

```
atggcatcct tgtcttctaa agctagccat gattctcatg gacaaaattc ttcctacttc     60
tttggattgc aagagtatga gaaggaccct tatcacccta ttcaaaaccc ctcgggaatt    120
```

```
atacaaatgg gtcttgccga aaacaaggta tgtcctgacc ttttggatga gtggatggag    180
aacaatccag atgctttggg attgagaaga aatggagtgt ctgagtttag agaattagct    240
ctatttcaag actatcatgg cttgccagct tttaaaaagg tgttggttga atcaatggaa    300
gagatacgag gaaacaaaat gaaatttgaa agaacaaac tggtgctcac tgctggtgca     360
actgctgcca atgaaatcat aatatcctgt cttgccgatc ccggtgaagc cttccttgtt    420
cccactcctt actatccagg gtttgacagg gacttaaaat ggcgaactgg agtgcaaata    480
attccaattc attgttcgag ttcaaacggt tttcgaatca ccgaagtgtc gatggaggaa    540
gccatggagc aagcccaatc attgaattta cgagtcaaag ggattatgat tacgaaccca    600
tctaacccat tgggcaccac attgagccag aaagagctca actcagtggt ggattttgct    660
acaaccaacg caatccacat cgtgagcgac gagatatatt ctgccacagt ttttgagcaa    720
ccgaatttcc gaactgtcat ggacccgaac ctacaaaaac tcccaatttg ggatcgaatc    780
cacttggtgt acagcttgtc caaagatcta ggcctacctg ggtttcgtgt gggcatgatt    840
tattcaaacg acccagcggt agtggatgcg gctactaaaa tgtcgagctt ttgcttagtt    900
tcttctcaaa cacagtattt tgtgtcacaa attgtagggg atgaaaattt tcgagggaat    960
tatatgcagg aaatgaagcg gaggatccgg aagaggagat tgatgttgga gtcgagtctt   1020
cgacagggcg tgttagatg tctgaaagga aatgcggggt tgttttgttg ggtggatatg    1080
aggcatcttt tgaagtaccc gagtttcgaa gaggaaatgg agatttggaa gacgattttg    1140
tatgaggttg ggattaatat ctcccccggc tcatcttttc attgctctga acctggttgg   1200
ttcagaatgt gctttgctaa tatggaggag cacactttca aggaggccat gcatcgtctt   1260 aaggccttc tcaactctac ctcatctctc aacggccatg aactctcccc cactaacgta   1320
taa                                                                1323
```

<210> SEQ ID NO 3
<211> LENGTH: 440
<212> TYPE: PRT
<213> ORGANISM: Cucumis sativus

<400> SEQUENCE: 3

Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30

Pro Ile Gln Asn Pro Ser Gly Ile Ile Gln Met Gly Leu Ala Glu Asn
        35                  40                  45

Lys Val Cys Pro Asp Leu Leu Asp Glu Trp Met Glu Asn Asn Pro Asp
    50                  55                  60

Ala Leu Gly Leu Arg Arg Asn Gly Val Ser Glu Phe Arg Glu Leu Ala
65                  70                  75                  80

Leu Phe Gln Asp Tyr His Gly Leu Pro Ala Phe Lys Lys Val Leu Val
                85                  90                  95

Glu Ser Met Glu Glu Ile Arg Gly Asn Lys Met Lys Phe Glu Lys Asn
            100                 105                 110

Lys Leu Val Leu Thr Ala Gly Ala Thr Ala Ala Asn Glu Ile Ile Ile
        115                 120                 125

Ser Cys Leu Ala Asp Pro Gly Glu Ala Phe Leu Val Pro Thr Pro Tyr
    130                 135                 140

Tyr Pro Gly Phe Asp Arg Asp Leu Lys Trp Arg Thr Gly Val Gln Ile
145                 150                 155                 160

```
Ile Pro Ile His Cys Ser Ser Asn Gly Phe Arg Ile Thr Glu Val
            165                 170                 175

Ser Met Glu Glu Ala Met Glu Gln Ala Gln Ser Leu Asn Leu Arg Val
        180                 185                 190

Lys Gly Ile Met Ile Thr Asn Pro Ser Asn Pro Leu Gly Thr Thr Leu
            195                 200                 205

Ser Gln Lys Glu Leu Asn Ser Val Val Asp Phe Ala Thr Thr Asn Ala
        210                 215                 220

Ile His Ile Val Ser Asp Glu Ile Tyr Ser Ala Thr Val Phe Glu Gln
225                 230                 235                 240

Pro Asn Phe Arg Thr Val Met Asp Pro Asn Leu Gln Lys Leu Pro Ile
            245                 250                 255

Trp Asp Arg Ile His Leu Val Tyr Ser Leu Ser Lys Asp Leu Gly Leu
        260                 265                 270

Pro Gly Phe Arg Val Gly Met Ile Tyr Ser Asn Asp Pro Ala Val Val
            275                 280                 285

Asp Ala Ala Thr Lys Met Ser Ser Phe Cys Leu Val Ser Ser Gln Thr
        290                 295                 300

Gln Tyr Phe Val Ser Gln Ile Val Gly Asp Glu Asn Phe Arg Gly Asn
305                 310                 315                 320

Tyr Met Gln Glu Met Lys Arg Arg Ile Arg Lys Arg Leu Met Leu
            325                 330                 335

Glu Ser Ser Leu Arg Gln Gly Gly Val Arg Cys Leu Lys Gly Asn Ala
        340                 345                 350

Gly Leu Phe Cys Trp Val Asp Met Arg His Leu Leu Lys Tyr Pro Ser
            355                 360                 365

Phe Glu Glu Met Glu Ile Trp Lys Thr Ile Leu Tyr Glu Val Gly
        370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Glu Ala
            405                 410                 415

Met His Arg Leu Lys Ala Phe Leu Asn Ser Thr Ser Ser Leu Asn Gly
        420                 425                 430

His Glu Leu Ser Pro Thr Asn Val
            435                 440

<210> SEQ ID NO 4
<211> LENGTH: 6000
<212> TYPE: DNA
<213> ORGANISM: Cucumis sativus

<400> SEQUENCE: 4
tatgttgtcg acgtggatga aactgatatt ctaaaaagaa gtagattaaa atattagaaa      60
atacatctac gaaacgatag tgaaattaca caaggtttgt atatatagaa aaattgaccg     120
catttcattg atgatgatag tttattatta atagatcata ttgtaaatag tattttatga     180
ttttattacc tttgtaattt ttttaaatat ttgtgaacaa aatgtatttg gattagatga     240
atatatatca gtgtttttaat gaggcaaatg ctaatattat ggaatgtcca tagtaaatgg     300
atgaggaaat atgatgaatg attatataaa ggaaatataa ttaagaatga attagggttg     360
ttaatttgat ttaggagaaa atggattatt gtaaatgtaa aatgtaaaaa gagaaaatat     420
agttagggaa ggcgacaaga aagaaagaaa gagagaaagg gttgagtgtt aaaaatacac     480
```

```
tacgatggac cactctctct tccccttcct ctctcatcat atgacacgtg cctttacctc    540
cttgttttc aaattttacg gagccattgt cagataccgc gtttcccttc gtggaccacc    600
ccaaaccta attccccaaa ctaacttcac ttcctcgcta atattacttt cattatattt    660
accctcctat tactttaaat aagagaaaag tagaatagta ctaatcataa ctccagaatt    720
atgatctaaa taattctaat cctaattcta gaataataat aactgctaga acaaacatac    780
atgaagtggg ctatttattc ataggatgag atgtaaaggc gtcatttgag tttggatgaa    840
aaggaaatta agagagagag aggagaggag aaagtcaatg ggtaggacgg ttgcgtgtga    900
ttggcatgag ccatcttgtt aaaccatagt gtgtcggtga aatatgtgaa tatgcaaaac    960
catacacgcc ttctcctctc tttacatatt ccatacttct cattaatatc actgcccaac   1020
aaatttatat tctcttttcac ttattacttt tacattttc caactcttcc tatttttatt   1080
ttacatttt caacccttg aatttcaatt tattaactta caaaaccttc acctaactta   1140
aaactccaat tctcaatttt caaaacaaat tgatatgtta tcaactacta cgatgttaaa   1200
agatatattt aaaagagata aaaacaaaaa aattgatttg ttttttttt atatttaaat   1260
ttatagaaaa tgaaaaatta atccaaatta tggctaatac tccacctcac atctatgggc   1320
tttaacttt aagatgaatt ggtgattcac attccacccc acaaattatg taagagaaga   1380
gaagagaaga gaagatagac aaaaggagtt aattggtatg ccaccatgtg gtcttatcaa   1440
tctacaaccc tcatatggca attcagttga ggttcacga aaaaggaaat tttgaaata   1500
agttttttcc ttggttttct atattattaa tgtcagccat agcaatgctt ttatacgcga   1560
acaatcccta ttttgggata ataaaagtta aagagtgaat ttaaatattg tacccatttc   1620
gtgtgcagtg tacatatggt agacacggga tgaaaacaaa ctattttcat accccctcatg   1680
attcagctac aacttggcat ctgtgttgtt aactagttta cttctcaca ttgactcttc   1740
tctaacaaat tcaatgggca taaccatcaa aattcattta aatccatgca taatagctat   1800
tacaataaca aatctcaagt ctctataaca gaggttaaca actatgaaaa ttaacttcat   1860
ttattttgtt ccaataatcc aacaattcca accactcaca tcactactaa tttaaaaggt   1920
ttaaacattt tctagttttc caaattcgat tggattgaag ttaattcttt ttactattct   1980
tttattgttt aagttgtgat ttttttgtaa tttccttta gacttgttaa tgatttgtgt   2040
ttttgttgaa agtttgtatt aaatacccat acatgtttag tatttttata tttgaattta   2100
ataagatttt gttgttatta ttatgttta ttgataagct tcaaaatttt aaactaaaaa   2160
gaaaaatcga aaataaatc cgacaatgaa tccaactcca actttaagtg tcgggtatag   2220
atttagttta agattttatg tgagtatttt ggttgttcca cgtttgaatt ttcactcgat   2280
tcaaaaatca ctatcaatct agctcaactc aacctagccg acgtacacta ttcgcctta   2340
attttttctt ctcactttc ttactagtca tccttcctgg atttgcattt aaatcttttc   2400
taatttagag tttgaaaagt tgctatcata tatcaacaga atcatttgac ttagagcatc   2460
caaacatata atatgtagtc atgtcttcga ttaaagtata ggaaattatt attataaaaa   2520
aatatcaatt acaggaaaaa gacagagaaa aataaaagag agagaattag ccaataaagt   2580
cactaccagt tgtgttgttt gtgataaaaa ataattaaaa aaaaactctt taatatcatg   2640
caccctaccc ctcttctcct cactatatat atagatatat aaatgtcact ctaaattccc   2700
cacacaaaca cacaaagatt tcaatatcaa tagtcctata ccaaccctaa aatatattcc   2760
tctcctatta tctacctaca tattactgta cactcacata tgatggcatc cttgtcttct   2820
aaagctagcc atgattctca tggacaaaat tcttcctact tctttggatt gcaagagtat   2880
```

```
gagaaggacc cttatcaccc tattcaaaac ccctcgggaa ttatacaaat gggtcttgcc   2940
gaaaacaagg taattcttga atgtaattaa gttggactac aaccattatt gttccttttg   3000
tagtttaact acacatggtc gaatcatttg ttatcaaatg acattgtagt cggttgaaat   3060
atattgagta attaagtaag aaaaagatgt aaacgcggat gcatcaaagt aaaaccaaat   3120
aaaaatatgt tacgtagcaa ttaatttatt taatgaattt tgtaaggttt agttaacggt   3180
ttcttttata tatgcttgtt atgatcacga tgattatgga ttatggatta tggttttgga   3240
ggtagaaaat ttgattgtaa catgtgatat ttaaatgggt tttgcaggta tgtcctgacc   3300
ttttggatga gtggatggag aacaatccag atgctttggg attgagaaga aatggagtgt   3360
ctgagtttag agaattagct ctatttcaag actatcatgg cttgccagct tttaaaaagg   3420
tacctagcct acaaccctag ttttattcat aaagggctct tcaaattttc tttttctttc   3480
ttttttattt atttgtttac tattgaagta atataaataa taaataatag gtgttggttg   3540
aatcaatgga agagatacga ggaaacaaaa tgaaatttga aaagaacaaa ctggtgctca   3600
ctgctggtgc aactgctgcc aatgaaatca taatatcctg tcttccgatc ccggtgaagc   3660
cttccttgtt cccactcctt actatccagg gtatctaaat tcaatcatct tcctatgttt   3720
aagttttctc tctttcttat cacttggttt gtaagaatat acgtatatat actgcaggtt   3780
tgacagggac ttaaaatggc gaactggagt gcaaataatt ccaattcatt gttcgagttc   3840
aaacggtttt cgaatcaccg aagtgtcgat ggaggaagcc atggagcaag cccaatcatt   3900
gaatttacga gtcaaaggga ttatgattac gaacccatct aacccattgg gcaccacatt   3960
gagccagaaa gagctcaact cagtggtgga ttttgctaca accaacgcaa tccacatcgt   4020
gagcgacgag atatattctg ccacagtttt tgagcaaccg aatttccgaa ctgtcatgga   4080
cccgaaccta caaaaactcc caatttggga tcgaatccac ttggtgtaca gcttgtccaa   4140
agatttaggc ctacctgggt ttcgtgtggg catgatttat tcaaacgacc cagcggtagt   4200
ggatgcggct actaaaatgt cgagcttttg cttagtttct tctcaaacac agtattttgt   4260
gtcacaaatt gtaggggatg aaaattttcg agggaattat atgcaggaaa tgaagcggag   4320
gatccggaag aggagattga tgttggagtc gagtcttcga cagggcggtg ttagatgtct   4380
gaaaggaaat gcggggttgt tttgttgggt ggatatgagg catcttttga agtacccgag   4440
tttcgaagag gaaatggaga tttggaagac gattttgtat gaggttggga ttaatatctc   4500
ccccggctca tcttttcatt gctctgaacc tggttggttc agaatgtgct ttgctaatat   4560
ggaggagcac actttcaagg aggccatgca tcgtcttaag gcctttctca actctacctc   4620
atctctcaac ggccatgaac tctcccccac taacgtataa tatgttattg atgtagtcca   4680
attgcaggta gaggattgaa tcacaactca atcaaataat tatattagtt atgttttcta   4740
ctctatataa ttttgtacta ttaagacgtt gtaatataaa tatagatcga tccacataga   4800
atcgatcaac tttcattcca attcaccttc ttgttgtaaa caaggagttt gatgtattat   4860
tggtttggtt tgtaataaat ttaactaaag cagtaaattg gaaatttggt tggattaaaa   4920
tttcaaaaaa atcacacaaa taccgataga gaaaataatg ttaagattac tcttgatttc   4980
ctactcaatc attagattaa tcatacacat ttttggcaat tctatgaaca taattttagc   5040
tgactacatc tagaaaggct agagagccgg gatgtccagt taaccaaatt gatctttatg   5100
tttagaggaa aaccatctca aacatgcaaa tcaattaatc tgcatttatt ccaatgatta   5160
ttgttaagtc aaacaattaa cttggaattg cctagttaag tactccccaa atcaatgcta   5220
```

| | | | | | |
|---|---|---|---|---|---|
| atcaatccca | attatgttaa | tcaaacttat | tagattataa | ttgtcaaatc | aatatacaaa | 5280 |
| tctaacttaa | cttgcgttac | tcggcgatct | aagattttag | cgactatgga | ctatatccgg | 5340 |
| atctatagca | ataaattaca | tatgcttgat | tacttatcaa | tgtttctaaa | tacgctcaat | 5400 |
| cgaattcgat | aaataagatg | acgacaagaa | tttgatatat | cataaaatta | aaatgaaaag | 5460 |
| atttctaatc | tcatgagttt | gccaatcaaa | atataaacct | taaattttga | atcatataaa | 5520 |
| catcgcacga | aaaacacatg | cttttctatc | ttacggtgtc | gtggtgctag | ctagtcctcc | 5580 |
| tttaaaagtg | attctatcca | atgttatttg | tattaaatct | aattaattat | acataagggc | 5640 |
| attttatcaa | gattaaaaag | aatatataat | cgttacatga | aaatatatac | attatacaga | 5700 |
| ataaaactat | gacataaaat | taaactcctc | cgaatgcatt | ttgaaatctt | gttaatatct | 5760 |
| gtaatagaat | taacataggc | ttgggcttgg | agtcttaaat | gggctggtac | tatccacctt | 5820 |
| aatgggctgc | tttggtttga | tcactttaat | tatgggccgt | agcttcagtt | cttttcaggat | 5880 |
| cctctccttc | tgaaagtgct | ctttagcctt | cgactttga | agaaagtat | attaaaaagg | 5940 |
| ttttgacata | acttttctta | ttttcatttg | ctacgtggag | tttgtgttgt | atattatgtt | 6000 |

<210> SEQ ID NO 5
<211> LENGTH: 1322
<212> TYPE: DNA
<213> ORGANISM: Cucumis sativus

<400> SEQUENCE: 5

| | | | | | |
|---|---|---|---|---|---|
| atggcatcct | tgtcttctaa | agctagccat | gattctcatg | acaaaattc | ttcctacttc | 60 |
| tttggattgc | aagagtatga | gaaggaccct | tatcacccta | tcaaaaccc | ctcgggaatt | 120 |
| atacaaatgg | gtcttgccga | aacaaggta | tgtcctgacc | ttttggatga | gtggatggag | 180 |
| aacaatccag | atgctttggg | attgagaaga | aatggagtgt | ctgagtttag | agaattagct | 240 |
| ctatttcaag | actatcatgg | cttgccagct | tttaaaaagg | tgttggttga | atcaatggaa | 300 |
| gagatacgag | gaaacaaaat | gaaatttgaa | agaacaaac | tggtgctcac | tgctggtgca | 360 |
| actgctgcca | atgaaatcat | aatatcctgt | cttccgatcc | cggtgaagcc | ttccttgttc | 420 |
| ccactcctta | ctatccaggg | tttgacaggg | acttaaaatg | cgaactgga | gtgcaaataa | 480 |
| ttccaattca | ttgttcgagt | tcaaacggtt | ttcgaatcac | cgaagtgtcg | atggaggaag | 540 |
| ccatggagca | agcccaatca | ttgaatttac | gagtcaaagg | gattatgatt | acgaacccat | 600 |
| ctaacccatt | gggcaccaca | ttgagccaga | aagagctcaa | ctcagtggtg | gattttgcta | 660 |
| caaccaacgc | aatccacatc | gtgagcgacg | agatatattc | tgccacagtt | tttgagcaac | 720 |
| cgaatttccg | aactgtcatg | gacccgaacc | tacaaaaact | cccaatttgg | gatcgaatcc | 780 |
| acttggtgta | cagcttgtcc | aaagatctag | gcctacctgg | gttcgtgtg | ggcatgattt | 840 |
| attcaaacga | cccagcggta | gtggatgcgg | ctactaaaat | gtcgagcttt | tgcttagttt | 900 |
| cttctcaaac | acagtatttt | gtgtcacaaa | ttgtagggga | tgaaattttt | cgagggaatt | 960 |
| atatgcagga | aatgaagcgg | aggatccgga | agaggagatt | gatgttggag | tcgagtcttc | 1020 |
| gacagggcgg | tgttagatgt | ctgaaaggaa | atgcggggtt | gttttgttgg | gtggatatga | 1080 |
| ggcatctttt | gaagtacccg | agtttcgaag | aggaaatgga | gatttggaag | acgattttgt | 1140 |
| atgaggttgg | gattaatatc | tcccccggct | catcttttca | ttgctctgaa | cctggttggt | 1200 |
| tcagaatgtg | ctttgctaat | atggaggagc | acactttcaa | ggaggccatg | catcgtctta | 1260 |
| aggcctttct | caactctacc | tcatctctca | acggccatga | actctccccc | actaacgtat | 1320 |
| aa | | | | | | 1322 |

```
<210> SEQ ID NO 6
<211> LENGTH: 151
<212> TYPE: PRT
<213> ORGANISM: Cucumis sativus

<400> SEQUENCE: 6

Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30

Pro Ile Gln Asn Pro Ser Gly Ile Ile Gln Met Gly Leu Ala Glu Asn
        35                  40                  45

Lys Val Cys Pro Asp Leu Leu Asp Glu Trp Met Glu Asn Asn Pro Asp
    50                  55                  60

Ala Leu Gly Leu Arg Arg Asn Gly Val Ser Glu Phe Arg Glu Leu Ala
65                  70                  75                  80

Leu Phe Gln Asp Tyr His Gly Leu Pro Ala Phe Lys Lys Val Leu Val
                85                  90                  95

Glu Ser Met Glu Glu Ile Arg Gly Asn Lys Met Lys Phe Glu Lys Asn
            100                 105                 110

Lys Leu Val Leu Thr Ala Gly Ala Thr Ala Ala Asn Glu Ile Ile Ile
        115                 120                 125

Ser Cys Leu Pro Ile Pro Val Lys Pro Ser Leu Phe Pro Leu Leu Thr
    130                 135                 140

Ile Gln Gly Leu Thr Gly Thr
145                 150

<210> SEQ ID NO 7
<211> LENGTH: 6001
<212> TYPE: DNA
<213> ORGANISM: Cucumis sativus

<400> SEQUENCE: 7
tatgttgtcg acgtggatga aactgatatt ctaaaaagaa gtagattaaa atattagaaa      60
atacatctac gaaacgatag tgaaattaca caaggtttgt atatatagaa aaattgaccg     120
catttcattg atgatgatag tttattatta atagatcata ttgtaaatag tattttatga     180
ttttattacc tttgtaattt ttttaaatat ttgtgaacaa aatgtatttg gattagatga     240
atatatatca gtgttttaat gaggcaaatg ctaatattat ggaatgtcca tagtaaatgg     300
atgaggaaat atgatgaatg attatataaa ggaaatataa ttaagaatga attagggttg     360
ttaatttgat ttaggagaaa atggattatt gtaaatgtaa aatgtaaaaa gagaaaatat     420
agttagggaa ggcgacaaga aagaaagaaa gagagaaagg gttgagtgtt aaaaatacac     480
tacgatggac cactctctct tccccttcct ctctcatcat atgacacgtg cctttacctc     540 cttgttttt c aaattttacg gagccattgt cagataccgc gtttcccttc gtggaccacc     600 ccaaaccct a attccccaaa ctaacttcac ttcctcgcta atattacttt cattatattt     660
accctcctat tactttaaat aagagaaaag tagaatagta ctaatcataa ctccagaatt     720
atgatctaaa taattctaat cctaattcta gaataataat aactgctaga acaaacatac     780
atgaagtggg ctatttattc ataggatgag atgtaaaggc gtcatttgag tttggatgaa     840
aaggaaatta agagagagag aggagaggag aaagtcaatg ggtaggacgg ttgcgtgtga     900
ttggcatgag ccatcttgtt aaaccatagt gtgtcggtga aatatgtgaa tatgcaaaac     960
```

```
catacacgcc ttctcctctc tttacatatt ccatacttct cattaatatc actgcccaac    1020
aaatttatat tctctttcac ttattacttt tacattttc caactcttcc tatttttatt    1080 ttacatttt caacccttg aatttcaatt tattaactta caaaaccttc acctaactta    1140
aaactccaat tctcaatttt caaaacaaat tgatatgtta tcaactacta cgatgttaaa    1200
agatatattt aaaagagata aaaacaaaaa aattgatttg ttttttttt atatttaaat    1260 ttatagaaaa tgaaaatta atccaaatta tggctaatac tccacctcac atctatgggc    1320
tttaactttt aagatgaatt ggtgattcac attccacccc acaaattatg taagagaaga    1380
gaagagaaga gaagatagac aaaaggagtt aattggtatg ccaccatgtg gtcttatcaa    1440
tctacaaccc tcatatggca attcagttga ggtttcacga aaaaggaaat tttggaaata    1500
agttttttcc ttggttttct atattattaa tgtcagccat agcaatgctt ttatacgcga    1560
acaatcccta ttttgggata ataaaagtta aagagtgaat ttaaatattg tacccatttc    1620
gtgtgcagtg tacatatggt agacacggga tgaaaacaaa ctattttcat accccctcatg    1680 attcagctac aacttggcat ctgtgttgtt aactagttta ctttctcaca ttgactcttc    1740
tctaacaaat tcaatgggca taaccatcaa aattcattta aatccatgca taatagctat    1800
tacaataaca aatctcaagt ctctataaca gaggttaaca actatgaaaa ttaacttcat    1860
ttattttgtt ccaataatcc aacaattcca accactcaca tcactactaa tttaaaaggt    1920
ttaaacattt tctagttttc caaattcgat tggattgaag ttaattcttt ttactattct    1980
tttattgttt aagttgtgat ttttttgtaa tttccttta gacttgttaa tgatttgtgt    2040
ttttgttgaa agtttgtatt aaataccat acatgtttag tatttttata tttgaattta    2100
ataagatttt gttgttatta ttatgtttta ttgataagct tcaaaatttt aaactaaaaa    2160
gaaaaatcga aaatataac cgacaatgaa tccaactcca actttaagtg tcgggtatag    2220
atttagttta agattttatg tgagtatttt ggttgttcca cgtttgaatt ttcactcgat    2280
tcaaaaatca ctatcaatct agctcaactc aacctagccg acgtacacta ttcgccttta    2340 atttttctt ctcacttttc ttactagtca tccttcctgg atttgcattt aaatctttc    2400 taatttagag tttgaaaagt tgctatcata tatcaacaga atcatttgac ttagagcatc    2460
caaacatata atatgtagtc atgtcttcga ttaaagtata ggaaattatt attataaaaa    2520
aatatcaatt acaggaaaaa gacagagaaa aataaaagag agagaattag ccaataaagt    2580
cactaccagt tgtgttgttt gtgataaaaa ataattaaaa aaaaactctt taatatcatg    2640
caccctaccc ctcttctcct cactatatat atagatatat aaatgtcact ctaaattccc    2700
cacacaaaca cacaaagatt tcaatatcaa tagtcctata ccaaccctaa aatatattcc    2760
tctcctatta tctacctaca tattactgta cactcacata tgatggcatc cttgtcttct    2820
aaagctagcc atgattctca tggacaaaat tcttcctact tctttggatt gcaagagtat    2880
gagaaggacc cttatcaccc tattcaaaac ccctcgggaa ttatacaaat gggtcttgcc    2940
gaaaacaagg taattcttga atgtaattaa gttggactac aaccattatt gttccttttg    3000
tagtttaact acacatggtc gaatcatttg ttatcaaatg acattgtagt cggttgaaat    3060
atattgagta attaagtaag aaaaagatgt aaacgcggat gcatcaaagt aaaaccaaat    3120
aaaaatatgt tacgtagcaa ttaatttatt taatgaattt tgtaaggttt agttaacggt    3180
ttcttttata tatgcttgtt atgatcacga tgattatgga ttatggatta tggttttgga    3240
ggtagaaaat ttgattgtaa catgtgatat ttaaatgggt tttgcaggta tgtcctgacc    3300
ttttggatga gtagatggag aacaatccag atgctttggg attgagaaga aatggagtgt    3360
```

```
ctgagtttag agaattagct ctatttcaag actatcatgg cttgccagct tttaaaaagg    3420
tacctagcct acaaccctag ttttattcat aaagggctct tcaaattttc tttttctttc    3480
ttttttattt atttgtttac tattgaagta atataaataa taaataatag gtgttggttg    3540
aatcaatgga agagatacga ggaaacaaaa tgaaatttga aaagaacaaa ctggtgctca    3600
ctgctggtgc aactgctgcc aatgaaatca taatatcctg tcttgccgat cccggtgaag    3660
ccttccttgt tcccactcct tactatccag ggtatctaaa ttcaatcatc ttcctatgtt    3720
taagttttct ctctttctta tcacttggtt tgtaagaata tacgtatata tactgcaggt    3780
ttgacaggga cttaaaatgg cgaactggag tgcaaataat tccaattcat tgttcgagtt    3840
caaacggttt tcgaatcacc gaagtgtcga tggaggaagc catggagcaa gcccaatcat    3900
tgaatttacg agtcaaaggg attatgatta cgaacccatc taacccattg ggcaccacat    3960
tgagccagaa agagctcaac tcagtggtgg attttgctac aaccaacgca atccacatcg    4020
tgagcgacga gatatattct gccacagttt ttgagcaacc gaatttccga actgtcatgg    4080
acccgaacct acaaaaactc ccaatttggg atcgaatcca cttggtgtac agcttgtcca    4140
aagatttagg cctacctggg tttcgtgtgg gcatgattta ttcaaacgac ccagcggtag    4200
tggatgcggc tactaaaatg tcgagctttt gcttagtttc ttctcaaaca cagtattttg    4260
tgtcacaaat tgtaggggat gaaaattttc gagggaatta tatgcaggaa atgaagcgga    4320
ggatccggaa gaggagattg atgttggagt cgagtcttcg acagggcggt gttagatgtc    4380
tgaaaggaaa tgcggggttg tttttgtggg tggatatgag gcatcttttg aagtacccga    4440
gtttcgaaga ggaaatggag atttggaaga cgattttgta tgaggttggg attaatatct    4500
cccccggctc atcttttcat tgctctgaac ctggttggtt cagaatgtgc tttgctaata    4560
tggaggagca cactttcaag gaggccatgc atcgtcttaa ggccttttct caactctacct    4620 catctctcaa cggccatgaa ctctccccca ctaacgtata atatgttatt gatgtagtcc    4680
aattgcaggt agaggattga atcacaactc aatcaaataa ttatattagt tatgttttct    4740
actctatata attttgtact attaagacgt tgtaatataa atatagatcg atccacatag    4800
aatcgatcaa ctttcattcc aattcacctt cttgttgtaa acaaggagtt tgatgtatta    4860
ttggtttggt ttgtaataaa tttaactaaa gcagtaaatt ggaaatttgg ttggattaaa    4920
atttcaaaaa aatcacacaa ataccgatag agaaaataat gttaagatta ctcttgattt    4980
cctactcaat cattagatta atcatacaca ttttttggcaa ttctatgaac ataattttag    5040
ctgactacat ctagaaaggc tagagagccg ggatgtccag ttaaccaaat tgatcttat    5100 gtttagagga aaaccatctc aaacatgcaa atcaattaat ctgcatttat tccaatgatt    5160
attgttaagt caaacaatta acttggaatt gcctagttaa gtactcccca aatcaatgct    5220
aatcaatccc aattatgtta atcaaactta ttagattata attgtcaaat caatatacaa    5280
atctaactta acttgcgtta ctcggcgatc taagatttta gcgactatgg actatatccg    5340
gatctatagc aataaattac atatgcttga ttacttatca atgtttctaa atacgctcaa    5400
tcgaattcga taaataagat gacgacaaga atttgatata tcataaaatt aaaatgaaaa    5460
gatttctaat ctcatgagtt tgccaatcaa aatataaacc ttaaatttg aatcatataa    5520 acatcgcacg aaaaacacat gcttttctat cttacggtgt cgtggtgcta gctagtcctc    5580
ctttaaaagt gattctatcc aatgttattt gtattaaatc taattaatta tacataaggg    5640
cattttatca agattaaaaa gaatatataa tcgttacatg aaaatatata cattatacag    5700
```

```
aataaaacta tgacataaaa ttaaactcct ccgaatgcat tttgaaatct tgttaatatc    5760
tgtaatagaa ttaacatagg cttgggcttg gagtcttaaa tgggctggta ctatccacct    5820
taatgggctg ctttggtttg atcactttaa ttatgggccg tagcttcagt tctttcagga    5880
tcctctcctt ctgaaagtgc tctttagcct tcgacttttg aaagaaagta tattaaaaag    5940
gttttgacat aacttttctt attttcattt gctacgtgga gtttgtgttg tatattatgt    6000
t                                                                    6001

<210> SEQ ID NO 8
<211> LENGTH: 1323
<212> TYPE: DNA
<213> ORGANISM: Cucumis sativus

<400> SEQUENCE: 8
atggcatcct tgtcttctaa agctagccat gattctcatg gacaaaattc ttcctacttc      60
tttggattgc aagagtatga aaggaccct tatcacccta ttcaaaaccc ctcgggaatt      120
atacaaatgg gtcttgccga aaacaaggta tgtcctgacc ttttggatga gtagatggag      180
aacaatccag atgctttggg attgagaaga aatggagtgt ctgagtttag agaattagct      240
ctatttcaag actatcatgg cttgccagct tttaaaaagg tgttggttga atcaatggaa      300
gagatacgag gaaacaaaat gaaatttgaa agaacaaac tggtgctcac tgctggtgca      360
actgctgcca atgaaatcat aatatcctgt cttgccgatc ccggtgaagc cttccttgtt      420
cccactcctt actatccagg gtttgacagg gacttaaaat ggcgaactgg agtgcaaata      480
attccaattc attgttcgag ttcaaacggt tttcgaatca ccgaagtgtc gatggaggaa      540
gccatggagc aagcccaatc attgaattta cgagtcaaag ggattatgat tacgaaccca      600
tctaacccat tgggcaccac attgagccag aaagagctca actcagtggt ggattttgct      660
acaaccaacg caatccacat cgtgagcgac gagatatatt ctgccacagt ttttgagcaa      720
ccgaatttcc gaactgtcat ggacccgaac ctacaaaaac tcccaatttg ggatcgaatc      780
cacttggtgt acagcttgtc caaagatcta ggcctacctg ggtttcgtgt gggcatgatt      840
tattcaaacg acccagcggt agtggatgcg gctactaaaa tgtcgagctt tgcttagtt      900 tcttctcaaa cacagtattt tgtgtcacaa attgtagggg atgaaaattt tcgagggaat      960
tatatgcagg aaatgaagcg gaggatccgg aagaggagat gatgttgga gtcgagtctt     1020 cgacagggcg gtgttagatg tctgaaagga aatgcggggt tgttttgttg ggtggatatg     1080
aggcatcttt tgaagtaccc gagtttcgaa gaggaaatgg agatttggaa gacgattttg     1140
tatgaggttg ggattaatat ctcccccggc tcatcttttc attgctctga acctggttgg     1200
ttcagaatgt gctttgctaa tatggaggag cacactttca aggaggccat gcatcgtctt     1260 aaggccttc tcaactctac ctcatctctc aacggccatg aactctcccc cactaacgta     1320
taa                                                                   1323

<210> SEQ ID NO 9
<211> LENGTH: 57
<212> TYPE: PRT
<213> ORGANISM: Cucumis sativus

<400> SEQUENCE: 9

Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30
```

```
Pro Ile Gln Asn Pro Ser Gly Ile Ile Gln Met Gly Leu Ala Glu Asn
        35                  40                  45

Lys Val Cys Pro Asp Leu Leu Asp Glu
    50                  55

<210> SEQ ID NO 10
<211> LENGTH: 2225
<212> TYPE: DNA
<213> ORGANISM: Cucumis melo

<400> SEQUENCE: 10
cacaaacaca cacagaatat ttcaatatca atatagccct ataccaac ccctagaata       60 tattccatct ctccctctcc tattatctac ctacatactg tacactcata tatgatggca     120
atgttgtcta ctaaagctgg ccatgattct catggacaaa attcttccta cttctttgga    180
tggcaagagt acgagaagaa cccttatcac cctactcaaa accccctccgg gattatccaa   240 atgggtcttg ccgaaaacag gtaatccttg aataatgtt cgttggacta taaccaccat     300
tatttctttt gtagtttaac tacatggtcg aattatttgt tatcatgtaa cgatactagt    360
tggttgggct atttgatcaa cccttctagc agtgaagtaa gaaaaagatt tggaggcgga    420
tgaattaaaa gtaagaccaa acaaaaaata tgttacgtag caatgaattt ttaaaaattt    480
aaggagtggt ttcttttgtg cttgttatga tcatatgatt atggttatgg ttttgaaggg    540
agggaatttt attgtatgta aaagaatat gtaatattaa atgggtttg caggtatgtt     600 atgacttctt ggatgagtgg atggagaaca atccagatgc tttaggattg agaaaaaatg    660
gagtgtcttt gtttagagaa ttggctctat ttcaagacta ccatggcttg ccggcttta    720 aaaaggtacc tagcctacaa ccctagtttt tcataaaggg ctcttcaact tttcttttct    780
ttcttttatt ttatttattt gtttattatt gaaataatat ttgataaata ataggcgttg    840
gttgaatcaa tggaagaaat acgaggaaac aaaatgaaat ttgagatgaa caaactggtg    900
ctaaccgctg gtgcaactgc tgccaatgaa atcctcatat cttgtcttgc cgatcccggt    960
gaagcgttcc tcgttcccac tccttactat ccagggtaaa taattcaat aactttccaa    1020 tatataaatc ttctcttttt attagtgcgt ttgtgaaaat agaaaaaata ataagcatat    1080
atatgaatgt aggtttgaca gggacttaaa atggcgtaca gaagttcaaa taattccaat    1140
ccattgttcg agttcaaaca gcttccaaat cacagaagcg gcgatggagg aagccatgga    1200
gcaagcccaa acattgaatt tacgagtcaa agggattatg attacgaacc catccaaccc    1260
attaggcacc acattgagcc agaaagagat taactcggtg gtggatttcg ctatagccaa    1320
tgcaatccac atcgtgagcg atgagatata ttccgccaca gtttttgagc acccaaagtt    1380
tcgaactgtc atggacccga acctacaaaa attcccaatt tgggaccgaa tccacttggt    1440
gtacagcttg tccaaagatc tgggcctacc cgggttccgc gtgggcatga tttattcaaa    1500
cgacctagca gtagtggatg cggctaccaa aatgtctagc ttttgtttag tttcttctca    1560
aacacagtat tttgtgtcgc aaattgtagg ggatgaaaaa tttcgaggca attatatgca    1620
ggaaatgaag cggaggattc gaaagaggag attgatgttg gagtcgagtc tccgacaggg    1680
cggtgttaga tgtttgaaag ggaatgcagg gttgttttgt tgggtggata tgaggcatct    1740
tttgaagtac ccgagtttcg aagaggaaat ggagatttgg aagacgattt tgtatgaggt    1800
tgggattaat atctctcccg gttcgtcttt tcattgctct gaaccggtt ggtttagaat     1860 gtgctttgcc aatatggagg aacacacttt caaggtggcc atgcatcgtc ttaagacctt    1920
```

```
tctcaactct acctcacctc tcaatgccta cgaactctcc cccactaaca tataatgtat    1980
tactaataat gtagtctaat tgcaggtgga ggagtgaatc acgaatccaa acatagtcct    2040 tgcttttat  atttatgttt tctgctctat ataattccgt acgtagtatt agggttgtaa    2100
aataaatgtg ggtcgatcaa cgtagaatcg atcaattttc cttcaaattc accttcttgt    2160
tgtaaccaag gggtttgatg tattggtttc tgtctgtaac aaattgaact aaagcagtaa    2220
attgg                                                               2225
```

<210> SEQ ID NO 11
<211> LENGTH: 1323
<212> TYPE: DNA
<213> ORGANISM: Cucumis melo

<400> SEQUENCE: 11

```
atggcaatgt tgtctactaa agctggccat gattctcatg gacaaaattc ttcctacttc      60
tttggatggc aagagtacga gaagaaccct tatcaccta ctcaaaaccc ctccgggatt     120
atccaaatgg gtcttgccga aaacagggta tgttatgact tcttggatga gtggatggag     180
aacaatccag atgctttagg attgagaaaa aatggagtgt ctttgtttag agaattggct     240
ctatttcaag actaccatgg cttgccggct tttaaaaagg cgttggttga atcaatggaa     300
gaaatacgag aaacaaaat gaaatttgag atgaacaaac tggtgctaac cgctggtgca     360
actgctgcca atgaaatcct catatcttgt cttgccgatc ccggtgaagc gttcctcgtt     420
cccactcctt actatccagg gtttgacagg gacttaaaat ggcgtacaga agttcaaata     480
attccaatcc attgttcgag ttcaaacagc ttccaaatca cagaagcggc gatggaggaa     540
gccatggagc aagcccaaac attgaattta cgagtcaaag ggattatgat tacgaaccca     600
tccaacccat taggcaccac attgagccag aaagagatta actcggtggt ggatttcgct     660
atagccaatg caatccacat cgtgagcgat gagatatatt ccgccacagt ttttgagcac     720
ccaaagtttc gaactgtcat ggacccgaac ctacaaaaat tcccaatttg ggaccgaatc     780
cacttggtgt acagcttgtc caaagatctg ggcctacccg ggttccgcgt gggcatgatt     840
tattcaaacg acctagcagt agtggatgcg gctaccaaaa tgtctagctt tgtttagtt      900 tcttctcaaa cacagtattt tgtgtcgcaa attgtagggg atgaaaaatt tcgaggcaat     960
tatatgcaga aaatgaagcg gaggattcga agaggagagt tgatgttgga gtcgagtctc    1020
cgacagggcg tgttagatg tttgaaaggg aatgcagggt tgttttgttg ggtggatatg     1080
aggcatcttt tgaagtaccc gagtttcgaa gaggaaatgg agatttggaa gacgattttg    1140
tatgaggttg ggattaatat ctctcccggt tcgtcttttc attgctctga acccggttgg    1200
tttagaatgt gcttttgccaa tatggaggaa cacacttttca aggtggccat gcatcgtctt    1260
aagacctttc tcaactctac ctcacctctc aatgcctacg aactctcccc cactaacata    1320
taa                                                                  1323
```

<210> SEQ ID NO 12
<211> LENGTH: 440
<212> TYPE: PRT
<213> ORGANISM: Cucumis melo

<400> SEQUENCE: 12

```
Met Ala Met Leu Ser Thr Lys Ala Gly His Asp Ser His Gly Gln Asn
 1               5                  10                  15

Ser Ser Tyr Phe Phe Gly Trp Gln Glu Tyr Glu Lys Asn Pro Tyr His
            20                  25                  30
```

```
Pro Thr Gln Asn Pro Ser Gly Ile Ile Gln Met Gly Leu Ala Glu Asn
        35                  40                  45

Arg Val Cys Tyr Asp Phe Leu Asp Glu Trp Met Glu Asn Asn Pro Asp
    50                  55                  60

Ala Leu Gly Leu Arg Lys Asn Gly Val Ser Leu Phe Arg Glu Leu Ala
65                  70                  75                  80

Leu Phe Gln Asp Tyr His Gly Leu Pro Ala Phe Lys Lys Ala Leu Val
                85                  90                  95

Glu Ser Met Glu Glu Ile Arg Gly Asn Lys Met Lys Phe Glu Met Asn
            100                 105                 110

Lys Leu Val Leu Thr Ala Gly Ala Thr Ala Ala Asn Glu Ile Leu Ile
                115                 120                 125

Ser Cys Leu Ala Asp Pro Gly Glu Ala Phe Leu Val Pro Thr Pro Tyr
            130                 135                 140

Tyr Pro Gly Phe Asp Arg Asp Leu Lys Trp Arg Thr Glu Val Gln Ile
145                 150                 155                 160

Ile Pro Ile His Cys Ser Ser Asn Ser Phe Gln Ile Thr Glu Ala
                165                 170                 175

Ala Met Glu Glu Ala Met Glu Gln Ala Gln Thr Leu Asn Leu Arg Val
            180                 185                 190

Lys Gly Ile Met Ile Thr Asn Pro Ser Asn Pro Leu Gly Thr Thr Leu
                195                 200                 205

Ser Gln Lys Glu Ile Asn Ser Val Val Asp Phe Ala Ile Ala Asn Ala
            210                 215                 220

Ile His Ile Val Ser Asp Glu Ile Tyr Ser Ala Thr Val Phe Glu His
225                 230                 235                 240

Pro Lys Phe Arg Thr Val Met Asp Pro Asn Leu Gln Lys Phe Pro Ile
                245                 250                 255

Trp Asp Arg Ile His Leu Val Tyr Ser Leu Ser Lys Asp Leu Gly Leu
            260                 265                 270

Pro Gly Phe Arg Val Gly Met Ile Tyr Ser Asn Asp Leu Ala Val Val
            275                 280                 285

Asp Ala Ala Thr Lys Met Ser Ser Phe Cys Leu Val Ser Ser Gln Thr
290                 295                 300

Gln Tyr Phe Val Ser Gln Ile Val Gly Asp Glu Lys Phe Arg Gly Asn
305                 310                 315                 320

Tyr Met Gln Glu Met Lys Arg Arg Ile Arg Lys Arg Leu Met Leu
                325                 330                 335

Glu Ser Ser Leu Arg Gln Gly Gly Val Arg Cys Leu Lys Gly Asn Ala
            340                 345                 350

Gly Leu Phe Cys Trp Val Asp Met Arg His Leu Leu Lys Tyr Pro Ser
            355                 360                 365

Phe Glu Glu Glu Met Glu Ile Trp Lys Thr Ile Leu Tyr Glu Val Gly
370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Val Ala
            405                 410                 415

Met His Arg Leu Lys Thr Phe Leu Asn Ser Thr Ser Pro Leu Asn Ala
                420                 425                 430

Tyr Glu Leu Ser Pro Thr Asn Ile
            435                 440
```

<210> SEQ ID NO 13
<211> LENGTH: 2225
<212> TYPE: DNA
<213> ORGANISM: Cucumis melo

<400> SEQUENCE: 13

| | | | | | |
|---|---|---|---|---|---|
| cacaaacaca | cacagaatat | ttcaatatca | atatagccct | ataccaac | ccctagaata | 60 |
| tattccatct | ctccctctcc | tattatctac | ctacatactg | tacactcata | tatgatggca | 120 |
| atgttgtcta | ctaaagctgg | ccatgattct | catggacaaa | attcttccta | cttcttgga | 180 |
| tggcaagagt | acgagaagaa | cccttatcac | cctactcaaa | accctccgg | gattatccaa | 240 |
| atgggttttg | ccgaaaacag | ggtaatcctt | gaataatgtt | cgttggacta | taaccaccat | 300 |
| tatttctttt | gtagtttaac | tacatggtcg | aattatttgt | tatcatgtaa | cgatactagt | 360 |
| tggttgggct | atttgatcaa | cccttctagc | agtgaagtaa | gaaaaagatt | tggaggcgga | 420 |
| tgaattaaaa | gtaagaccaa | acaaaaaata | tgttacgtag | caatgaattt | ttaaaaattt | 480 |
| aaggagtggt | ttctttttgtg | cttgttatga | tcatatgatt | atggttatgg | ttttgaaggg | 540 |
| agggaatttt | attgtatgta | aaagaatat | gtaatattaa | atgggttttg | caggtatgtt | 600 |
| atgacttctt | ggatgagtgg | atggagaaca | atccagatgc | tttaggattg | agaaaaaatg | 660 |
| gagtgtcttt | gtttagagaa | ttggctctat | ttcaagacta | ccatggcttg | ccggctttta | 720 |
| aaaaggtacc | tagcctacaa | ccctagttt | tcataaaggg | ctcttcaact | tttctttct | 780 |
| ttctttatt | ttatttattt | gtttattatt | gaaataatat | ttgataata | ataggcgttg | 840 |
| gttgaatcaa | tggaagaaat | acgaggaaac | aaaatgaaat | ttgagatgaa | caaactggtg | 900 |
| ctaaccgctg | gtgcaactgc | tgccaatgaa | atcctcatat | cttgtcttgc | cgatcccggt | 960 |
| gaagcgttcc | tcgttcccac | tcctactat | ccagggtaaa | taaattcaat | aactttccaa | 1020 |
| tatataaatc | ttctctttt | attagtgcgt | ttgtgaaaat | agaaaaata | ataagcatat | 1080 |
| atatgaatgt | aggtttgaca | gggacttaaa | atggcgtaca | gaagttcaaa | taattccaat | 1140 |
| ccattgttcg | agttcaaaca | gcttccaaat | cacagaagcg | gcgatggagg | aagccatgga | 1200 |
| gcaagcccaa | acattgaatt | tacgagtcaa | agggattatg | attacgaacc | catccaaccc | 1260 |
| attaggcacc | acattgagcc | agaaagagat | taactcggtg | gtggatttcg | ctatagccaa | 1320 |
| tgcaatccac | atcgtgagcg | atgagatata | ttccgccaca | gttttgagc | acccaaagtt | 1380 |
| tcgaactgtc | atggacccga | acctacaaaa | attcccaatt | tgggaccgaa | tccacttggt | 1440 |
| gtacagcttg | tccaaagatc | tgggcctacc | cgggttccgc | gtgggcatga | tttattcaaa | 1500 |
| cgacctagca | gtagtggatg | cggctaccaa | aatgtctagc | ttttgtttag | tttcttctca | 1560 |
| aacacagtat | tttgtgtcgc | aaattgtagg | ggatgaaaaa | tttcgaggca | attatatgca | 1620 |
| ggaaatgaag | cggaggattc | gaaagaggag | attgatgttg | gagtcgagtc | tccgacaggg | 1680 |
| cggtgttaga | tgtttgaaag | ggaatgcagg | gttgttttgt | tgggtggata | tgaggcatct | 1740 |
| tttgaagtac | ccgagtttcg | aagaggaaat | ggagatttgg | aagacgattt | tgtatgaggt | 1800 |
| tgggattaat | atctctcccg | gttcgtctttt | tcattgctct | gaacccggtt | ggtttagaat | 1860 |
| gtgctttgcc | aatatggagg | aacacacttt | caaggtggcc | atgcatcgtc | ttaagacctt | 1920 |
| tctcaactct | acctcacctc | tcaatgccta | cgaactctcc | cccactaaca | tataatgtat | 1980 |
| tactaataat | gtagtctaat | tgcaggtgga | ggagtgaatc | acgaatccaa | acatagtcct | 2040 |
| tgcttttat | atttatgttt | tctgctctat | ataattccgt | acgtagtatt | agggttgtaa | 2100 |
| aataaatgtg | ggtcgatcaa | cgtagaatcg | atcaattttc | cttcaaattc | accttcttgt | 2160 |

```
tgtaaccaag gggtttgatg tattggtttc tgtctgtaac aaattgaact aaagcagtaa    2220
attgg                                                                2225

<210> SEQ ID NO 14
<211> LENGTH: 1323
<212> TYPE: DNA
<213> ORGANISM: Cucumis melo

<400> SEQUENCE: 14
atggcaatgt tgtctactaa agctggccat gattctcatg gacaaaattc ttcctacttc      60
tttggatggc aagagtacga gaagaaccct tatcaccctg ctcaaaaccc ctccgggatt     120
atccaaatgg ttttgccga aacagggta tgttatgact tcttggatga gtggatggag      180
aacaatccag atgctttagg attgagaaaa aatggagtgt ctttgtttag agaattggct    240
ctatttcaag actaccatgg cttgccggct tttaaaaagg cgttggttga atcaatggaa    300
gaaatacgag aaacaaaat gaaatttgag atgaacaaac tggtgctaac cgctggtgca    360
actgctgcca atgaaatcct catatcttgt cttgccgatc ccggtgaagc gttcctcgtt    420
cccactcctt actatccagg gtttgacagg gacttaaaat ggcgtacaga agttcaaata    480
attccaatcc attgttcgag ttcaaacagc ttccaaatca cagaagcggc gatggaggaa    540
gccatggagc aagcccaaac attgaattta cgagtcaaag ggattatgat tacgaaccca    600
tccaacccat taggcaccac attgagccag aaagagatta actcggtggt ggatttcgct    660
atagccaatg caatccacat cgtgagcgat gagatatatt ccgccacagt ttttgagcac    720
ccaaagtttc gaactgtcat ggacccgaac ctacaaaaat tcccaatttg ggaccgaatc    780
cacttggtgt acagcttgtc caaagatctg ggcctacccg ggttccgcgt gggcatgatt    840
tattcaaacg acctagcagt agtggatgcg gctaccaaaa tgtctagctt tgtttagtt    900 tcttctcaaa cacagtattt tgtgtcgcaa attgtagggg atgaaaaatt tcgaggcaat    960
tatatgcagg aaatgaagcg gaggattcga agaggagatt tgatgttgga gtcgagtctc   1020
cgacagggcg tgttagatg tttgaaaggg aatgcagggt tgttttgttg ggtggatatg   1080
aggcatcttt tgaagtaccc gagtttcgaa gaggaaatgg agatttggaa gacgattttg   1140
tatgaggttg ggattaatat ctctcccggt tcgtcttttc attgctctga acccggttgg   1200
tttagaatgt gctttgccaa tatggaggaa cacactttca aggtggccat gcatcgtctt   1260 aagaccttc tcaactctac ctcacctctc aatgcctacg aactctcccc cactaacata   1320
taa                                                                 1323

<210> SEQ ID NO 15
<211> LENGTH: 440
<212> TYPE: PRT
<213> ORGANISM: Cucumis melo

<400> SEQUENCE: 15

Met Ala Met Leu Ser Thr Lys Ala Gly His Asp Ser His Gly Gln Asn
  1               5                  10                  15

Ser Ser Tyr Phe Phe Gly Trp Gln Glu Tyr Glu Lys Asn Pro Tyr His
                 20                  25                  30

Pro Thr Gln Asn Pro Ser Gly Ile Ile Gln Met Gly Phe Ala Glu Asn
             35                  40                  45

Arg Val Cys Tyr Asp Phe Leu Asp Glu Trp Met Glu Asn Asn Pro Asp
         50                  55                  60
```

```
Ala Leu Gly Leu Arg Lys Asn Gly Val Ser Leu Phe Arg Glu Leu Ala
 65                  70                  75                  80

Leu Phe Gln Asp Tyr His Gly Leu Pro Ala Phe Lys Lys Ala Leu Val
             85                  90                  95

Glu Ser Met Glu Glu Ile Arg Gly Asn Lys Met Lys Phe Glu Met Asn
            100                 105                 110

Lys Leu Val Leu Thr Ala Gly Ala Thr Ala Ala Asn Glu Ile Leu Ile
        115                 120                 125

Ser Cys Leu Ala Asp Pro Gly Glu Ala Phe Leu Val Pro Thr Pro Tyr
        130                 135                 140

Tyr Pro Gly Phe Asp Arg Asp Leu Lys Trp Arg Thr Glu Val Gln Ile
145                 150                 155                 160

Ile Pro Ile His Cys Ser Ser Asn Ser Phe Gln Ile Thr Glu Ala
                165                 170                 175

Ala Met Glu Glu Ala Met Glu Gln Ala Gln Thr Leu Asn Leu Arg Val
            180                 185                 190

Lys Gly Ile Met Ile Thr Asn Pro Ser Asn Pro Leu Gly Thr Thr Leu
        195                 200                 205

Ser Gln Lys Glu Ile Asn Ser Val Val Asp Phe Ala Ile Ala Asn Ala
210                 215                 220

Ile His Ile Val Ser Asp Glu Ile Tyr Ser Ala Thr Val Phe Glu His
225                 230                 235                 240

Pro Lys Phe Arg Thr Val Met Asp Pro Asn Leu Gln Lys Phe Pro Ile
                245                 250                 255

Trp Asp Arg Ile His Leu Val Tyr Ser Leu Ser Lys Asp Leu Gly Leu
            260                 265                 270

Pro Gly Phe Arg Val Gly Met Ile Tyr Ser Asn Asp Leu Ala Val Val
        275                 280                 285

Asp Ala Ala Thr Lys Met Ser Ser Phe Cys Leu Val Ser Ser Gln Thr
290                 295                 300

Gln Tyr Phe Val Ser Gln Ile Val Gly Asp Glu Lys Phe Arg Gly Asn
305                 310                 315                 320

Tyr Met Gln Glu Met Lys Arg Arg Ile Arg Lys Arg Leu Met Leu
                325                 330                 335

Glu Ser Ser Leu Arg Gln Gly Gly Val Arg Cys Leu Lys Gly Asn Ala
            340                 345                 350

Gly Leu Phe Cys Trp Val Asp Met Arg His Leu Leu Lys Tyr Pro Ser
        355                 360                 365

Phe Glu Glu Glu Met Glu Ile Trp Lys Thr Ile Leu Tyr Glu Val Gly
370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Val Ala
                405                 410                 415

Met His Arg Leu Lys Thr Phe Leu Asn Ser Thr Ser Pro Leu Asn Ala
            420                 425                 430

Tyr Glu Leu Ser Pro Thr Asn Ile
        435                 440

<210> SEQ ID NO 16
<211> LENGTH: 2225
<212> TYPE: DNA
<213> ORGANISM: Cucumis melo

<400> SEQUENCE: 16
```

```
cacaaacaca cacagaatat ttcaatatca atatagccct atataccaac ccctagaata        60
tattccatct ctccctctcc tattatctac ctacatactg tacactcata tatgatggca       120
atgttgtcta ctaaagctgg ccatgattct catggacaaa attcttccta cttctttgga       180
tggcaagagt acgagaagaa cccttatcac cctactcaaa acccctccgg gattatccaa       240
atgggtcttg ccgaaaacag ggtaatcctt gaataatgtt cgttggacta taaccaccat       300
tatttctttt gtagtttaac tacatggtcg aattatttgt tatcatgtaa cgatactagt       360
tggttgggct atttgatcaa cccttctagc agtgaagtaa gaaaaagatt tggaggcgga       420
tgaattaaaa gtaagaccaa acaaaaaata tgttacgtag caatgaattt ttaaaaattt       480
aaggagtggt ttcttttgtg cttgttatga tcatatgatt atggttatgg ttttgaaggg       540
agggaatttt attgtatgta aaagaatat gtaatattaa atgggttttg caggtatgtt       600
atgacttctt ggatgagtgg atggagaaca atccagatgc tttaggattg agaaaaaatg       660
gagtgtcttt gtttagagaa ttggctctat ttcaagacta ccatggcttg ccggctttta       720
aaaaggtacc tagcctacaa ccctagtttt tcataaaggg ctcttcaact tttcttttct       780
ttcttttatt ttatttattt gtttattatt gaaataatat ttgataaata ataggcgttg       840
gttgaatcaa tggaagaaat acgaggaaac aaaatgaaat ttgagatgaa caaactggtg       900
ctaaccgctg gtgcaactgc tgccaatgaa atcctcatat cttgtcttgc cgatcccggt       960
gaagcgttcc tcgttcccac tccttactat ccagggtaaa taaattcaat aactttccaa      1020
tatataaatc ttctctttt attagtgcgt ttgtgaaaat agaaaaaata ataagcatat      1080
atatgaatgt aggtttgaca gggacttaaa atggcgtaca gaagttcaaa taattccaat      1140
ccattgttcg agttcaaaca gcttccaaat cacagaagcg gcgatggagg aagccatgga      1200
gcaagcccaa acattgaatt tacgagtcaa agggattatg attacgaacc catccaaccc      1260
attaggcacc acattgagcc agaaagagat taactcggtg gtggatttcg ctatagccaa      1320
tgcaatccac atcgtgagcg atgagatata ttccgccaca gttttgagc acccaaagtt      1380 tcgaactgtc atggacccga acctacaaaa attcccaatt tgggaccgaa tccacttggt      1440
gtacagcttg tccaaagatc tgggcctacc cgggttccgc gtgggcatga tttattcaaa      1500
cgacctagca gtagtggatg cggctaccaa aatgtttagc ttttgtttag tttcttctca      1560
aacacagtat tttgtgtcgc aaattgtagg ggatgaaaaa tttcgaggca attatatgca      1620
ggaaatgaag cggaggattc gaaagaggag attgatgttg gagtcgagtc tccgacaggg      1680
cggtgttaga tgtttgaaag ggaatgcagg gttgttttgt tgggtggata tgaggcatct      1740
tttgaagtac ccgagtttcg aagaggaaat ggagatttgg aagacgattt tgtatgaggt      1800
tgggattaat atctctcccg gttcgtcttt tcattgctct gaacccggtt ggtttagaat      1860
gtgctttgcc aatatggagg aacacacttt caaggtggcc atgcatcgtc ttaagacctt      1920
tctcaactct acctcacctc tcaatgccta cgaactctcc cccactaaca tataatgtat      1980
tactaataat gtagtctaat tgcaggtgga ggagtgaatc acgaatccaa acatagtcct      2040 tgcttttat atttatgttt tctgctctat ataattccgt acgtagtatt agggttgtaa      2100
aataaatgtg ggtcgatcaa cgtagaatcg atcaattttc cttcaaattc accttcttgt      2160
tgtaaccaag gggtttgatg tattggtttc tgtctgtaac aaattgaact aaagcagtaa      2220
attgg                                                                 2225
```

<210> SEQ ID NO 17

```
<211> LENGTH: 1323
<212> TYPE: DNA
<213> ORGANISM: Cucumis melo

<400> SEQUENCE: 17
atggcaatgt tgtctactaa agctggccat gattctcatg gacaaaattc ttcctacttc      60
tttggatggc aagagtacga gaagaaccct tatcacccta ctcaaaaccc ctccgggatt     120
atccaaatgg gtcttgccga aaacagggta tgttatgact tcttggatga gtggatggag     180
aacaatccag atgctttagg attgagaaaa aatggagtgt ctttgtttag agaattggct     240
ctatttcaag actaccatgg cttgccggct tttaaaaagg cgttggttga atcaatggaa     300
gaaatacgag gaaacaaaat gaaatttgag atgaacaaac tggtgctaac cgctggtgca     360
actgctgcca atgaaatcct catatcttgt cttgccgatc ccggtgaagc gttcctcgtt     420
cccactcctt actatccagg gtttgacagg gacttaaaat ggcgtacaga agttcaaata     480
attccaatcc attgttcgag ttcaaacagc ttccaaatca cagaagcggc gatggaggaa     540
gccatggagc aagcccaaac attgaattta cgagtcaaag ggattatgat tacgaaccca     600
tccaacccat taggcaccac attgagccag aaagagatta actcggtggt ggatttcgct     660
atagccaatg caatccacat cgtgagcgat gagatatatt ccgccacagt ttttgagcac     720
ccaaagtttc gaactgtcat ggaccccgaac ctacaaaaat tcccaatttg gaccgaatc     780
cacttggtgt acagcttgtc caaagatctg ggcctacccg ggtccgcgt gggcatgatt     840
tattcaaacg acctagcagt agtggatgcg gctaccaaaa tgtttagctt ttgtttagtt     900
tcttctcaaa cacagtattt tgtgtcgcaa attgtagggg atgaaaaatt tcgaggcaat     960
tatatgcagg aaatgaagcg gaggattcga agaggagat tgatgttgga gtcgagtctc    1020
cgacagggcg tgttagatg tttgaaaggg aatgcagggt tgttttgttg ggtggatatg    1080
aggcatcttt tgaagtaccc gagtttcgaa gaggaaatgg agatttggaa gacgattttg    1140
tatgaggttg ggattaatat ctctcccggt tcgtcttttc attgctctga acccggttgg    1200
tttagaatgt gctttgccaa tatggaggaa cacactttca aggtggccat gcatcgtctt    1260
aagaccttc tcaactctac ctcacctctc aatgcctacg aactctcccc cactaacata    1320
taa                                                                  1323

<210> SEQ ID NO 18
<211> LENGTH: 440
<212> TYPE: PRT
<213> ORGANISM: Cucumis melo

<400> SEQUENCE: 18

Met Ala Met Leu Ser Thr Lys Ala Gly His Asp Ser His Gly Gln Asn
1               5                   10                  15

Ser Ser Tyr Phe Phe Gly Trp Gln Glu Tyr Glu Lys Asn Pro Tyr His
                20                  25                  30

Pro Thr Gln Asn Pro Ser Gly Ile Ile Gln Met Gly Leu Ala Glu Asn
            35                  40                  45

Arg Val Cys Tyr Asp Phe Leu Asp Glu Trp Met Glu Asn Asn Pro Asp
        50                  55                  60

Ala Leu Gly Leu Arg Lys Asn Gly Val Ser Leu Phe Arg Glu Leu Ala
65                  70                  75                  80

Leu Phe Gln Asp Tyr His Gly Leu Pro Ala Phe Lys Lys Ala Leu Val
                85                  90                  95

Glu Ser Met Glu Glu Ile Arg Gly Asn Lys Met Lys Phe Glu Met Asn
```

|  |  |  | 100 |  |  |  | 105 |  |  |  | 110 |  |
|---|---|---|---|---|---|---|---|---|---|---|---|---|

Lys Leu Val Leu Thr Ala Gly Ala Thr Ala Ala Asn Glu Ile Leu Ile
            115                        120                        125

Ser Cys Leu Ala Asp Pro Gly Glu Ala Phe Leu Val Pro Thr Pro Tyr
 130                        135                        140

Tyr Pro Gly Phe Asp Arg Asp Leu Lys Trp Arg Thr Glu Val Gln Ile
145                    150                        155                        160

Ile Pro Ile His Cys Ser Ser Asn Ser Phe Gln Ile Thr Glu Ala
                   165                        170                        175

Ala Met Glu Glu Ala Met Glu Gln Ala Gln Thr Leu Asn Leu Arg Val
          180                        185                        190

Lys Gly Ile Met Ile Thr Asn Pro Ser Asn Pro Leu Gly Thr Thr Leu
        195                      200                        205

Ser Gln Lys Glu Ile Asn Ser Val Val Asp Phe Ala Ile Ala Asn Ala
 210                        215                        220

Ile His Ile Val Ser Asp Glu Ile Tyr Ser Ala Thr Val Phe Glu His
225                    230                        235                        240

Pro Lys Phe Arg Thr Val Met Asp Pro Asn Leu Gln Lys Phe Pro Ile
               245                        250                        255

Trp Asp Arg Ile His Leu Val Tyr Ser Leu Ser Lys Asp Leu Gly Leu
          260                        265                        270

Pro Gly Phe Arg Val Gly Met Ile Tyr Ser Asn Asp Leu Ala Val Val
        275                      280                        285

Asp Ala Ala Thr Lys Met Phe Ser Phe Cys Leu Val Ser Ser Gln Thr
290                    295                        300

Gln Tyr Phe Val Ser Gln Ile Val Gly Asp Glu Lys Phe Arg Gly Asn
305                    310                        315                        320

Tyr Met Gln Glu Met Lys Arg Arg Ile Arg Lys Arg Leu Met Leu
               325                        330                        335

Glu Ser Ser Leu Arg Gln Gly Gly Val Arg Cys Leu Lys Gly Asn Ala
          340                        345                        350

Gly Leu Phe Cys Trp Val Asp Met Arg His Leu Leu Lys Tyr Pro Ser
        355                      360                        365

Phe Glu Glu Glu Met Glu Ile Trp Lys Thr Ile Leu Tyr Glu Val Gly
 370                        375                        380

Ile Asn Ile Ser Pro Gly Ser Ser Phe His Cys Ser Glu Pro Gly Trp
385                    390                        395                        400

Phe Arg Met Cys Phe Ala Asn Met Glu Glu His Thr Phe Lys Val Ala
               405                        410                        415

Met His Arg Leu Lys Thr Phe Leu Asn Ser Thr Ser Pro Leu Asn Ala
          420                        425                        430

Tyr Glu Leu Ser Pro Thr Asn Ile
        435                      440

```
<210> SEQ ID NO 19
<211> LENGTH: 2000
<212> TYPE: DNA
<213> ORGANISM: Citrullus lanatus

<400> SEQUENCE: 19
tagatatata aatgtcactc taaattcccc acacaaacac acaaagattt caatatcaat      60
agcccctata ccaaccctaa aatatattcc tctcctatta tctacctaca tattactgta     120
cactcacata tgatggcatc cttgtcttct aaagctagcc atgattctca tggacaaaat     180
```

```
tcttcctact tctttggatt gcaagagtat gagaaggacc cttatcaccc tattcaaaac      240
ccctcgggaa ttatacaaat gggtcttgcc gaaaacaagg taattcttga atgtaattaa      300
gttggactac aaccattatt gttcctttg tagtttaact acacatggtc gaatcatttg       360
ttatcaaatg acattgtagt cggttgaaat atattgagta attaagtaag aaaaagatgt      420
aaacgcggat gcatcaaagt aaaccaaat aaaaatatgt tacgtagcaa ttaatttatt       480
taatgaattt tgtaaggttt agttaacggt ttctttata tatgcttgtt atgatcacga       540
tgattatgga ttatggatta tggttttgga ggtagaaaat ttgattgtaa catgtgatat      600
ttaaatgggt tttgcaggta tgtcctgacc ttttggatga gtggatggag aacaatccag      660
atgctttggg attgagaaga aatggagtgt ctgagtttag agaattagct ctatttcaag      720
actatcatgg cttgccagct tttaaaaagg tacctagcct acaaccctag ttttattcat      780
aaagggctct tcaaattttc tttttctttc ttttttatt atttgtttat tattgaaata      840
atatttgata ataataggc gttggttgaa tcaatggaag aaatacgagg aaacaaaatg       900
aaatttgaga tgaacaaact ggtgctaacc gctggtgcaa ctgctgccaa tgaaatcctc      960
atatcttgtc ttgccgatcc cggtgaagcg ttcctcgttc ccactcctta ctatccaggg     1020
taaataaatt caataacttt ccaatatata atcttctct ttttattagt gcgtttgtga      1080
aaatagaaaa aataataagc atatatatga atgtaggttt gacagggact taaaatggcg     1140
tacagaagtt caaataattc caatccattg ttcgagttca aacagcttcc aaatcacaga     1200
agcggcgatg gaggaagcca tggagcaagc ccaaacattg aatttacgag tcaaagggat     1260
tatgattacg aacccatcca acccattagg caccacattg agccagaaag agattaactc     1320
ggtggtggat ttcgctatag ccaatgcaat ccacatcgtg agcgatgaga tatattccgc     1380
cacagttttt gagcacccaa agtttcgaac tgtcatggac ccgaacctac aaaaattccc     1440
aatttgggac cgaatccact ggtgtacag cttgtccaaa gatctgggcc tacccgggtt     1500
ccgcgtgggc atgatttatt caaacgacct agcagtagtg gatgcggcta ccaaaatgtc     1560
tagcttttgt ttagtttctt ctcaaacaca gtattttgtg tcgcaaattg tagggggatga     1620
aaaatttcga ggcaattata tgcaggaaat gaagcggagg attcgaaaga ggagattgat     1680
gttggagtcg agtctccgac agggcggtgt tagatgtttg aaagggaatg cagggttgtt     1740
ttgttgggtg gatatgaggc atcttttgaa gtacccgagt ttcgaagagg aaatggagat     1800
ttggaagacg attttgtatg aggttgggat taatatctct cccggttcgt cttttcattg     1860
ctctgaaccc ggttggttta aatgtgcttt tgccaatatg gaggaacaca ctttcaaggt     1920
ggccatgcat cgtcttaaga cctttctcaa ctctacctca cctctcaatg cctacgaact     1980
ctcccccact aaacgtataa                                                  2000
```

<210> SEQ ID NO 20
<211> LENGTH: 1324
<212> TYPE: DNA
<213> ORGANISM: Citrullus lanatus

<400> SEQUENCE: 20

```
atggcatcct tgtcttctaa agctagccat gattctcatg acaaaattc ttcctacttc        60
tttggattgc aagagtatga gaaggaccct tatcacccta ttcaaaaccc ctcgggaatt      120
atacaaatgg gtcttgccga aaacaaggta tgtcctgacc ttttggatga gtggatggag      180
aacaatccag atgctttggg attgagaaga aatggagtgt ctgagtttag agaattagct      240
ctatttcaag actatcatgg cttgccagct tttaaaaagg cgttggttga atcaatggaa      300
```

-continued

```
gaaatacgag gaaacaaaat gaaatttgag atgaacaaac tggtgctaac cgctggtgca    360
actgctgcca atgaaatcct catatcttgt cttgccgatc ccggtgaagc gttcctcgtt    420
cccactcctt actatccagg gtttgacagg gacttaaaat ggcgtacaga agttcaaata    480
attccaatcc attgttcgag ttcaaacagc ttccaaatca cagaagcggc gatggaggaa    540
gccatggagc aagcccaaac attgaattta cgagtcaaag ggattatgat tacgaaccca    600
tccaacccat taggcaccac attgagccag aaagagatta actcggtggt ggatttcgct    660
atagccaatg caatccacat cgtgagcgat gagatatatt ccgccacagt ttttgagcac    720
ccaaagtttc gaactgtcat ggacccgaac ctacaaaaat tcccaatttg gaccgaatc     780
cacttggtgt acagcttgtc caaagatctg gcctacccg gttccgcgt gggcatgatt      840
tattcaaacg acctagcagt agtggatgcg gctaccaaaa tgtctagctt ttgtttagtt    900
tcttctcaaa cacagtattt tgtgtcgcaa attgtagggg atgaaaaatt tcgaggcaat    960
tatatgcagg aaatgaagcg gaggattcga aagaggagt tgatgttgga gtcgagtctc    1020
cgacagggcg gtgttagatg tttgaaaggg aatgcagggt tgttttgttg ggtggatatg   1080
aggcatcttt tgaagtaccc gagtttcgaa gaggaaatgg agatttggaa gacgattttg   1140
tatgaggttg ggattaatat ctctcccggt tcgtcttttc attgctctga acccggttgg   1200
tttagaatgt gctttgccaa tatggaggaa cacactttca aggtggccat gcatcgtctt   1260
aagacctttc tcaactctac ctcacctctc aatgcctacg aactctcccc cactaaacgt   1320
ataa                                                                1324
```

```
<210> SEQ ID NO 21
<211> LENGTH: 441
<212> TYPE: PRT
<213> ORGANISM: Citrullus lanatus

<400> SEQUENCE: 21

Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30

Pro Ile Gln Asn Pro Ser Gly Ile Ile Gln Met Gly Leu Ala Glu Asn
        35                  40                  45

Lys Val Cys Pro Asp Leu Leu Asp Glu Trp Met Glu Asn Asn Pro Asp
    50                  55                  60

Ala Leu Gly Leu Arg Arg Asn Gly Val Ser Glu Phe Arg Glu Leu Ala
65                  70                  75                  80

Leu Phe Gln Asp Tyr His Gly Leu Pro Ala Phe Lys Lys Ala Leu Val
                85                  90                  95

Glu Ser Met Glu Glu Ile Arg Gly Asn Lys Met Lys Phe Glu Met Asn
            100                 105                 110

Lys Leu Val Leu Thr Ala Gly Ala Thr Ala Ala Asn Glu Ile Leu Ile
        115                 120                 125

Ser Cys Leu Ala Asp Pro Gly Glu Ala Phe Leu Val Pro Thr Pro Tyr
    130                 135                 140

Tyr Pro Gly Phe Asp Arg Asp Leu Lys Trp Arg Thr Glu Val Gln Ile
145                 150                 155                 160

Ile Pro Ile His Cys Ser Ser Asn Ser Phe Gln Ile Thr Glu Ala
                165                 170                 175

Ala Met Glu Glu Ala Met Glu Gln Ala Gln Thr Leu Asn Leu Arg Val
```

```
            180                 185                 190
Lys Gly Ile Met Ile Thr Asn Pro Ser Asn Pro Leu Gly Thr Thr Leu
            195                 200                 205

Ser Gln Lys Glu Ile Asn Ser Val Val Asp Phe Ala Ile Ala Asn Ala
            210                 215                 220

Ile His Ile Val Ser Asp Glu Ile Tyr Ser Ala Thr Val Phe Glu His
225                 230                 235                 240

Pro Lys Phe Arg Thr Val Met Asp Pro Asn Leu Gln Lys Phe Pro Ile
                245                 250                 255

Trp Asp Arg Ile His Leu Val Tyr Ser Leu Ser Lys Asp Leu Gly Leu
            260                 265                 270

Pro Gly Phe Arg Val Gly Met Ile Tyr Ser Asn Asp Leu Ala Val Val
            275                 280                 285

Asp Ala Ala Thr Lys Met Ser Ser Phe Cys Leu Val Ser Ser Gln Thr
290                 295                 300

Gln Tyr Phe Val Ser Gln Ile Val Gly Asp Glu Lys Phe Arg Gly Asn
305                 310                 315                 320

Tyr Met Gln Glu Met Lys Arg Arg Ile Arg Lys Arg Leu Met Leu
                325                 330                 335

Glu Ser Ser Leu Arg Gln Gly Gly Val Arg Cys Leu Lys Gly Asn Ala
            340                 345                 350

Gly Leu Phe Cys Trp Val Asp Met Arg His Leu Leu Lys Tyr Pro Ser
            355                 360                 365

Phe Glu Glu Glu Met Glu Ile Trp Lys Thr Ile Leu Tyr Glu Val Gly
            370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Val Ala
                405                 410                 415

Met His Arg Leu Lys Thr Phe Leu Asn Ser Thr Ser Pro Leu Asn Ala
            420                 425                 430

Tyr Glu Leu Ser Pro Thr Lys Arg Ile
            435                 440

<210> SEQ ID NO 22
<211> LENGTH: 1959
<212> TYPE: DNA
<213> ORGANISM: Luffa acutangula

<400> SEQUENCE: 22
caaagatttc aatatcaata gtcctatacc aaccctaaaa tatattcctc tcctattatc      60
tacctacata ttactgtaca ctcacatatg atggcatcct tgtcttctaa agctagccat     120
gattctcatg gacaaaattc ttcctacttc tttggattgc aagagtatga gaaggaccct     180
tatcacccta ttcaaaaccc ctcgggaatt atacaaatgg gtcttgccga aaacaaggta     240
attcttgaat gtaattaagt tggactacaa ccattattgt tccttttgta gtttaactac     300
acatggtcga atcatttgtt atcaaatgac attgtagtcg gttgaaatat attgagtaat     360
taagtaagaa aaagatgtaa acgcggatgc atcaaagtaa aaccaaataa aaatatgtta     420
cgtagcaatt aatttattta atgaattttg taaggtttag ttaacggttt cttttatata     480
tgcttgttat gatcacgatg attatggatt atgattatg gttttggagg tagaaaattt      540
gattgtaaca tgtgatattt aaatgggttt tgcaggtatg tcctgacctt ttggatgagt     600
ggatggagaa caatccagat gctttgggat tgagaagaaa tggagtgtct gagtttagag     660
```

```
aattagctct atttcaagac tatcatggct tgccagctct aaaaaggta cctagcctac      720 aaccggagtt ttattcataa agggctcttc aaaattcatt tcatcctcac ataatgttag      780
tatgaattat tattgaaata atatttgata ataataggc gttggttgaa tcaatggaag       840
aaatacgagg aaacaaaatg aaatttgaga tgaacaaact ggtgctaacc gctggtgcaa      900
ctgctgccaa tgaaatcctc atatcttgtc ttgccgatcc cggtgaagcg ttcctcgttc      960
ccactcctta ctatccaggg taaataaatt caataacttt ccaatatata aatcttctct     1020
ttttattagt gcgtttgtga aaatagaaaa aataataagc atatatgga atgtaggttt      1080 gacagggact aaaatggcg tacagaagtt caaataattc caatccattg ttcgagttca      1140
aacagcttcc aaatcacaga agcggcgatg gaggaagcca tggagcaagc ccaaacattg     1200
aatttacgag tcaaagggat tatgattacg aacccatcca acccattagg caccacattg     1260
agccagaaag agattaactc ggtggtggat ttcgctatag ccaatgcaat ccacatcgtg     1320
agcgatgaga tatattccgc cacagttttt gagcacccaa agtttcgaac tgtcatggac     1380
ccgaacctac aaaaattccc aatttgggac cgaatccact ggtgtacag cttgtccaaa      1440 gatctgggcc tacccgggtt ccgcgtgggc atgatttatt caaacgacct agcagtagtg     1500
gatgcggcta ccaaaatgtc tagcttttgt ttagtttctt ctcaaacaca gtattttgtg     1560
tcgcaaattg taggggatga aaaatttcga ggcaattata tgcaggaaat gaagcggagg     1620
attcgaaaga ggagattgat gttggagtcg agtctccgac agggcggtgt tagatgtttg     1680
aaagggaatg caggggttgtt ttgttgggtg gatatgaggc atcttttgaa gtacccgagt    1740
ttcgaagagg aaatggagat ttggaagacg attttgtatg aggttgggat taatatctcc     1800
cccggctcat cttttcattg ctctgaacct ggttggttca gaatgtgctt tgctaatatg     1860
gaggagcaca ctttcaagga ggccatgcat cgtcttaagg cctttctcaa ctctacctca     1920
tctctcaacg gccatgaact ctcccccact aacgtataa                            1959

<210> SEQ ID NO 23
<211> LENGTH: 1323
<212> TYPE: DNA
<213> ORGANISM: Luffa acutangula

<400> SEQUENCE: 23
atggcatcct tgtcttctaa agctagccat gattctcatg gacaaaattc ttcctacttc       60
tttggattgc aagagtatga gaaggaccct tatcacccta ttcaaaaccc ctcgggaatt      120
atacaaatgg gtcttgccga aaacaaggta tgtcctgacc ttttggatga gtggatggag      180
aacaatccag atgctttggg attgagaaga aatggagtgt ctgagtttag agaattagct     240
ctatttcaag actatcatgg cttgccagct cttaaaaagg cgttggttga atcaatggaa      300
gaaatacgag gaaacaaaat gaaatttgag atgaacaaac tggtgctaac cgctggtgca     360
actgctgcca tgaaatcctc atatcttgt cttgccgatc ccggtgaagc gttcctcgtt      420
cccactcctt actatccagg gtttgacagg gacttaaaat ggcgtacaga agttcaaata     480
attccaatcc attgttcgag ttcaaacagc ttccaaatca cagaagcggc gatggaggaa     540
gccatggagc aagcccaaac attgaattta cgagtcaaag gattatgat tacgaaccca      600 tccaacccat taggcaccac attgagccag aaagagatta ctcggtggt ggatttcgct     660 atagccaatg caatccacat cgtgagcgat gagatatatt ccgccacagt ttttgagcac     720
ccaaagtttc gaactgtcat ggacccgaac ctacaaaaat tcccaatttg ggaccgaatc     780
```

-continued

```
cacttggtgt acagcttgtc caaagatctg ggcctacccg ggttccgcgt gggcatgatt    840
tattcaaacg acctagcagt agtggatgcg gctaccaaaa tgtctagctt ttgtttagtt    900
tcttctcaaa cacagtattt tgtgtcgcaa attgtagggg atgaaaaatt tcgaggcaat    960
tatatgcagg aaatgaagcg gaggattcga agaggagat tgatgttgga gtcgagtctc   1020
cgacagggcg gtgttagatg tttgaaaggg aatgcagggt tgttttgttg ggtggatatg   1080
aggcatcttt tgaagtaccc gagtttcgaa gaggaaatgg agatttggaa gacgattttg   1140
tatgaggttg ggattaatat ctcccccggc tcatcttttc attgctctga acctggttgg   1200
ttcagaatgt gctttgctaa tatggaggag cacactttca aggaggccat gcatcgtctt   1260
aaggcctttc tcaactctac ctcatctctc aacggccatg aactctcccc cactaacgta   1320
taa                                                                1323
```

<210> SEQ ID NO 24
<211> LENGTH: 440
<212> TYPE: PRT
<213> ORGANISM: Luffa acutangula

<400> SEQUENCE: 24

```
Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30

Pro Ile Gln Asn Pro Ser Gly Ile Ile Gln Met Gly Leu Ala Glu Asn
        35                  40                  45

Lys Val Cys Pro Asp Leu Leu Asp Glu Trp Met Glu Asn Asn Pro Asp
    50                  55                  60

Ala Leu Gly Leu Arg Arg Asn Gly Val Ser Glu Phe Arg Glu Leu Ala
65                  70                  75                  80

Leu Phe Gln Asp Tyr His Gly Leu Pro Ala Leu Lys Lys Ala Leu Val
                85                  90                  95

Glu Ser Met Glu Glu Ile Arg Gly Asn Lys Met Lys Phe Glu Met Asn
            100                 105                 110

Lys Leu Val Leu Thr Ala Gly Ala Thr Ala Ala Asn Glu Ile Leu Ile
        115                 120                 125

Ser Cys Leu Ala Asp Pro Gly Glu Ala Phe Leu Val Pro Thr Pro Tyr
    130                 135                 140

Tyr Pro Gly Phe Asp Arg Asp Leu Lys Trp Arg Thr Glu Val Gln Ile
145                 150                 155                 160

Ile Pro Ile His Cys Ser Ser Asn Ser Phe Gln Ile Thr Glu Ala
                165                 170                 175

Ala Met Glu Glu Ala Met Glu Gln Ala Gln Thr Leu Asn Leu Arg Val
            180                 185                 190

Lys Gly Ile Met Ile Thr Asn Pro Ser Asn Pro Leu Gly Thr Thr Leu
        195                 200                 205

Ser Gln Lys Glu Ile Asn Ser Val Val Asp Phe Ala Ile Ala Asn Ala
    210                 215                 220

Ile His Ile Val Ser Asp Glu Ile Tyr Ser Ala Thr Val Phe Glu His
225                 230                 235                 240

Pro Lys Phe Arg Thr Val Met Asp Pro Asn Leu Gln Lys Phe Pro Ile
                245                 250                 255

Trp Asp Arg Ile His Leu Val Tyr Ser Leu Ser Lys Asp Leu Gly Leu
            260                 265                 270
```

```
Pro Gly Phe Arg Val Gly Met Ile Tyr Ser Asn Asp Leu Ala Val Val
            275                 280                 285

Asp Ala Ala Thr Lys Met Ser Ser Phe Cys Leu Val Ser Ser Gln Thr
        290                 295                 300

Gln Tyr Phe Val Ser Gln Ile Val Gly Asp Glu Lys Phe Arg Gly Asn
305                 310                 315                 320

Tyr Met Gln Glu Met Lys Arg Arg Ile Arg Lys Arg Leu Met Leu
                325                 330                 335

Glu Ser Ser Leu Arg Gln Gly Gly Val Arg Cys Leu Lys Gly Asn Ala
                340                 345                 350

Gly Leu Phe Cys Trp Val Asp Met Arg His Leu Leu Lys Tyr Pro Ser
            355                 360                 365

Phe Glu Glu Glu Met Glu Ile Trp Lys Thr Ile Leu Tyr Glu Val Gly
        370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Glu Ala
                405                 410                 415

Met His Arg Leu Lys Ala Phe Leu Asn Ser Thr Ser Leu Asn Gly
                420                 425                 430

His Glu Leu Ser Pro Thr Asn Val
            435                 440

<210> SEQ ID NO 25
<211> LENGTH: 1963
<212> TYPE: DNA
<213> ORGANISM: Lagenaria siceraria

<400> SEQUENCE: 25
acacacaaag atttcaatat caatagtcct ataccaaccc taaatatat tcctctccta      60 ttatctacct acatattact gtacactcac atatgatggc atccttgtct tctaaagcta    120
gccatgattc tcatggacaa aattcttcct acttctttgg attgcaagag tatgagaagg    180
acccttatca ccctattcaa aaccctcgg gaattataca atgggtctt gccgaaaaca      240 aggtaattct tgaatgtaat taagttggac tacaaccatt attgttcctt ttgtagttta    300
actacacatg gtcgaatcat ttgttatcaa atgacattgt agtcggttga aatatattga    360
gtaattaagt aagaaaaaga gtaaacgcg atgcatcaa agtaaaacca ataaaaata       420 tgttacgtag caattaattt atttaatgaa ttttgtaagg tttagttaac ggtttctttt    480
atatatgctt gttatgatca cgatgattat ggattatgga ttatggtttt ggaggtagaa    540
aatttgattg taacatgtga tatttaaatg ggttttgcag gtatgtcctg acctttggga    600
tgagtgaatg gagaacaatc cagatgcttt gggattgaga gaaatggag tgtctgagtt     660 tagagaatta gctctatttc aagactatca tggcttgcca gcttttaaaa aggtacctag    720
cctacaaccg gtagttttat tcataaaggg ctcttcaaat tttctttttc tttcttttt     780 atttatttgt ttattattga aataatattt gataaataat aggcgttggt tgaatcaatg    840
gaagaaatac gaggaaacaa atgaaattt gagatgaaca aactggtgct aaccgctggt     900
gcaactgctg ccaatgaaat cctcatatct tgtcttgccg atcccggtga agcgttcctc    960
gttcccactc cttactatcc agggtaaata aattcaataa ctttccaata tataaatctt   1020
ctctttttat tagtgcgttt gtgaaaatag aaaaaataat aagcatatat atgaatgtag   1080
gtttgacagg gacttaaaat ggcgtacaga agttcaaata attccaatcc attgttcgag   1140
```

| | |
|---|---|
| ttcaaacagc ttccaaatca cagaagcggc gatggaggaa gccatggagc aagcccaaac | 1200 |
| attgaattta cgagtcaaag ggattatgat tacgaaccca tccaacccat taggcaccac | 1260 |
| attgagccag aaagagatta actcggtggt ggatttcgct atagccaatg caatccacat | 1320 |
| cgtgagcgat gagatatatt ccgccacagt ttttgagcac ccaaagtttc gaactgtcat | 1380 |
| ggacccgaac ctacaaaaat tcccaatttg gaccgaatc cacttggtgt acagcttgtc | 1440 |
| caaagatctg ggcctacccg ggttccgcgt gggcatgatt tattcaaacg acctagcagt | 1500 |
| agtggatgcg gctaccaaaa tgtctagctt ttgtttagtt tcttctcaaa cacagtattt | 1560 |
| tgtgtcgcaa attgtagggg atgaaaaatt tcgaggcaat tatatgcagg aaatgaagcg | 1620 |
| gaggattcga agaggagat tgatgttgga gtcgagtctc cgacagggcg tgttagatg | 1680 |
| tttgaaaggg aatgcagggt tgttttgttg ggtggatatg aggcatcttt tgaagtaccc | 1740 |
| gagtttcgaa gaggaaatgg agatttggaa gacgattttg tatgaggttg ggattaatat | 1800 |
| ctcccccggc tcatcttttc attgctctga acctggttgg ttcagaatgt gctttgctaa | 1860 |
| tatggaggag cacactttca aggaggccat gcatcgtctt aaggcctttc tcaactctac | 1920 |
| ctcatctctc aacggccatg aactctcccc cactaacgta taa | 1963 |

<210> SEQ ID NO 26
<211> LENGTH: 1323
<212> TYPE: DNA
<213> ORGANISM: Lagenaria siceraria

<400> SEQUENCE: 26

| | |
|---|---|
| atggcatcct tgtcttctaa agctagccat gattctcatg acaaaattc ttcctacttc | 60 |
| tttggattgc aagagtatga gaaggaccct tatcaccccta ttcaaaaccc ctcgggaatt | 120 |
| atacaaatgg gtcttgccga aaacaaggta tgtcctgacc ttttggatga gtgaatggag | 180 |
| aacaatccag atgctttggg attgagaaga aatggagtgt ctgagtttag agaattagct | 240 |
| ctatttcaag actatcatgg cttgccagct tttaaaaagg cgttggttga atcaatggaa | 300 |
| gaaatacgag gaaacaaaat gaaatttgag atgaacaaac tggtgctaac cgctggtgca | 360 |
| actgctgcca atgaaatcct catatcttgt cttgccgatc ccggtgaagc gttcctcgtt | 420 |
| cccactcctt actatccagg gtttgacagg gacttaaaat ggcgtacaga agttcaaata | 480 |
| attccaatcc attgttcgag ttcaaacagc ttccaaatca cagaagcggc gatggaggaa | 540 |
| gccatggagc aagcccaaac attgaattta cgagtcaaag ggattatgat tacgaaccca | 600 |
| tccaacccat taggcaccac attgagccag aaagagatta actcggtggt ggatttcgct | 660 |
| atagccaatg caatccacat cgtgagcgat gagatatatt ccgccacagt ttttgagcac | 720 |
| ccaaagtttc gaactgtcat ggacccgaac ctacaaaaat tcccaatttg gaccgaatc | 780 |
| cacttggtgt acagcttgtc caaagatctg ggcctacccg ggttccgcgt gggcatgatt | 840 |
| tattcaaacg acctagcagt agtggatgcg gctaccaaaa tgtctagctt ttgtttagtt | 900 |
| tcttctcaaa cacagtattt tgtgtcgcaa attgtagggg atgaaaaatt tcgaggcaat | 960 |
| tatatgcagg aaatgaagcg gaggattcga agaggagat tgatgttgga gtcgagtctc | 1020 |
| cgacagggcg tgttagatg tttgaaaggg aatgcagggt tgttttgttg ggtggatatg | 1080 |
| aggcatcttt tgaagtaccc gagtttcgaa gaggaaatgg agatttggaa gacgattttg | 1140 |
| tatgaggttg ggattaatat ctcccccggc tcatcttttc attgctctga acctggttgg | 1200 |
| ttcagaatgt gctttgctaa tatggaggag cacactttca aggaggccat gcatcgtctt | 1260 |
| aaggcctttc tcaactctac ctcatctctc aacggccatg aactctcccc cactaacgta | 1320 |

-continued

```
taa                                                                    1323
```

<210> SEQ ID NO 27
<211> LENGTH: 440
<212> TYPE: PRT
<213> ORGANISM: Lagenaria siceraria
<220> FEATURE:
<221> NAME/KEY: misc_feature
<222> LOCATION: (58)..(58)
<223> OTHER INFORMATION: Xaa can be any naturally occurring amino acid

<400> SEQUENCE: 27

```
Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30

Pro Ile Gln Asn Pro Ser Gly Ile Ile Gln Met Gly Leu Ala Glu Asn
        35                  40                  45

Lys Val Cys Pro Asp Leu Leu Asp Glu Xaa Met Glu Asn Asn Pro Asp
    50                  55                  60

Ala Leu Gly Leu Arg Arg Asn Gly Val Ser Glu Phe Arg Glu Leu Ala
65                  70                  75                  80

Leu Phe Gln Asp Tyr His Gly Leu Pro Ala Phe Lys Lys Ala Leu Val
                85                  90                  95

Glu Ser Met Glu Glu Ile Arg Gly Asn Lys Met Lys Phe Glu Met Asn
            100                 105                 110

Lys Leu Val Leu Thr Ala Gly Ala Thr Ala Ala Asn Glu Ile Leu Ile
        115                 120                 125

Ser Cys Leu Ala Asp Pro Gly Glu Ala Phe Leu Val Pro Thr Pro Tyr
    130                 135                 140

Tyr Pro Gly Phe Asp Arg Asp Leu Lys Trp Arg Thr Glu Val Gln Ile
145                 150                 155                 160

Ile Pro Ile His Cys Ser Ser Asn Ser Phe Gln Ile Thr Glu Ala
                165                 170                 175

Ala Met Glu Glu Ala Met Glu Gln Ala Gln Thr Leu Asn Leu Arg Val
            180                 185                 190

Lys Gly Ile Met Ile Thr Asn Pro Ser Asn Pro Leu Gly Thr Thr Leu
        195                 200                 205

Ser Gln Lys Glu Ile Asn Ser Val Val Asp Phe Ala Ile Ala Asn Ala
    210                 215                 220

Ile His Ile Val Ser Asp Glu Ile Tyr Ser Ala Thr Val Phe Glu His
225                 230                 235                 240

Pro Lys Phe Arg Thr Val Met Asp Pro Asn Leu Gln Lys Phe Pro Ile
                245                 250                 255

Trp Asp Arg Ile His Leu Val Tyr Ser Leu Ser Lys Asp Leu Gly Leu
            260                 265                 270

Pro Gly Phe Arg Val Gly Met Ile Tyr Ser Asn Asp Leu Ala Val Val
        275                 280                 285

Asp Ala Ala Thr Lys Met Ser Ser Phe Cys Leu Val Ser Ser Gln Thr
    290                 295                 300

Gln Tyr Phe Val Ser Gln Ile Val Gly Asp Lys Phe Arg Gly Asn
305                 310                 315                 320

Tyr Met Gln Glu Met Lys Arg Arg Ile Arg Lys Arg Leu Met Leu
                325                 330                 335

Glu Ser Ser Leu Arg Gln Gly Gly Val Arg Cys Leu Lys Gly Asn Ala
```

```
            340                 345                 350
Gly Leu Phe Cys Trp Val Asp Met Arg His Leu Leu Lys Tyr Pro Ser
            355                 360                 365

Phe Glu Glu Glu Met Glu Ile Trp Lys Thr Ile Leu Tyr Glu Val Gly
        370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Glu Ala
                405                 410                 415

Met His Arg Leu Lys Ala Phe Leu Asn Ser Thr Ser Ser Leu Asn Gly
            420                 425                 430

His Glu Leu Ser Pro Thr Asn Val
            435                 440
```

<210> SEQ ID NO 28
<211> LENGTH: 1961
<212> TYPE: DNA
<213> ORGANISM: Momordica charentia

<400> SEQUENCE: 28

| | | | | | |
|---|---|---|---|---|---|
| aaccacaaag | atttcaatat | caatagtcct | ataccaaccc | taaatatatat | tcctctccta | 60 |
| ttatctacct | acatattact | gtacactcac | atatgatggc | atccttgtct | tctaaagcta | 120 |
| gccatgattc | tcatggacaa | aattcttcct | acttctttgg | attgcaagag | tatgagaagg | 180 |
| acccttatca | ccctattcaa | aacccctcgg | gaattataca | aatgggtctt | gccgaaaaca | 240 |
| aggtaattct | tgaatgtaat | taagttggac | tacaaccatt | attgttcctt | ttgtagttta | 300 |
| actacacatg | gtcgaatcat | ttgttatcaa | atgacattgt | agtcggttga | aatatattga | 360 |
| gtaattaagt | aagaaaaaga | tgtaaacgcg | gatgcatcaa | agtaaaacca | aataaaaata | 420 |
| tgttacgtag | caattaattt | atttaatgaa | ttttgtaagg | tttagttaac | ggtttctttt | 480 |
| atatatgctt | gttatgatca | cgatgattat | ggattatgga | ttatggtttt | ggaggtagaa | 540 |
| aatttgattg | taacatgtga | tatttaaatg | ggttttgcag | gtatgtcctg | accttttgga | 600 |
| tgagtggatg | gagaacaatc | cagatgcttt | gggattgaga | agaaatggag | tgtctgagtt | 660 |
| tagagaatta | gctctatttc | aagactatca | tggcttgcca | gcttttaaaa | aggtacctag | 720 |
| cctacaaccc | tagttttatt | cataaagggc | tcttcaaatt | ttcttttctt | tcttttattt | 780 |
| atttgtttac | tattgaagta | atataaataa | taaataatag | gtgttggttg | aatcaatgga | 840 |
| agaaatacga | ggaaacaaaa | tgaaatttga | gatgaacaaa | ctggtgctaa | ccgctggtgc | 900 |
| aactgctgcc | aatgaaatcc | tcatatcttg | tcttgccgat | cccggtgaag | cgttcctcgt | 960 |
| tcccactcct | tactatccag | ggtaaataaa | ttcaataact | ttccaatata | taaatcttct | 1020 |
| cttttattta | gtgcgtttgt | gaaaatagaa | aaaataataa | gcatatatat | gaatgtaggt | 1080 |
| ttgacaggga | cttaaaatgg | cgtacagaag | ttcaaataat | tccaatccat | tgttcgagtt | 1140 |
| caaacagctt | ccaaatcaca | gaagcggcga | tggaggaagc | catggagcaa | gcccaaacat | 1200 |
| tgaatttacg | agtcaaaggg | attatgatta | cgaacccatc | caacccatta | ggcaccacat | 1260 |
| tgagccagaa | agagattaac | tcggtggtgg | atttcgctat | agccaatgca | atccacatcg | 1320 |
| tgagcgatga | gatatattcc | gccacagttt | ttgagcaccc | aaagtttcga | actgtcatgg | 1380 |
| acccgaacct | acaaaaattc | ccaatttggg | accgaatcca | cttggtgtac | agcttgtcca | 1440 |
| aagatctggg | cctacccggg | ttccgcgtgg | gcatgattta | ttcaaacgac | ctagcagtag | 1500 |
| tggatgcggc | taccaaaatg | tctagctttt | gtttagtttc | ttctcaaaca | cagtattttg | 1560 |

```
tgtcgcaaat tgtaggggat gaaaaatttc gaggcaatta tatgcaggaa atgaagcgga    1620
ggattcgaaa gaggagattg atgttggagt cgagtctccg acagggcggt gttagatgtt    1680
tgaaagggaa tgcagggttg ttttgttggg tggatatgag gcatcttttg aagtacccga    1740
gtttcgaaga ggaaatggag atttggaaga cgattttgta tgaggttggg attaatatct    1800
cccccggctc atcctttcat tgctctgaac ctggttggtt cagaatgtgc tttgctaata    1860
tggaggagca cactttcaag gaggccatgc atcgtcttaa ggcctttctc aactctacct    1920
catctctcaa cggccatgaa ctctccccca ctaacgtata a                        1961

<210> SEQ ID NO 29
<211> LENGTH: 1323
<212> TYPE: DNA
<213> ORGANISM: Momordica charentia

<400> SEQUENCE: 29
atggcatcct tgtcttctaa agctagccat gattctcatg gacaaaattc ttcctacttc      60
tttggattgc aagagtatga gaaggaccct tatcacccta ttcaaaaccc ctcgggaatt     120
atacaaatgg gtcttgccga aaacaaggta tgtcctgacc ttttggatga gtggatggag     180
aacaatccag atgctttggg attgagaaga aatggagtgt ctgagtttag agaattagct     240
ctatttcaag actatcatgg cttgccagct tttaaaaagg tgttggttga atcaatggaa     300
gaaatacgag gaaacaaaat gaaatttgag atgaacaaac tggtgctaac cgctggtgca     360
actgctgcca atgaaatcct catatcttgt cttgccgatc ccggtgaagc gttcctcgtt     420
cccactcctt actatccagg gtttgacagg gacttaaaat ggcgtacaga agttcaaata     480
attccaatcc attgttcgag ttcaaacagc ttccaaatca cagaagcggc gatggaggaa     540
gccatggagc aagcccaaac attgaattta cgagtcaaag ggattatgat tacgaaccca     600
tccaacccat taggcaccac attgagccag aaagagatta ctcggtggt ggatttcgct      660 atagccaatg caatccacat cgtgagcgat gagatatatt ccgccacagt ttttgagcac     720
ccaaagtttc gaactgtcat ggacccgaac ctacaaaaat tcccaatttg gaccgaatc     780 cacttggtgt acagcttgtc caaagatctg gcctacccg ggttccgcgt gggcatgatt      840
tattcaaacg acctagcagt agtggatgcg gctaccaaaa tgtctagctt tgtttagtt     900 tcttctcaaa cacagtattt tgtgtcgcaa attgtagggg atgaaaaatt tcgaggcaat     960
tatatgcagg aaatgaagcg gaggattcga agaggagat tgatgttgga gtcgagtctc     1020
cgacagggcg tgttagatg tttgaaaggg aatgcagggt tgttttgttg ggtggatatg     1080
aggcatcttt tgaagtaccc gagtttcgaa ggaaatggag atttggaaga cgattttgta    1140 tgaggttgg gattaatat ctcccccggc tcatcctttc attgctctga acctggttgg      1200
ttcagaatgt gctttgctaa tatggaggag cacactttca aggaggccat gcatcgtctt    1260
aaggcctttc tcaactctac ctcatctctc aacggccatg aactctcccc cactaacgta    1320
taa                                                                  1323

<210> SEQ ID NO 30
<211> LENGTH: 440
<212> TYPE: PRT
<213> ORGANISM: Momordica charentia

<400> SEQUENCE: 30

Met Ala Ser Leu Ser Ser Lys Ala Ser His Asp Ser His Gly Gln Asn
1               5                   10                  15
```

Ser Ser Tyr Phe Phe Gly Leu Gln Glu Tyr Glu Lys Asp Pro Tyr His
        20                  25                  30

Pro Ile Gln Asn Pro Ser Gly Ile Ile Gln Met Gly Leu Ala Glu Asn
            35                  40                  45

Lys Val Cys Pro Asp Leu Leu Asp Glu Trp Met Glu Asn Asn Pro Asp
 50                  55                  60

Ala Leu Gly Leu Arg Arg Asn Gly Val Ser Glu Phe Arg Glu Leu Ala
 65                  70                  75                  80

Leu Phe Gln Asp Tyr His Gly Leu Pro Ala Phe Lys Lys Val Leu Val
                 85                  90                  95

Glu Ser Met Glu Glu Ile Arg Gly Asn Lys Met Lys Phe Glu Met Asn
            100                 105                 110

Lys Leu Val Leu Thr Ala Gly Ala Thr Ala Ala Asn Glu Ile Leu Ile
            115                 120                 125

Ser Cys Leu Ala Asp Pro Gly Glu Ala Phe Leu Val Pro Thr Pro Tyr
130                 135                 140

Tyr Pro Gly Phe Asp Arg Asp Leu Lys Trp Arg Thr Glu Val Gln Ile
145                 150                 155                 160

Ile Pro Ile His Cys Ser Ser Asn Ser Phe Gln Ile Thr Glu Ala
                165                 170                 175

Ala Met Glu Glu Ala Met Glu Gln Ala Gln Thr Leu Asn Leu Arg Val
            180                 185                 190

Lys Gly Ile Met Ile Thr Asn Pro Ser Asn Pro Leu Gly Thr Thr Leu
            195                 200                 205

Ser Gln Lys Glu Ile Asn Ser Val Val Asp Phe Ala Ile Ala Asn Ala
            210                 215                 220

Ile His Ile Val Ser Asp Glu Ile Tyr Ser Ala Thr Val Phe Glu His
225                 230                 235                 240

Pro Lys Phe Arg Thr Val Met Asp Pro Asn Leu Gln Lys Phe Pro Ile
                245                 250                 255

Trp Asp Arg Ile His Leu Val Tyr Ser Leu Ser Lys Asp Leu Gly Leu
            260                 265                 270

Pro Gly Phe Arg Val Gly Met Ile Tyr Ser Asn Asp Leu Ala Val Val
            275                 280                 285

Asp Ala Ala Thr Lys Met Ser Ser Phe Cys Leu Val Ser Ser Gln Thr
290                 295                 300

Gln Tyr Phe Val Ser Gln Ile Val Gly Asp Gly Lys Phe Arg Gly Asn
305                 310                 315                 320

Tyr Met Gln Glu Met Lys Arg Arg Ile Arg Lys Arg Leu Met Leu
                325                 330                 335

Glu Ser Ser Leu Arg Gln Gly Gly Val Arg Cys Leu Lys Gly Asn Ala
            340                 345                 350

Gly Leu Phe Cys Trp Val Asp Met Arg His Leu Leu Lys Tyr Pro Ser
            355                 360                 365

Phe Glu Glu Glu Met Glu Ile Trp Lys Thr Ile Leu Tyr Glu Val Gly
            370                 375                 380

Ile Asn Ile Ser Pro Gly Ser Ser Phe His Cys Ser Glu Pro Gly Trp
385                 390                 395                 400

Phe Arg Met Cys Phe Ala Asn Met Glu Glu His Thr Phe Lys Glu Ala
                405                 410                 415

Met His Arg Leu Lys Ala Phe Leu Asn Ser Thr Ser Ser Leu Asn Gly
            420                 425                 430

```
His Glu Leu Ser Pro Thr Asn Val
        435                 440

<210> SEQ ID NO 31
<211> LENGTH: 1869
<212> TYPE: DNA
<213> ORGANISM: Cucurbita pepo
<220> FEATURE:
<221> NAME/KEY: misc_feature
<222> LOCATION: (763)..(765)
<223> OTHER INFORMATION: n = a, t, g or c
<220> FEATURE:
<221> NAME/KEY: misc_feature
<222> LOCATION: (798)..(799)
<223> OTHER INFORMATION: n = a, t, g or c
<220> FEATURE:
<221> NAME/KEY: misc_feature
<222> LOCATION: (801)..(1068)
<223> OTHER INFORMATION: n = a, t, g or c
<220> FEATURE:
<221> NAME/KEY: misc_feature
<222> LOCATION: (1604)..(1605)
<223> OTHER INFORMATION: n = a, t, g or c
<220> FEATURE:
<221> NAME/KEY: misc_feature
<222> LOCATION: (1704)..(1869)
<223> OTHER INFORMATION: n = a, t, g or c

<400> SEQUENCE: 31
aaatgtcact ctaaattccc cacacaaaca cacaaagatt tcaatatcaa tagtcctata      60
ccaaccctaa aatatattcc tctcctatta tctacctaca tattactgta cactcacata    120
tgatggcatc cttgtcttct aaagctagcc atgattctca tggacaaaat tcttcctact    180
tctttggatt gcaagagtat gagaaggacc cttatcaccc tattcaaaac ccctcgggaa    240
ttatacaaat gggtcttgcc gaaaacaagg taattcttga atgtaattaa gttggactac    300
aaccattatt gttccttttg tagtttaact acacatggtc gaatcatttg ttatcaaatg    360
acattgtagt cggttgaaat atattgagta attaagtaag aaaagatgt aaacgcggat     420
gcatcaaagt aaaccaaat aaaaatatgt tacgtagcaa ttaatttatt taatgaattt    480
tgtaaggttt agttaacggt ttcttttata tatgcttgtt atgatcacga tgattatgga    540
ttatggatta tggttttgga ggtagaaaat ttgattgtaa catgtgatat ttaaatgggt    600
tttgcaggta tgtcctgacc ttttggatga gtggatggag aacaatccag atgctttggg    660
attgagaaga aatggagtgt ctgagtttag agaattagct ctatttcaag actatcatgg    720
cttgccagct tttaaaaagg tacctagcct acaaccctag ttnnntcata aagggctctt    780
caaatttctt tcttttttnnc nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnga gtaaaagaca   1080
attattcaat aaggttgctc tagtgtaagt gcttcataat aacacgtgga ttcgaaagag   1140
caggtttgac cgggacctaa aatggcgtac gcatgttcaa ataattccaa ttcactgttg   1200
gagttcaaac gggttcagaa tcacagcagc ggccatggag gaggcatgg aacgagccga    1260
aaagctgaat ctacgagtga aggggttttt aatcacgaac ccatcaaacc cattgggcac   1320
tacaatgagc cggaacgagc tgaatttagt ggtggatttc gccaaagcca aggaatcca    1380
cattgtaagc gacgagatat attccgccac agtttatgag accccaaagt tcagaaccat   1440
```

```
aatggacgat agcctaaaaa aatcctcaat atgggaccga atccacgtgg tttacagcct   1500
gtccaaggat ctgggcctac ccgggttccg agtaggtatg atttattcaa acaacccgaa   1560
agtggtggct gcggctacca aaatgtcaag cttcggtctg gtgnngtctc agacgcagta   1620
cttgctgtct caaattctgg gggacgagaa attccgaagg aattacatgg aggaaacgaa   1680
gagacggatc cggaagagga aagnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860 nnnnnnnnn                                                            1869

<210> SEQ ID NO 32
<211> LENGTH: 1245
<212> TYPE: DNA
<213> ORGANISM: Cucurbita pepo
<220> FEATURE:
<221> NAME/KEY: misc_feature
<222> LOCATION: (280)..(534)
<223> OTHER INFORMATION: n = a, t, g or c
<220> FEATURE:
<221> NAME/KEY: misc_feature
<222> LOCATION: (995)..(996)
<223> OTHER INFORMATION: n = a, t, g or c
<220> FEATURE:
<221> NAME/KEY: misc_feature
<222> LOCATION: (1094)..(1245)
<223> OTHER INFORMATION: n = a, t, g or c

<400> SEQUENCE: 32
atggcatcct tgtcttctaa agctagccat gattctcatg acaaaattc ttcctacttc     60 tttggattgc aagagtatga gaaggaccct tatcacccta ttcaaaaccc ctcgggaatt   120
atacaaatgg gtcttgccga aaacaaggta tgtcctgacc ttttggatga gtggatggag   180
aacaatccag atgctttggg attgagaaga aatggagtgt ctgagtttag agaattagct   240
ctatttcaag actatcatgg cttgccagct tttaaaaagn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnngtttga   540
ccgggaccta aaatggcgta cgcatgttca ataattcca attcactgtt ggagttcaaa    600
cgggttcaga atcacagcag cggccatgga ggaggccatg gaacgagccg aaaagctgaa   660
tctacgagtg aaggggtttt taatcacgaa cccatcaaac ccattgggca ctacaatgag   720
ccggaacgag ctgaatttag tggtggattt cgccaaagcc aaaggaatcc acattgtaag   780
cgacgagata tattccgcca cagtttatga daccccaaag ttcagaacca taatggacga   840
tagcctaaaa aaatcctcaa tatgggaccg aatccacgtg gtttacagcc tgtccaagga   900
tctgggccta cccgggttcc gagtaggtat gatttattca acaacccga aagtggtggc    960 tgcggctacc aaaatgtcaa gcttcggtct ggtgnngtct cagacgcagt acttgctgtc   1020
tcaaattctg ggggacgaga aattccgaag gaattacatg gaggaaacga agagacggat   1080
ccggaagagg aaagnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnn                    1245
```

```
<210> SEQ ID NO 33
<211> LENGTH: 558
<212> TYPE: PRT
<213> ORGANISM: Cucurbita pepo
<220> FEATURE:
<221> NAME/KEY: MISC_FEATURE
<222> LOCATION: (94)..(372)
<223> OTHER INFORMATION: X = G, P, A, V, L, I, M, C, F, Y, W, H, K, R,
      Q, N, E, D, S or T
<220> FEATURE:
<221> NAME/KEY: MISC_FEATURE
<222> LOCATION: (526)..(526)
<223> OTHER INFORMATION: X = G, P, A, V, L, I, M, C, F, Y, W, H, K, R,
      Q, N, E, D, S or T

<400> SEQUENCE: 33
```

Met Ala Ser Leu Ser Ser Lys Ala Ser His Asp Ser His Gly Gln Asn
1               5                   10                  15

Ser Ser Tyr Phe Phe Gly Leu Gln Glu Tyr Glu Lys Asp Pro Tyr His
            20                  25                  30

Pro Ile Gln Asn Pro Ser Gly Ile Ile Gln Met Gly Leu Ala Glu Asn
        35                  40                  45

Lys Val Cys Pro Asp Leu Leu Asp Glu Trp Met Glu Asn Asn Pro Asp
50                  55                  60

Ala Leu Gly Leu Arg Arg Asn Gly Val Ser Glu Phe Arg Glu Leu Ala
65                  70                  75                  80

Leu Phe Gln Asp Tyr His Gly Leu Pro Ala Phe Lys Lys Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

```
Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa
        355                 360                 365

Xaa Xaa Xaa Xaa Phe Asp Arg Asp Leu Lys Trp Arg Thr His Val Gln
370                 375                 380

Ile Ile Pro Ile His Cys Trp Ser Ser Asn Gly Phe Arg Ile Thr Ala
385                 390                 395                 400

Ala Ala Met Glu Glu Ala Met Glu Arg Ala Glu Lys Leu Asn Leu Arg
                405                 410                 415

Val Lys Gly Val Leu Ile Thr Asn Pro Ser Asn Pro Leu Gly Thr Thr
            420                 425                 430

Met Ser Arg Asn Glu Leu Asn Leu Val Val Asp Phe Ala Lys Ala Lys
        435                 440                 445

Gly Ile His Ile Val Ser Asp Glu Ile Tyr Ser Ala Thr Val Tyr Glu
    450                 455                 460

Thr Pro Lys Phe Arg Thr Ile Met Asp Asp Ser Leu Lys Lys Ser Ser
465                 470                 475                 480

Ile Trp Asp Arg Ile His Val Val Tyr Ser Leu Ser Lys Asp Leu Gly
                485                 490                 495

Leu Pro Gly Phe Arg Val Gly Met Ile Tyr Ser Asn Asn Pro Lys Val
            500                 505                 510

Val Ala Ala Ala Thr Lys Met Ser Ser Phe Gly Leu Val Xaa Ser Gln
        515                 520                 525

Thr Gln Tyr Leu Leu Ser Gln Ile Leu Gly Asp Glu Lys Phe Arg Arg
    530                 535                 540

Asn Tyr Met Glu Glu Thr Lys Arg Arg Ile Arg Lys Arg Lys
545                 550                 555
```

<210> SEQ ID NO 34
<211> LENGTH: 5000
<212> TYPE: DNA
<213> ORGANISM: Citrullus lanatus

<400> SEQUENCE: 34

```
tgacgttatt tttgcggact tcaattacta gataatatct ccaaaacaaa agaagaagag    60
aaaaaaaaaa aaaaaaaaaa aaaaaaacga atggagatca aagacagttt ttagagtagc   120
aacctgaatc aggaattttg tttaaagtta aagggataca tctcctttat tctggcttta   180
ccttgtccta agaaacaaaa aaaaaaaaat tcaatgataa acctcggtga tatatgtttt   240
acaccatttg acgcagtaca ttacctcagg ggacaatgaa agctatatct ttttatcatg   300
ttttctaagt cccacaaaat tcttaaatat tattaatcta ctttaccaac atatatatat   360
ttacacataa cccttaatt aacttcacat accataccac aaaagaaaga aaagtcaatg   420
gctgggacag gtgctgtttt gatccgcagg agccattttg ttctacctga ttgtcggtga   480
aatatctcaa tatgcaaaag catacacggc ttctctcttt atattcccat gcgtcacctc   540
tttaaattac cacccaacta atttattcta cttttcaatt attacctttt acatttttca   600
actccccgga tttgtatttt cattttcaa cccttcaa tcaaattaa tttacaactt   660
tcacctaacc caattccctc taagacaggt aatcaaatat ggaaatact tcatcagttc   720
ttttcaattt cttcctctca cttttctacc tactaatagg aaaaaaaaaa aaaaaaaatc   780
aaatccttct tggatttgca tttaaatctt ttctaagttg aagtttgaaa aaatgttgct   840
```

```
atttgctaca agatgattat ttgacttaga gcagccaacc ccataatatc taatcatgta     900
ttcaaataaa gtgcgaagaa agaaagaaag gaaaaaaaaa aaaaaaaccc aaaagcaagt     960
tacaagagag agacaattaa tcaataaact ccaaaattgt ctgtttgtgg aaaaaaaaat    1020
caactcttta atttcataca ccctaaacct cctctcctcc ctatatatat ataaatgtca    1080
ctctaaactc tccacacaaa cacacaagat ttcaatatca atagctttat acaaccctaa    1140
aatatttcct ctccgtctcc tataatctac ctacatattg tacactttga tcattcataa    1200
acatatatat atatatatga tggcaatgtt gtctaccaaa gctagccatg attctcatgg    1260
tcaagattct tcctactttt taggatggca agaatatgag aagaacccat atcaccctac    1320
tcgaaccccc accggaatta tccaaatggg tctcgccgaa acaaggtaa ttctccaccg     1380 ttggttgaat tgcaactatt attccttttg tagtccaact acatggtcaa atcgtgattt    1440
gggctattga ttagccagct aatagtcgag tagtactttt ttttttttt tttttcatcct   1500 acatgataat ctcgttatta tcattaacgt ataattatga tattaatggt tttgcagcta    1560
tgttatgact tattggatga gtggatggag aacaatccag acgctttggg attgagaaga    1620
aatggagtgt ctgtgtttag agaattggct ctatttcaag actatcatgg cttgcctgct    1680
tttaaaaagg tagctactgg ctagcctact tttttcataa agggaatatt caattttttt    1740 tttctttta atattattga aattaatatt gtatgtgata ataaataata ataggtgttg    1800
gttgaattaa tggaggaaat acgaggaaag aaagtgagat ttgatatgaa taaactggtc    1860
ctcaccgctg gtgcaacttc tgcgaatgag atcctaatgt tttgtcttgc cgaacctggt    1920
gaagctttcc ttgttcccac tccttactat cctgggtaat taacctccat tatcactttt    1980
ttttccacaa aaaaatttaa aaaaaaaact caattatttg tgcatgtgta ccatgtaaac    2040
catacatttt actgccaata attttttgcat aaatcatgca tacaaaattt aaaattatgg   2100
atattggtga tgccaaaatc tcaaccggaa aatatacacc taactttgac ttttacttaa    2160
caataatggt aaagaattta acttacaaga aggaaatata tatttgcaca ttggtgtagt    2220
acttaaatta gaaagtgtaa ctgtgcaaca ggtaaaagtt ttgaatatta ggtgtaattg    2280
acttaggccc tttcttatta ggattttaaa gttgcattgg aattatccct ttgactcact    2340 acattgggt gtacttgttt ggtattttgt gggattgacc tttgccaaag ttgaagctaa     2400
acaccttctt ttaactatat tttgggtcta agatgatccc ttaagtcgaa gcatgcatga    2460
gtcatgtccc attaggggtg tttgggataa tatatggaat aatgaaaagt aagaatgtta    2520
tgaaatcaag ggtttatgaa ctcttttggat ccctagtata caaagttgat aagatataaa   2580
actgatgttt ttctagtagt tggacccacc aaccccttga gccaaacaag aagtgcacaa    2640
ctcacaaact cctactcccc aacttgttgg gccaaacata ctctaagcat ttgtgaggc     2700 aggtcgaggt caagcatact ggtttaggtc gaggcccaag ccagcccatt ttagtcctaa    2760
cttgccatgt tcgactcggc ttgagtcaat ttttgttata tgttagatta tgttttttga    2820
tttcactttc ataagttt tttaatggtg gttttgtaag tattagtaag atttggaatt     2880
ttattgatta aaaatataat gcaggtttga cagagactta aaatggcgta caggcgtacg    2940
aataattcca attcagtgtt caagttcaaa cggtttccga atcaccgcag cggcaatgga    3000
agaagcgagg gaacgagccc aaaagctgaa attacgagtc aaaggggttt taatcacgaa    3060
cccatcgaat ccactgggaa ccacattgag ctgcaaggag ctgaatttag tggtgaattt    3120
cgccacagcc aacgcaatac acatagtgag cgacagagata tattcggcca cagttttctc    3180
atccccaaat ttccaaaacca tcatggacca acgcctacaa aaatcccaa tttgggagcg    3240
```

```
catccacgtg gtgtacagcc tatccaagga tctaggcttg cctgggttcc gcgtaggcat    3300
gatttattca aacaaccca aagtagtggc tgcagctacc aaaatgtcga gctttggtct    3360
agtttcatct cagacacaat atttggtgtc acaaatgcta ggagacccca aattccgaga    3420
gaattacatg acggaaatga agatgaggat caggaagagg aaaggaatgt tggagttggg    3480
gctccgaaaa gccggaatca ggtgtttgaa agggaatgcg ggtttgtttt gttgggtgga    3540
tatgaggcat cttttaaaat atccaagttt ccaacaggaa atggagtttt ggaagaggat    3600
tttgtgtgag gttgggctta atgtctcgcc cggttcggct tgtcattgtt ctgaaccggg    3660
ttggttcaga atgtgctttg ctaacatgtc ggaacacact tgatggtgg cgatgtgtcg    3720 tcttaaggca tttgtggagt ctaccttatc tctcaaaggc caccagaagg tcttccttaa    3780
ctaagtggta attgggcac cacagtagcc taatatgcac aaaatttctt ctttcggctt    3840
tgcttcttta ttaccctaat taattaattt atccatctaa tctaatatat gtaactagtt    3900
taattaaatt ttagtaataa tgttcttgat atcaactaat tgcctattaa attgttatat    3960
atttaaagtt tatgggcgag gggctaaaat tcattttatg atgagatcac ttctcaaaaa    4020
ccaatgtcta ttctgttttt aatgatgatg ataataataa cttaggtgta ttcaattcgg    4080
ttaagtgagc acgatacatt tagttattat caaccaacca aactataatt gttttcctct    4140
aaaaggaagg aaactaaata aatatagcat aactcatgag attttttttt gtttgaagag    4200
gcataactcg agatattagt aacttattta attgtaaaag attcaaatct ttctatctcg    4260
tatttataat gttatatata ttttgaagac gtactttttt cttcacgaga ttttttttt    4320 tgtttgaaga ggcataactc gagatattag taacttattt aattgtaaaa tattcaaatc    4380
tttctatctc gtatttataa tgttatatat attttgaaga cgtactttt tcttcaacaa    4440 tatacgaggt ggaagattca aacttctaat atcttgatcg atagataata ttttgtactt    4500
gttgaaatat actcattgtg cttaaaaaa acacttcaat tgattgcatt atttataatg    4560
tatatactat gtttgtattt attattccat cttatgcaaa tatgtattcc ttggatttca    4620
tcatatacgt tggatatatt tactcatttg aaactaggaa cttcgtatat ttgttcacct    4680
acatcatcat gtggtttttg ccataaaaaa aaaataatta tgatgtgaaa ctaagtttta    4740
caaggtttga aaatatgaat ttgatgtcaa aatctggaca aggaaaaacg cacatgacga    4800
tcatgtgatg acaatcgtaa atttgtaata aggaagaaca tgaccaataa gatagaaaga    4860
tttgtacacc agtgtagtgc ttgccacaca agctccgatg cttaagttat aagctggtgt    4920
atttgtaatg aaatttgac ctacgacatc catattagta ttttcgagtt atattaggtt    4980
aatgctctag ctagtgggtc                                                5000
```

<210> SEQ ID NO 35
<211> LENGTH: 1323
<212> TYPE: DNA
<213> ORGANISM: Citrullus lanatus

<400> SEQUENCE: 35

```
atgatggcaa tgttgtctac caaagctagc catgattctc atggtcaaga ttcttcctac      60
tttttaggat ggcaagaata tgagaagaac ccatatcacc ctactcgaaa ccccaccgga     120
attatccaaa tgggtctcgc cgaaaacaag ctatgttatg acttattgga tgagtggatg     180
gagaacaatc cagacgcttt gggattgaga agaaatggag tgtctgtgtt tagagaattg     240
gctctatttc aagactatca tggcttgcct gcttttaaaa aggtgttggt tgaattaatg     300
```

```
gaggaaatac gaggaaagaa agtgagattt gatatgaata aactggtcct caccgctggt    360
gcaacttctg cgaatgagat cctaatgttt tgtcttgccg aacctggtga agctttcctt    420
gttcccactc cttactatcc tgggtttgac agagacttaa aatggcgtac aggcgtacga    480
ataattccaa ttcagtgttc aagttcaaac ggtttccgaa tcaccgcagc ggcaatggaa    540
gaagcgaggg aacgagccca aaagctgaaa ttacgagtca aaggggtttt aatcacgaac    600
ccatcgaatc cactgggaac acattgagc tgcaaggagc tgaatttagt ggtgaatttc    660
gccacagcca acgcaataca catagtgagc gacgagatat attcggccac agttttctca    720
tccccaaatt tccaaaccat catggaccaa cgcctacaaa atccccaat ttgggagcgc    780 atccacgtgg tgtacagcct atccaaggat ctaggcttgc ctgggttccg cgtaggcatg    840
atttattcaa acaaccccaa agtagtggct gcagctacca aaatgtcgag ctttggtcta    900
gtttcatctc agacacaata tttggtgtca caaatgctag agacccccaa attccgagag    960
aattacatga cggaaatgaa gatgaggatc aggaagagga aaggaatgtt ggagttgggg   1020
ctccgaaaag ccggaatcag gtgtttgaaa gggaatgcgg gtttgttttg ttgggtggat   1080
atgaggcatc ttttaaaata tccaagtttc aacaggaaaa tggagttttg gaagaggatt   1140
ttgtgtgagg ttgggcttaa tgtctcgccc ggttcggctt gtcattgttc tgaaccgggt   1200
tggttcagaa tgtgctttgc taacatgtcg gaacacactt tgatggtggc gatgtgtcgt   1260
cttaaggcat ttgtggagtc taccttatct ctcaaaggcc accagaaggt cttccttaac   1320
taa                                                                 1323
```

<210> SEQ ID NO 36
<211> LENGTH: 440
<212> TYPE: PRT
<213> ORGANISM: Citrullus lanatus

<400> SEQUENCE: 36

```
Met Met Ala Met Leu Ser Thr Lys Ala Ser His Asp Ser His Gly Gln
1               5                   10                  15

Asp Ser Ser Tyr Phe Leu Gly Trp Gln Glu Tyr Glu Lys Asn Pro Tyr
                20                  25                  30

His Pro Thr Arg Asn Pro Thr Gly Ile Ile Gln Met Gly Leu Ala Glu
            35                  40                  45

Asn Lys Leu Cys Tyr Asp Leu Leu Asp Glu Trp Met Glu Asn Asn Pro
        50                  55                  60

Asp Ala Leu Gly Leu Arg Arg Asn Gly Val Ser Val Phe Arg Glu Leu
65                  70                  75                  80

Ala Leu Phe Gln Asp Tyr His Gly Leu Pro Ala Phe Lys Lys Val Leu
                85                  90                  95

Val Glu Leu Met Glu Glu Ile Arg Gly Lys Lys Val Arg Phe Asp Met
                100                 105                 110

Asn Lys Leu Val Leu Thr Ala Gly Ala Thr Ser Ala Asn Glu Ile Leu
            115                 120                 125

Met Phe Cys Leu Ala Glu Pro Gly Glu Ala Phe Leu Val Pro Thr Pro
        130                 135                 140

Tyr Tyr Pro Gly Phe Asp Arg Asp Leu Lys Trp Arg Thr Gly Val Arg
145                 150                 155                 160

Ile Ile Pro Ile Gln Cys Ser Ser Asn Gly Phe Arg Ile Thr Ala
                165                 170                 175

Ala Ala Met Glu Glu Ala Arg Glu Arg Ala Gln Lys Leu Lys Leu Arg
                180                 185                 190
```

-continued

```
Val Lys Gly Val Leu Ile Thr Asn Pro Ser Asn Pro Leu Gly Thr Thr
        195                 200                 205

Leu Ser Cys Lys Glu Leu Asn Leu Val Val Asn Phe Ala Thr Ala Asn
    210                 215                 220

Ala Ile His Ile Val Ser Asp Glu Ile Tyr Ser Ala Thr Val Phe Ser
225                 230                 235                 240

Ser Pro Asn Phe Gln Thr Ile Met Asp Gln Arg Leu Gln Lys Ser Pro
                245                 250                 255

Ile Trp Glu Arg Ile His Val Val Tyr Ser Leu Ser Lys Asp Leu Gly
                260                 265                 270

Leu Pro Gly Phe Arg Val Gly Met Ile Tyr Ser Asn Asn Pro Lys Val
            275                 280                 285

Val Ala Ala Ala Thr Lys Met Ser Ser Phe Gly Leu Val Ser Ser Gln
        290                 295                 300

Thr Gln Tyr Leu Val Ser Gln Met Leu Gly Asp Pro Lys Phe Arg Glu
305                 310                 315                 320

Asn Tyr Met Thr Glu Met Lys Met Arg Ile Arg Lys Arg Lys Gly Met
                325                 330                 335

Leu Glu Leu Gly Leu Arg Lys Ala Gly Ile Arg Cys Leu Lys Gly Asn
            340                 345                 350

Ala Gly Leu Phe Cys Trp Val Asp Met Arg His Leu Leu Lys Tyr Pro
        355                 360                 365

Ser Phe Gln Gln Glu Met Glu Phe Trp Lys Arg Ile Leu Cys Glu Val
    370                 375                 380

Gly Leu Asn Val Ser Pro Gly Ser Ala Cys His Cys Ser Glu Pro Gly
385                 390                 395                 400

Trp Phe Arg Met Cys Phe Ala Asn Met Ser Glu His Thr Leu Met Val
                405                 410                 415

Ala Met Cys Arg Leu Lys Ala Phe Val Glu Ser Thr Leu Ser Leu Lys
                420                 425                 430

Gly His Gln Lys Val Phe Leu Asn
        435                 440
```